US012723104B2

(12) United States Patent
Blackwood et al.

(10) Patent No.: US 12,723,104 B2
(45) **Date of Patent: *Sep. 1, 2026**

(54) λ ANTIBODIES

(71) Applicant: KYMAB LIMITED, Cambridge (GB)

(72) Inventors: John Kenneth Blackwood, Cambridge (GB); Wei Wang, Cambridge (GB); Benjamin Henry Jenkins, Farnborough (GB)

(73) Assignee: KYMAB LIMITED, Cambridge (GB)

( * ) Notice: Subject to any disclaimer, the term of this patent is extended or adjusted under 35 U.S.C. 154(b) by 1280 days.

This patent is subject to a terminal disclaimer.

(21) Appl. No.: 17/604,992

(22) PCT Filed: May 14, 2020

(86) PCT No.: PCT/EP2020/063515

§ 371 (c)(1),
(2) Date: Oct. 19, 2021

(87) PCT Pub. No.: WO2020/229621

PCT Pub. Date: Nov. 19, 2020

(65) Prior Publication Data

US 2023/0250192 A1 Aug. 10, 2023

(30) Foreign Application Priority Data

May 15, 2019 (GB) .................................... 1906816
Jun. 7, 2019 (GB) .................................... 1908190
Dec. 20, 2019 (GB) .................................... 1919077
Dec. 20, 2019 (WO) ................ PCT/EP2019/086808

(51) Int. Cl.
*C07K 16/36* (2006.01)
*C07K 16/46* (2006.01)

(52) U.S. Cl.
CPC ........ *C07K 16/468* (2013.01); *C07K 2317/14* (2013.01); *C07K 2317/31* (2013.01); *C07K 2317/515* (2013.01)

(58) Field of Classification Search
None
See application file for complete search history.

(56) References Cited

U.S. PATENT DOCUMENTS 8,062,635 B2 * 11/2011 Hattori ............... C07K 16/2866 514/14.1
9,840,554 B2 12/2017 Gu et al.
10,815,308 B2 * 10/2020 Wang ........................ A61P 7/02
11,976,135 B2 * 5/2024 Wang ..................... C07K 16/36
2011/0217237 A1 9/2011 Chen et al.
2014/0348838 A1 11/2014 Tarcsa
2019/0233543 A1 8/2019 Agrawal et al.
2020/0199250 A1 * 6/2020 Wang ........................ A61P 7/02
2023/0039447 A1 2/2023 Blackwood et al.

FOREIGN PATENT DOCUMENTS

CN 104854133 A 8/2015
CN 106103730 A 11/2016
CN 107921285 A 4/2018
CN 113939541 A 1/2022
JP 2018-535213 A 11/2018
WO WO 1994/013804 A1 6/1994
WO WO 2002/050118 A2 6/2002
WO WO 2007/003421 A2 1/2007
WO WO 2008/097461 A2 8/2008
WO WO 2008/148519 A2 12/2008
WO WO 2009/139822 A1 11/2009
WO WO 2014/058389 A1 4/2014
WO WO 2014/151834 A2 9/2014
WO WO 2015/103072 A1 7/2015
WO WO 2015/139046 A1 9/2015
WO WO 2016/154593 A1 9/2016
WO WO-2017072310 A1 * 5/2017 ............ C07K 16/00
WO WO 2018/209265 A1 11/2018
WO WO 2018/234575 A1 12/2018
WO WO 2019/008123 A2 1/2019
WO WO 2020/229621 A1 11/2020
WO WO 2021/123090 A1 6/2021

OTHER PUBLICATIONS

Yu et al., MAbs. Jan.-Dec. 2022;14(1):2044977. doi: 10.1080/19420862.2022.2044977. PMID: 35275041 PMCID: PMC8920188.*
You et al., Appl Microbiol Biotechnol. Jul. 2018;102(14):5953-5964. doi: 10.1007/s00253-018-8986-5. Epub May 8, 2018. PMID: 29740673.*
Anarci: Antigen Receptor Numbering and Receptor Classification, 2016.
Dumont et al., Human Cell Lines for Biopharmaceutical Manufacturing: History, Status, and Future Perspectives, Critical Reviews in Biotechnology, vol. 36, Issue 6, pp. 1110-1122, Nov. 1, 2016.
Gibson et al., N-Terminal or Signal Peptide Sequence Engineering Prevents Truncation of Human Monoclonal Antibody Light Chains, Biotechnology and Bioengineering, vol. 114, Issue 9, pp. 1970-1977, Sep. 2017.
Goodson, Dental Applications, Medical Applications of Controlled Release, vol. 2, pp. 115-138, Jan. 1, 1984.
Haryadi et al., Optimization of Heavy Chain and Light Chain Signal Peptides for High Level Expression of Therapeutic Antibodies in CHO Cells, PLoS One vol. 10, No. 2, Article No. e0116878, pp. 1-16, Feb. 23, 2015.
Kotia et al., Analysis of Monoclonal Antibody Product Heterogeneity Resulting from Alternate Cleavage Sites of Signal Peptide, Analytical Biochemistry, vol. 399, Issue 2, pp. 190-195, Apr. 15, 2010.
Langer, New Methods of Drug Delivery, Science, vol. 249, Issue 4976, pp. 1527-1533, Sep. 28, 1990.
Lefranc et al., IMGT Unique Numbering for Immunoglobulin and T Cell Receptor Variable Domains and Ig Superfamily V-like Domains, Developmental & Comparative Immunology, vol. 27, Issue 1, pp. 55-77, Jan. 2003.

(Continued)

*Primary Examiner* — Michael Szperka
(74) *Attorney, Agent, or Firm* — LATHROP GPM LLP; James H. Velema, Esq.; James V. DeGiulio

(57) ABSTRACT

Immunoglobulin lambda variable domain sequence adapted for expression with non-native N terminal signal peptide, comprising a deletion at IMGT position 1.

19 Claims, 5 Drawing Sheets

Specification includes a Sequence Listing.

(56) References Cited

OTHER PUBLICATIONS

Lefranc et al., Immunoglobulins: 25 years of Immunoinformatics and IMGT-Ontology, Biomolecules, 2014, 4: 1102-1139.
Liu et al., In vitro and in vivo modifications of recombinant and human IgG antibodies, mAbs, Sep./Oct. 2014, 65: 1145-1154.
Powell et al., Compendium of Excipients for Parenteral Formulations, PDA Journal of Pharmaceutical Science and Technology, vol. 52, No. 5, pp. 238-311, Sep. 1998.
Prabakaran et al., Expressed antibody repertoires in human cord blood cells: 454 sequencing and IMGT/High V-QUEST Analysis of germline gene usage, junctional diversity, and somatic mutations, Immunogenetics, 2012, 64: 337-350.
Sefton, Implantable Pumps, Critical Reviews in Biomedical Engineering, vol. 14, No. 3, pp. 201-240, 1987.
Shen et al., Removal of a C-Terminal Serine Residue Proximal to the Inter-Chain Disulfide Bond of a Human IgG1 Lambda Light Chain Mediates Enhanced Antibody Stability and Antibody Dependent Cell-Mediated Cytotoxicity, mAbs, vol. 5, No. 3, pp. 418-431, May 1, 2013.
Song et al., Alteration of amino acid residues at the L-chain N-terminus and in complementarity-determining region 3 increases affinity of a recombinant F(ab) for the human N blood group antigen, Immunohematology, Transfusion, Feb. 2004, 44: 173-186.
Spidel et al., Rapid high-throughput cloning and stable expression of antibodies in HEK293 cells, Journal of Immunological Methods, 2019, 439: 50-58.
Whittle et al., Expression in COS Cells of a Mouse–human Chimaeric B72.3 Antibody, Protein Engineering, Design and Selection, vol. 1, Issue 6, pp. 499-505, Jun. 1, 1987.
Gupta et al., "Vector-related stratagems for enhanced monoclonal antibody production in mammalian cells", Biotech. Adv., Dec. 2019, 37(8): 107415.
International Search Report and Written Opinion for PCT International Patent Application No. PCT/EP2020/086920, dated Apr. 6, 2021.
International Search Report and Written Opinion for PCT International Patent Application No. PCT/EP2020/063515, dated Aug. 21, 2020.
You et al., Efficient mAb production in CHO cells with optimized signal peptide, codon, and UTR, Appl Microbiol Biotechnol, vol. 102, No. 14, Jul. 2018, pp. 5953-5964.
Edwards et al. "The Remarkable Flexibility of the Human Antibody Repertoire; Isolation of Over One Thousand Differnet Antibodies to a Single Protein, BLyS", J. Mol. Biol. (2003) 334, 103-118.
Goel et al., "Plasticity within the Antigen-Combining Site May Manifest as Molecular Mimicry in the Humoral Immune Response", J Immunol., Dec. 15, 2004, 173(12): 7358-7367.
Janeway et al., "Structure of the Antibody Molecule and Immunoglobulin Genes", Immunobiology, 3rd edition, 1997, pp. 3:1-3:21.
Kanyavuz et al., "Breaking the law: unconventional strategies for antibody diversification", Nat Rev Immunol., Jun. 2019, 19(6): 355-368.
Lloyd et al., "Modelling the human immune response: performance of a 10" human antibody repertoire against a broad panel of therapeutically relevant antigens", Protein Eng Des Sel., Mar. 2009, 22(3): 159-168, Epublished Oct. 29, 2008.
Rudikoff et al., "Single amino acid substitution altering antigen-binding specificity", Proc Natl Acad Sci USA, Mar. 1982, 79(6): 1979-1983.

* cited by examiner (A)

MAWTALLLGLLSHCTGSVTSYVLTQPPSVSVAPGETARITCGGDNIGRKSVYWYQ
QKSGQAPVLVIYYDSDRPSGIPERFSGSNSGNTATLTISRVEAGDEADYYCQVWD
GSSDHWVFGGGTKLTVL

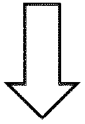

YVLTQPPSVSVAPGETARITCGGDNIGRKSVYWYQQKSGQAPVLVIYYDSDRPSG
IPERFSGSNSGNTATLTISRVEAGDEADYYCQVWDGSSDHWVFGGGTKLTVL (B)

MSVPTQVLGLLLLWLTDARCSYVLTQPPSVSVAPGETARITCGGDNIGRKSVYWY
QQKSGQAPVLVIYYDSDRPSGIPERFSGSNSGNTATLTISRVEAGDEADYYCQVW
DGSSDHWVFGGGTKLTVL

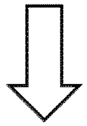

SYVLTQPPSVSVAPGETARITCGGDNIGRKSVYWYQQKSGQAPVLVIYYDSDRPS
GIPERFSGSNSGNTATLTISRVEAGDEADYYCQVWDGSSDHWVFGGGTKLTVL (C)

MSVPTQVLGLLLLWLTDARCYVLTQPPSVSVAPGETARITCGGDNIGRKSVYWYQ
QKSGQAPVLVIYYDSDRPSGIPERFSGSNSGNTATLTISRVEAGDEADYYCQVWD
GSSDHWVFGGGTKLTVL

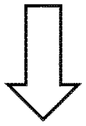

YVLTQPPSVSVAPGETARITCGGDNIGRKSVYWYQQKSGQAPVLVIYYDSDRPSG
IPERFSGSNSGNTATLTISRVEAGDEADYYCQVWDGSSDHWVFGGGTKLTVL

Figure 1

| | |
|---|---|
| L 1 | - |
| L 2 | Y |
| L 3 | V |
| L 4 | L |
| L 5 | T |
| L 6 | Q |
| L 7 | P |
| L 8 | P |
| L 9 | S |
| L 10 | - |
| L 11 | V |
| L 12 | S |
| L 13 | V |
| L 14 | A |
| L 15 | P |
| L 16 | G |
| L 17 | E |
| L 18 | T |
| L 19 | A |
| L 20 | R |
| L 21 | I |
| L 22 | T |
| L 23 | C |
| L 24 | G |
| L 25 | G |
| L 26 | D |
| L 27 | N |
| L 28 | I |
| L 29 | G |
| L 30 | - |
| L 31 | - |
| L 32 | - |
| L 33 | - |
| L 34 | - |
| L 35 | - |
| L 36 | R |
| L 37 | K |
| L 38 | S |
| L 39 | V |
| L 40 | Y |
| L 41 | W |
| L 42 | Y |
| L 43 | Q |
| L 44 | Q |
| L 45 | K |
| L 46 | S |
| L 47 | G |
| L 48 | Q |
| L 49 | A |
| L 50 | P |
| L 51 | V |
| L 52 | L |
| L 53 | V |
| L 54 | I |
| L 55 | Y |
| L 56 | Y |
| L 57 | D |
| L 58 | - |
| L 59 | - |
| L 60 | - |
| L 61 | - |
| L 62 | - |
| L 63 | - |
| L 64 | - |
| L 65 | S |
| L 66 | D |
| L 67 | R |
| L 68 | P |
| L 69 | S |
| L 70 | G |
| L 71 | I |
| L 72 | P |
| L 73 | - |
| L 74 | E |
| L 75 | R |
| L 76 | F |
| L 77 | S |
| L 78 | G |
| L 79 | S |
| L 80 | N |
| L 81 | - |
| L 82 | - |
| L 83 | S |
| L 84 | G |
| L 85 | N |
| L 86 | T |
| L 87 | A |
| L 88 | T |
| L 89 | L |
| L 90 | T |
| L 91 | I |
| L 92 | S |
| L 93 | R |
| L 94 | V |
| L 95 | E |
| L 96 | A |
| L 97 | G |
| L 98 | D |
| L 99 | E |
| L 100 | A |
| L 101 | D |
| L 102 | Y |
| L 103 | Y |
| L 104 | C |
| L 105 | Q |
| L 106 | V |
| L 107 | W |
| L 108 | D |
| L 109 | G |
| L 110 | S |
| L 111 | - |
| L 112 | - |
| L 113 | S |
| L 114 | D |
| L 115 | H |
| L 116 | W |
| L 117 | V |
| L 118 | F |
| L 119 | G |
| L 120 | G |
| L 121 | G |
| L 122 | T |
| L 123 | K |
| L 124 | L |
| L 125 | T |
| L 126 | V |
| L 127 | L |

Figure 2

A
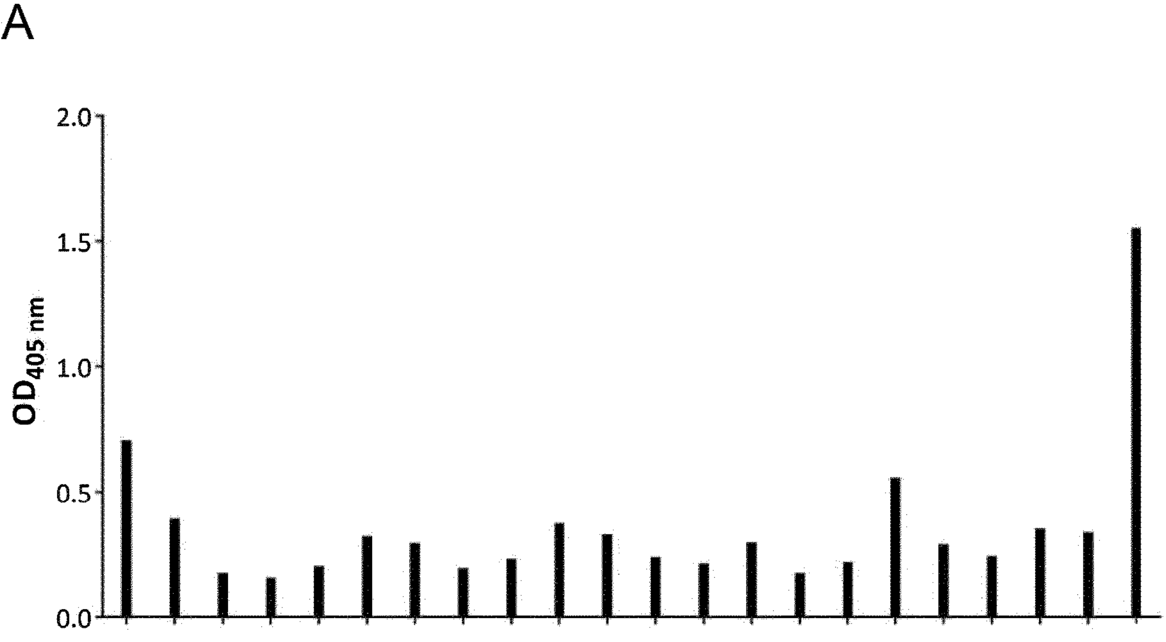
B
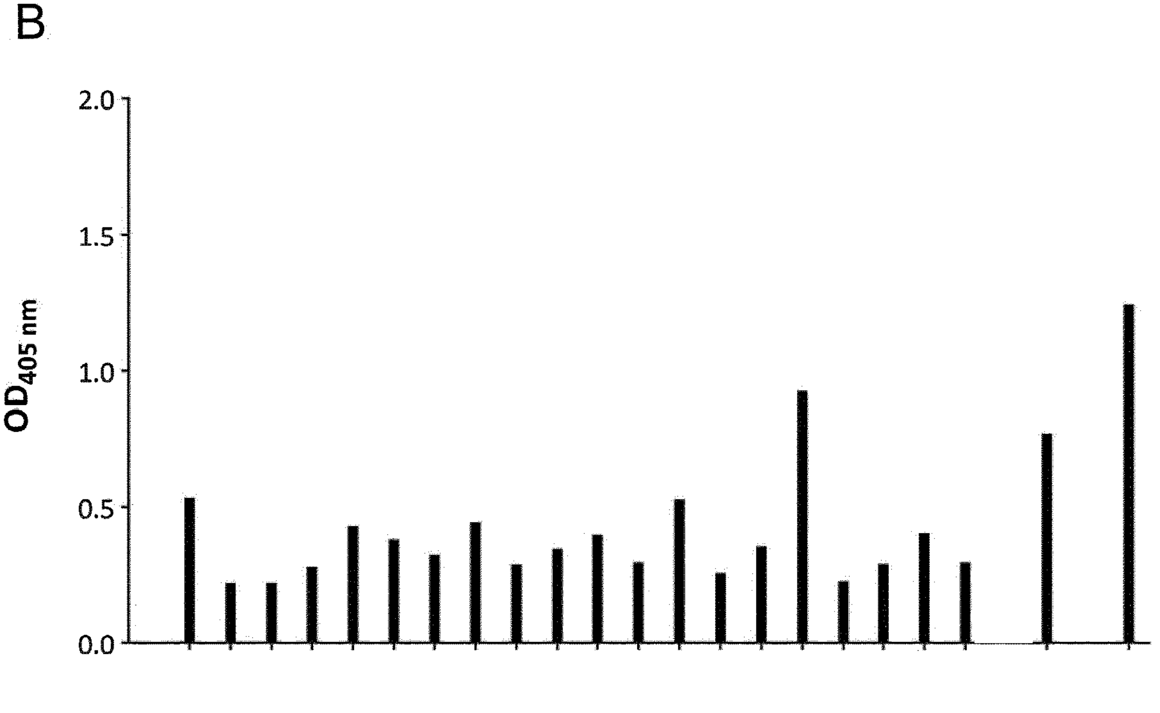
Figure 4

SEQUENCE LISTING

<160> NUMBER OF SEQ ID NOS: 115

<210> SEQ ID NO 1
<211> LENGTH: 98
<212> TYPE: PRT
<213> ORGANISM: Homo Sapiens

<400> SEQUENCE: 1

Gln Ser Val Leu Thr Gln Pro Pro Ser Val Ser Glu Ala Pro Arg Gln
1 5 10 15

Arg Val Thr Ile Ser Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Tyr Asp Asp Leu Leu Pro Ser Gly Val Ser Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ala Trp Asp Asp Ser Leu
85 90 95

Asn Gly

<210> SEQ ID NO 2
<211> LENGTH: 99
<212> TYPE: PRT
<213> ORGANISM: Homo Sapiens

<400> SEQUENCE: 2

Gln Ser Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Ser Ser
85 90 95

Leu Ser Gly

<210> SEQ ID NO 3
<211> LENGTH: 98
<212> TYPE: PRT
<213> ORGANISM: Homo Sapiens

<400> SEQUENCE: 3

Gln Ser Val Leu Thr Gln Pro Pro Ser Val Ser Ala Ala Pro Gly Gln
1 5 10 15

Lys Val Thr Ile Ser Cys Ser Gly Ser Ser Ser Asp Met Gly Asn Tyr
20 25 30

Ala Val Ser Trp Tyr Gln Gln Leu Pro Gly Thr Ala Pro Lys Leu Leu
35 40 45

Ile Tyr Glu Asn Asn Lys Arg Pro Ser Gly Ile Pro Asp Arg Phe Ser
50 55 60

Gly Ser Lys Ser Gly Thr Ser Ala Thr Leu Gly Ile Thr Gly Leu Trp

```
65                  70                  75                  80

Pro Glu Asp Glu Ala Asp Tyr Tyr Cys Leu Ala Trp Asp Thr Ser Pro
                85                  90                  95

Arg Ala


<210> SEQ ID NO 4
<211> LENGTH: 98
<212> TYPE: PRT
<213> ORGANISM: Homo Sapiens

<400> SEQUENCE: 4

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly


<210> SEQ ID NO 5
<211> LENGTH: 98
<212> TYPE: PRT
<213> ORGANISM: Homo Sapiens

<400> SEQUENCE: 5

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly


<210> SEQ ID NO 6
<211> LENGTH: 99
<212> TYPE: PRT
<213> ORGANISM: Homo Sapiens

<400> SEQUENCE: 6

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45
```

```
Leu Ile Tyr Gly Asn Ser Asn Arg Pro Ser Gly Val Pro Asp Gln Phe
    50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Lys Ala Trp Asp Asn Ser
                85                  90                  95

Leu Asn Ala


<210> SEQ ID NO 7
<211> LENGTH: 98
<212> TYPE: PRT
<213> ORGANISM: Homo Sapiens

<400> SEQUENCE: 7

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala


<210> SEQ ID NO 8
<211> LENGTH: 97
<212> TYPE: PRT
<213> ORGANISM: Homo Sapiens

<400> SEQUENCE: 8

Gln Ser Val Leu Thr Gln Pro Pro Ser Val Ser Trp Ala Thr Arg Gln
1               5                   10                  15

Arg Leu Thr Val Ser Cys Thr Gly Ser Ser Ser Asn Thr Gly Thr Gly
            20                  25                  30

Tyr Asn Val Asn Cys Trp Gln Leu Pro Arg Thr Asp Pro Lys Leu Leu
        35                  40                  45

Arg His Gly Asp Lys Asn Trp Ala Ser Trp Val Ser Asp Gln Phe Ser
    50                  55                  60

Gly Ser Lys Ser Gly Ser Leu Ala Ser Leu Gly Thr Thr Gly Leu Trp
65                  70                  75                  80

Ala Glu Asp Lys Thr Asp Tyr His Cys Gln Ser Arg Asp Ile Cys Val
                85                  90                  95

Leu


<210> SEQ ID NO 9
<211> LENGTH: 97
<212> TYPE: PRT
<213> ORGANISM: Homo Sapiens

<400> SEQUENCE: 9

Gln Ser Ala Leu Ile Gln Pro Pro Ser Val Ser Gly Ser Pro Gly Gln
1               5                   10                  15
```

```
Ser Val Thr Ile Ser Cys Thr Gly Thr Ser Ser Asp Val Gly Ser Tyr
            20                  25                  30

Asp Tyr Val Ser Trp Tyr Gln Gln His Pro Gly Thr Val Pro Lys Pro
        35                  40                  45

Met Ile Tyr Asn Val Asn Thr Gln Pro Ser Gly Val Pro Asp Arg Phe
    50                  55                  60

Ser Gly Ser Lys Ser Gly Asn Thr Ala Ser Met Thr Ile Ser Gly Leu
65                  70                  75                  80

Gln Ala Glu Asp Glu Ala Asp Tyr Cys Cys Ser Tyr Thr Ser Ser Ala
                85                  90                  95

Thr


<210> SEQ ID NO 10
<211> LENGTH: 99
<212> TYPE: PRT
<213> ORGANISM: Homo Sapiens

<400> SEQUENCE: 10

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Phe


<210> SEQ ID NO 11
<211> LENGTH: 99
<212> TYPE: PRT
<213> ORGANISM: Homo Sapiens

<400> SEQUENCE: 11

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Phe


<210> SEQ ID NO 12
<211> LENGTH: 99
<212> TYPE: PRT
<213> ORGANISM: Homo Sapiens
```

<400> SEQUENCE: 12

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Glu Val Ser Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Thr Ser Ser
85 90 95

Ser Thr Leu

<210> SEQ ID NO 13
<211> LENGTH: 99
<212> TYPE: PRT
<213> ORGANISM: Homo Sapiens

<400> SEQUENCE: 13

Gln Ser Ala Leu Thr Gln Pro Pro Ser Val Ser Gly Ser Pro Gly Gln
1 5 10 15

Ser Val Thr Ile Ser Cys Thr Gly Thr Ser Ser Asp Val Gly Ser Tyr
20 25 30

Asn Arg Val Ser Trp Tyr Gln Gln Pro Pro Gly Thr Ala Pro Lys Leu
35 40 45

Met Ile Tyr Glu Val Ser Asn Arg Pro Ser Gly Val Pro Asp Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Leu Tyr Thr Ser Ser
85 90 95

Ser Thr Phe

<210> SEQ ID NO 14
<211> LENGTH: 99
<212> TYPE: PRT
<213> ORGANISM: Homo Sapiens

<400> SEQUENCE: 14

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Ser Tyr
20 25 30

Asn Leu Val Ser Trp Tyr Gln Gln His Pro Gly Lys Ala Pro Lys Leu
35 40 45

Met Ile Tyr Glu Gly Ser Lys Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Cys Ser Tyr Ala Gly Ser
85 90 95

Ser Thr Leu

-continued

<210> SEQ ID NO 15
<211> LENGTH: 99
<212> TYPE: PRT
<213> ORGANISM: Homo Sapiens

<400> SEQUENCE: 15

```
Gln Ser Ala Leu Thr Gln Pro Pro Phe Val Ser Gly Ala Pro Gly Gln
1               5                   10                  15

Ser Val Thr Ile Ser Cys Thr Gly Thr Ser Ser Asp Val Gly Asp Tyr
            20                  25                  30

Asp His Val Phe Trp Tyr Gln Lys Arg Leu Ser Thr Thr Ser Arg Leu
        35                  40                  45

Leu Ile Tyr Asn Val Asn Thr Arg Pro Ser Gly Ile Ser Asp Leu Phe
    50                  55                  60

Ser Gly Ser Lys Ser Gly Asn Met Ala Ser Leu Thr Ile Ser Gly Leu
65                  70                  75                  80

Lys Ser Glu Val Glu Ala Asn Tyr His Cys Ser Leu Tyr Ser Ser Ser
                85                  90                  95

Tyr Thr Phe
```

<210> SEQ ID NO 16
<211> LENGTH: 97
<212> TYPE: PRT
<213> ORGANISM: Homo Sapiens

<400> SEQUENCE: 16

```
Gln Ser Val Leu Thr Gln Pro Arg Ser Val Ser Arg Ser Pro Gly Gln
1               5                   10                  15

Val Thr Ile Phe Cys Thr Gly Thr Ser Ser Asp Ile Gly Gly Tyr Asp
            20                  25                  30

Leu Val Ser Trp Cys Gln His Pro Gly Lys Ala Pro Lys Leu Met Ile
        35                  40                  45

Tyr Asp Val Ala Asn Trp Pro Ser Gly Ala Pro Gly Cys Phe Ser Gly
    50                  55                  60

Ser Lys Ser Gly Asn Thr Ala Ser Leu Thr Ile Ser Gly Leu Gln Ala
65                  70                  75                  80

Glu Asp Glu Ala Asp Tyr Tyr Cys Ser Ser Tyr Ala Gly Ser Tyr Asn
                85                  90                  95

Phe
```

<210> SEQ ID NO 17
<211> LENGTH: 97
<212> TYPE: PRT
<213> ORGANISM: Homo Sapiens

<400> SEQUENCE: 17

```
Gln Ser Val Leu Thr Gln Pro Arg Ser Val Ser Arg Ser Pro Gly Gln
1               5                   10                  15

Val Thr Ile Phe Cys Thr Gly Thr Ser Ser Asp Ile Gly Gly Tyr Asp
            20                  25                  30

Leu Val Ser Trp Cys Gln His Pro Gly Lys Ala Pro Lys Leu Met Ile
        35                  40                  45

Tyr Asp Val Gly Asn Trp Pro Ser Gly Ala Pro Gly Cys Phe Ser Gly
    50                  55                  60

Ser Lys Ser Gly Asn Thr Ala Ser Leu Thr Ile Ser Gly Leu Gln Ala
65                  70                  75                  80

Glu Asp Glu Ala Asp Tyr Tyr Cys Ser Ser Tyr Ala Gly Ser Tyr Asn
```

```
                85                  90                  95

Phe


<210> SEQ ID NO 18
<211> LENGTH: 95
<212> TYPE: PRT
<213> ORGANISM: Homo Sapiens

<400> SEQUENCE: 18

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala
                85                  90                  95


<210> SEQ ID NO 19
<211> LENGTH: 95
<212> TYPE: PRT
<213> ORGANISM: Homo Sapiens

<400> SEQUENCE: 19

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr Ala
                85                  90                  95


<210> SEQ ID NO 20
<211> LENGTH: 96
<212> TYPE: PRT
<213> ORGANISM: Homo Sapiens

<400> SEQUENCE: 20

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80
```

```
Asp Glu Ala Asp Tyr Tyr Cys Tyr Ser Thr Asp Ser Ser Gly Asn His
                85                  90                  95


<210> SEQ ID NO 21
<211> LENGTH: 96
<212> TYPE: PRT
<213> ORGANISM: Homo Sapiens

<400> SEQUENCE: 21

Ser Tyr Glu Leu Thr Gln Pro His Ser Val Ser Val Ala Thr Ala Gln
1               5                   10                  15

Met Ala Arg Ile Thr Cys Gly Gly Asn Asn Ile Gly Ser Lys Ala Val
            20                  25                  30

His Trp Tyr Gln Gln Lys Pro Gly Gln Asp Pro Val Leu Val Ile Tyr
        35                  40                  45

Ser Asp Ser Asn Arg Pro Ser Gly Ile Pro Glu Arg Phe Ser Gly Ser
    50                  55                  60

Asn Pro Gly Asn Thr Thr Thr Leu Thr Ile Ser Arg Ile Glu Ala Gly
65                  70                  75                  80

Asp Glu Ala Asp Tyr Tyr Cys Gln Val Trp Asp Ser Ser Ser Asp His
                85                  90                  95


<210> SEQ ID NO 22
<211> LENGTH: 93
<212> TYPE: PRT
<213> ORGANISM: Homo Sapiens

<400> SEQUENCE: 22

Ser Tyr Glu Leu Thr Gln Pro Pro Ala Val Ser Val Ser Pro Gly Gln
1               5                   10                  15

Thr Ala Arg Ile Ser Cys Ser Gly Asp Val Leu Arg Asp Asn Tyr Ala
            20                  25                  30

Asp Trp Tyr Pro Gln Lys Pro Gly Gln Ala Pro Val Leu Val Ile Tyr
        35                  40                  45

Lys Asp Gly Glu Arg Pro Ser Gly Ile Pro Glu Arg Phe Ser Gly Ser
    50                  55                  60

Thr Ser Gly Asn Thr Thr Ala Leu Thr Ile Ser Arg Val Leu Thr Lys
65                  70                  75                  80

Gly Gly Ala Asp Tyr Tyr Cys Phe Ser Gly Asp Asn Asn
                85                  90


<210> SEQ ID NO 23
<211> LENGTH: 96
<212> TYPE: PRT
<213> ORGANISM: Homo Sapiens

<400> SEQUENCE: 23

Ser Tyr Glu Leu Thr Gln Pro Pro Ser Val Ser Val Ser Leu Gly Gln
1               5                   10                  15

Met Ala Arg Ile Thr Cys Ser Gly Glu Ala Leu Pro Lys Lys Tyr Ala
            20                  25                  30

Tyr Trp Tyr Gln Gln Lys Pro Gly Gln Phe Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Ile Val Thr Leu Thr Ile Ser Gly Val Gln Ala Glu
65                  70                  75                  80

Asp Glu Ala Asp Tyr Tyr Cys Leu Ser Ala Asp Ser Ser Gly Thr Tyr
```

```
                85                  90                  95


<210> SEQ ID NO 24
<211> LENGTH: 96
<212> TYPE: PRT
<213> ORGANISM: Homo Sapiens

<400> SEQUENCE: 24

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95


<210> SEQ ID NO 25
<211> LENGTH: 96
<212> TYPE: PRT
<213> ORGANISM: Homo Sapiens

<400> SEQUENCE: 25

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95


<210> SEQ ID NO 26
<211> LENGTH: 94
<212> TYPE: PRT
<213> ORGANISM: Homo Sapiens

<400> SEQUENCE: 26

Ser Tyr Glu Leu Thr Gln Leu Pro Ser Val Ser Val Ser Pro Gly Gln
1               5                   10                  15

Thr Ala Arg Ile Thr Cys Ser Gly Asp Val Leu Gly Glu Asn Tyr Ala
            20                  25                  30

Asp Trp Tyr Gln Gln Lys Pro Gly Gln Ala Pro Glu Leu Val Ile Tyr
        35                  40                  45

Glu Asp Ser Glu Arg Tyr Pro Gly Ile Pro Glu Arg Phe Ser Gly Ser
    50                  55                  60

Thr Ser Gly Asn Thr Thr Thr Leu Thr Ile Ser Arg Val Leu Thr Glu
65                  70                  75                  80

Asp Glu Ala Asp Tyr Tyr Cys Leu Ser Gly Asp Glu Asp Asn
                85                  90
```

<210> SEQ ID NO 27
<211> LENGTH: 96
<212> TYPE: PRT
<213> ORGANISM: Homo Sapiens

<400> SEQUENCE: 27

```
Ser Tyr Glu Leu Met Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95
```

<210> SEQ ID NO 28
<211> LENGTH: 94
<212> TYPE: PRT
<213> ORGANISM: Homo Sapiens

<400> SEQUENCE: 28

```
Ser Tyr Glu Leu Thr Gln Pro Ser Ser Val Ser Val Ser Pro Gly Gln
1               5                   10                  15

Thr Ala Arg Ile Thr Cys Ser Gly Asp Val Leu Ala Lys Lys Tyr Ala
            20                  25                  30

Arg Trp Phe Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Ala Gln Val Glu
65                  70                  75                  80

Asp Glu Ala Asp Tyr Tyr Cys Tyr Ser Ala Ala Asp Asn Asn
                85                  90
```

<210> SEQ ID NO 29
<211> LENGTH: 94
<212> TYPE: PRT
<213> ORGANISM: Homo Sapiens

<400> SEQUENCE: 29

```
Ser Ser Glu Leu Ser Gln Glu Pro Ala Val Ser Val Ala Leu Gly Thr
1               5                   10                  15

Ala Arg Ile Thr Cys Gln Gly Asp Ser Ile Glu Asp Ser Val Val Asn
            20                  25                  30

Trp Tyr Lys Gln Lys Pro Ser Gln Ala Pro Gly Leu Val Ile Leu Asn
        35                  40                  45

Ser Val Gln Ser Ser Gly Ile Pro Lys Lys Phe Ser Gly Ser Ser Ser
    50                  55                  60

Gly Asn Met Ala Thr Leu Thr Ile Thr Gly Ile Gln Val Glu Asp Lys
65                  70                  75                  80

Ala Asp Tyr Tyr Cys Gln Ser Trp Asp Ser Ser Arg Thr His
                85                  90
```

<210> SEQ ID NO 30
<211> LENGTH: 94
<212> TYPE: PRT
<213> ORGANISM: Homo Sapiens

<400> SEQUENCE: 30

Ser Ser Gly Pro Thr Gln Val Pro Ala Val Ser Val Ala Leu Gly Gln
1 5 10 15

Met Ala Arg Ile Thr Cys Gln Gly Asp Ser Met Glu Gly Ser Tyr Glu
20 25 30

His Trp Tyr Gln Gln Lys Pro Gly Gln Ala Pro Val Leu Val Ile Tyr
35 40 45

Asp Ser Ser Asp Arg Pro Ser Arg Ile Pro Glu Arg Phe Ser Gly Ser
50 55 60

Lys Ser Gly Asn Thr Thr Thr Leu Thr Ile Thr Gly Ala Gln Ala Glu
65 70 75 80

Asp Glu Ala Asp Tyr Tyr Tyr Gln Leu Ile Asp Asn His Ala
85 90

<210> SEQ ID NO 31
<211> LENGTH: 103
<212> TYPE: PRT
<213> ORGANISM: Homo Sapiens

<400> SEQUENCE: 31

Leu Pro Val Leu Thr Gln Pro Pro Ser Ala Ser Ala Leu Leu Gly Ala
1 5 10 15

Ser Ile Lys Leu Thr Cys Thr Leu Ser Ser Glu His Ser Thr Tyr Thr
20 25 30

Ile Glu Trp Tyr Gln Gln Arg Pro Gly Arg Ser Pro Gln Tyr Ile Met
35 40 45

Lys Val Lys Ser Asp Gly Ser His Ser Lys Gly Asp Gly Ile Pro Asp
50 55 60

Arg Phe Met Gly Ser Ser Ser Gly Ala Asp Arg Tyr Leu Thr Phe Ser
65 70 75 80

Asn Leu Gln Ser Asp Asp Glu Ala Glu Tyr His Cys Gly Glu Ser His
85 90 95

Thr Ile Asp Gly Gln Val Gly
100

<210> SEQ ID NO 32
<211> LENGTH: 99
<212> TYPE: PRT
<213> ORGANISM: Homo Sapiens

<400> SEQUENCE: 32

Gln Pro Val Leu Thr Gln Ser Ser Ser Ala Ser Ala Ser Leu Gly Ser
1 5 10 15

Ser Val Lys Leu Thr Cys Thr Leu Ser Ser Gly His Ser Ser Tyr Ile
20 25 30

Ile Ala Trp His Gln Gln Gln Pro Gly Lys Ala Pro Arg Tyr Leu Met
35 40 45

Lys Leu Glu Gly Ser Gly Ser Tyr Asn Lys Gly Ser Gly Val Pro Asp
50 55 60

Arg Phe Ser Gly Ser Ser Ser Gly Ala Asp Arg Tyr Leu Thr Ile Ser
65 70 75 80

Asn Leu Gln Leu Glu Asp Glu Ala Asp Tyr Tyr Cys Glu Thr Trp Asp

```
                85                  90                  95

Ser Asn Thr


<210> SEQ ID NO 33
<211> LENGTH: 99
<212> TYPE: PRT
<213> ORGANISM: Homo Sapiens

<400> SEQUENCE: 33

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gly His Ser Ser Tyr Ala
            20                  25                  30

Ile Ala Trp His Gln Gln Gln Pro Glu Lys Gly Pro Arg Tyr Leu Met
        35                  40                  45

Lys Leu Asn Ser Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gln Thr Trp Gly
                85                  90                  95

Thr Gly Ile


<210> SEQ ID NO 34
<211> LENGTH: 104
<212> TYPE: PRT
<213> ORGANISM: Homo Sapiens

<400> SEQUENCE: 34

Gln Pro Val Leu Thr Gln Pro Pro Ser Ser Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser Asp Lys Gly Gln Gly Ser Gly Val
    50                  55                  60

Pro Ser Arg Phe Ser Gly Ser Lys Asp Ala Ser Ala Asn Thr Gly Ile
65                  70                  75                  80

Leu Leu Ile Ser Gly Leu Gln Ser Glu Asp Glu Ala Asp Tyr Tyr Cys
                85                  90                  95

Met Ile Trp Pro Ser Asn Ala Ser
            100


<210> SEQ ID NO 35
<211> LENGTH: 104
<212> TYPE: PRT
<213> ORGANISM: Homo Sapiens

<400> SEQUENCE: 35

Gln Pro Val Leu Thr Gln Pro Thr Ser Leu Ser Ala Ser Pro Gly Ala
1               5                   10                  15

Ser Ala Arg Phe Thr Cys Thr Leu Arg Ser Gly Ile Asn Val Gly Thr
            20                  25                  30

Tyr Arg Ile Tyr Trp Tyr Gln Gln Lys Pro Gly Ser Leu Pro Arg Tyr
        35                  40                  45

Leu Leu Arg Tyr Lys Ser Asp Ser Asp Lys Gln Gln Gly Ser Gly Val
```

```
    50                  55                  60

Pro Ser Arg Phe Ser Gly Ser Lys Asp Ala Ser Thr Asn Ala Gly Leu
65                  70                  75                  80

Leu Leu Ile Ser Gly Leu Gln Ser Glu Asp Glu Ala Asp Tyr Tyr Cys
                85                  90                  95

Ala Ile Trp Tyr Ser Ser Thr Ser
            100


<210> SEQ ID NO 36
<211> LENGTH: 104
<212> TYPE: PRT
<213> ORGANISM: Homo Sapiens

<400> SEQUENCE: 36

Gln Ala Val Leu Thr Gln Pro Ala Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Ser
            100


<210> SEQ ID NO 37
<211> LENGTH: 104
<212> TYPE: PRT
<213> ORGANISM: Homo Sapiens

<400> SEQUENCE: 37

Gln Pro Val Leu Thr Gln Pro Thr Ser Leu Ser Ala Ser Pro Gly Ala
1               5                   10                  15

Ser Ala Arg Leu Thr Cys Thr Leu Arg Ser Gly Ile Asn Leu Gly Ser
            20                  25                  30

Tyr Arg Ile Phe Trp Tyr Gln Gln Lys Pro Glu Ser Pro Pro Arg Tyr
        35                  40                  45

Leu Leu Ser Tyr Tyr Ser Asp Ser Ser Lys His Gln Gly Ser Gly Val
    50                  55                  60

Pro Ser Arg Phe Ser Gly Ser Lys Asp Ala Ser Ser Asn Ala Gly Ile
65                  70                  75                  80

Leu Val Ile Ser Gly Leu Gln Ser Glu Asp Glu Ala Asp Tyr Tyr Cys
                85                  90                  95

Met Ile Trp His Ser Ser Ala Ser
            100


<210> SEQ ID NO 38
<211> LENGTH: 105
<212> TYPE: PRT
<213> ORGANISM: Homo Sapiens

<400> SEQUENCE: 38

Gln Pro Val Leu Thr Gln Pro Ser Ser His Ser Ala Ser Ser Gly Ala
1               5                   10                  15
```

```
Ser Val Arg Leu Thr Cys Met Leu Ser Ser Gly Phe Ser Val Gly Asp
            20                  25                  30

Phe Trp Ile Arg Trp Tyr Gln Gln Lys Pro Gly Asn Pro Pro Arg Tyr
        35                  40                  45

Leu Leu Tyr Tyr His Ser Asp Ser Asn Lys Gly Gln Gly Ser Gly Val
    50                  55                  60

Pro Ser Arg Phe Ser Gly Ser Asn Asp Ala Ser Ala Asn Ala Gly Ile
65                  70                  75                  80

Leu Arg Ile Ser Gly Leu Gln Pro Glu Asp Glu Ala Asp Tyr Tyr Cys
                85                  90                  95

Gly Thr Trp His Ser Asn Ser Lys Thr
            100                 105


<210> SEQ ID NO 39
<211> LENGTH: 98
<212> TYPE: PRT
<213> ORGANISM: Homo Sapiens

<400> SEQUENCE: 39

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn


<210> SEQ ID NO 40
<211> LENGTH: 98
<212> TYPE: PRT
<213> ORGANISM: Homo Sapiens

<400> SEQUENCE: 40

Gln Thr Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Tyr Tyr Pro Asn Trp Phe Gln Gln Lys Pro Gly Gln Ala Pro Arg Ala
        35                  40                  45

Leu Ile Tyr Ser Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Tyr Tyr Gly Gly
                85                  90                  95

Ala Gln


<210> SEQ ID NO 41
<211> LENGTH: 98
<212> TYPE: PRT
```

<213> ORGANISM: Homo Sapiens

<400> SEQUENCE: 41

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Ala Pro Arg Thr
        35                  40                  45

Leu Ile Tyr Asp Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Ser Tyr Ser Gly
                85                  90                  95

Ala Arg
```

<210> SEQ ID NO 42
<211> LENGTH: 98
<212> TYPE: PRT
<213> ORGANISM: Homo Sapiens

<400> SEQUENCE: 42

```
Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile
```

<210> SEQ ID NO 43
<211> LENGTH: 104
<212> TYPE: PRT
<213> ORGANISM: Homo Sapiens

<400> SEQUENCE: 43

```
Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Val Met
        35                  40                  45

Arg Val Gly Thr Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Ser Asn Phe Val
```

```
            100


<210> SEQ ID NO 44
<211> LENGTH: 98
<212> TYPE: PRT
<213> ORGANISM: Homo Sapiens

<400> SEQUENCE: 44

Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Leu Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95

Ser Ala


<210> SEQ ID NO 45
<211> LENGTH: 104
<212> TYPE: PRT
<213> ORGANISM: Homo Sapiens

<400> SEQUENCE: 45

Arg Pro Val Leu Thr Gln Pro Pro Ser Leu Ser Ala Ser Pro Gly Ala
1               5                   10                  15

Thr Ala Arg Leu Pro Cys Thr Leu Ser Ser Asp Leu Ser Val Gly Gly
            20                  25                  30

Lys Asn Met Phe Trp Tyr Gln Gln Lys Pro Gly Ser Ser Pro Arg Leu
        35                  40                  45

Phe Leu Tyr His Tyr Ser Asp Ser Asp Lys Gln Leu Gly Pro Gly Val
    50                  55                  60

Pro Ser Arg Val Ser Gly Ser Lys Glu Thr Ser Ser Asn Thr Ala Phe
65                  70                  75                  80

Leu Leu Ile Ser Gly Leu Gln Pro Glu Asp Glu Ala Asp Tyr Tyr Cys
                85                  90                  95

Gln Val Tyr Glu Ser Ser Ala Asn
            100


<210> SEQ ID NO 46
<211> LENGTH: 14
<212> TYPE: PRT
<213> ORGANISM: Homo Sapiens

<400> SEQUENCE: 46

Gln Ser Val Leu Thr Gln Pro Pro Ser Val Ser Glu Ala Pro
1               5                   10


<210> SEQ ID NO 47
<211> LENGTH: 11
<212> TYPE: PRT
<213> ORGANISM: Homo Sapiens

<400> SEQUENCE: 47

Arg Gln Arg Val Thr Ile Ser Cys Ser Gly Ser
```

1 5 10

<210> SEQ ID NO 48
<211> LENGTH: 8
<212> TYPE: PRT
<213> ORGANISM: Homo Sapiens

<400> SEQUENCE: 48

Ser Ser Asn Ile Gly Asn Asn Ala
1 5

<210> SEQ ID NO 49
<211> LENGTH: 8
<212> TYPE: PRT
<213> ORGANISM: Homo Sapiens

<400> SEQUENCE: 49

Val Asn Trp Tyr Gln Gln Leu Pro
1 5

<210> SEQ ID NO 50
<211> LENGTH: 9
<212> TYPE: PRT
<213> ORGANISM: Homo Sapiens

<400> SEQUENCE: 50

Gly Lys Ala Pro Lys Leu Leu Ile Tyr
1 5

<210> SEQ ID NO 51
<211> LENGTH: 8
<212> TYPE: PRT
<213> ORGANISM: Homo Sapiens

<400> SEQUENCE: 51

Leu Leu Pro Ser Gly Val Ser Asp
1 5

<210> SEQ ID NO 52
<211> LENGTH: 8
<212> TYPE: PRT
<213> ORGANISM: Homo Sapiens

<400> SEQUENCE: 52

Arg Phe Ser Gly Ser Lys Ser Gly
1 5

<210> SEQ ID NO 53
<211> LENGTH: 12
<212> TYPE: PRT
<213> ORGANISM: Homo Sapiens

<400> SEQUENCE: 53

Thr Ser Ala Ser Leu Ala Ile Ser Gly Leu Gln Ser
1 5 10

<210> SEQ ID NO 54
<211> LENGTH: 8
<212> TYPE: PRT
<213> ORGANISM: Homo Sapiens

<400> SEQUENCE: 54

Glu Asp Glu Ala Asp Tyr Tyr Cys
1 5

<210> SEQ ID NO 55
<211> LENGTH: 9
<212> TYPE: PRT
<213> ORGANISM: Homo Sapiens

<400> SEQUENCE: 55

Ala Ala Trp Asp Asp Ser Leu Asn Gly
1 5

<210> SEQ ID NO 56
<211> LENGTH: 290
<212> TYPE: DNA
<213> ORGANISM: Homo Sapiens

<400> SEQUENCE: 56
tcctatgtgc tgactcagcc accctcagtg tcagtggccc caggaaagac ggccaggatt 60
acctgtgggg gaaacaacat tggaagtaaa agtgtgcact ggtaccagca gaagccaggc 120
caggcccctg tgctggtcat ctattatgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgatcatcc 290

<210> SEQ ID NO 57
<211> LENGTH: 290
<212> TYPE: DNA
<213> ORGANISM: Homo Sapiens

<400> SEQUENCE: 57
tcctatgtgc tgactcagcc accctcagtg tcagtggccc caggaaagac ggccaggatt 60
acctgtgggg gaaacaacat tggaagtaaa agtgtgcact ggtaccagca gaagccaggc 120
caggcccctg tgctggtcat ctattatgat agcgaccggc cctcagggat ccctgagcga 180
ttctctggct ccaactctgg gaacacggcc accctgacca tcagcagggt cgaagccggg 240
gatgaggccg actattactg tcaggtgtgg gacagtagta gtgatcatcc 290

<210> SEQ ID NO 58
<211> LENGTH: 290
<212> TYPE: DNA
<213> ORGANISM: Homo Sapiens

<400> SEQUENCE: 58
tcctatgtgc tgactcagcc accctcggtg tcagtggccc caggacagac ggccaggatt 60
acctgtgggg gaaacaacat tggaagtaaa agtgtgcact ggtaccagca gaagccaggc 120
caggcccctg tgctggtcgt ctatgatgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgatcatcc 290

<210> SEQ ID NO 59
<211> LENGTH: 290
<212> TYPE: DNA
<213> ORGANISM: Homo Sapiens

<400> SEQUENCE: 59
tcctatgtgc tgactcagcc accctcggtg tcagtggccc caggaaagac ggccaggatt 60
acctgtgggg gaaacaacat tggaagtaaa agtgtgcact ggtaccagca gaagccaggc 120
caggcccctg tgctggtcgt ctatgatgat agcgaccggc cctcagggat ccctgagcga 180

```
ttctctggct ccaactctgg gaacacggcc accctgacca tcagcagggt cgaagccggg    240

gatgaggccg actattactg tcaggtgtgg gatagtagta gtgatcatcc               290


<210> SEQ ID NO 60
<211> LENGTH: 19
<212> TYPE: PRT
<213> ORGANISM: Homo Sapiens

<400> SEQUENCE: 60

Met Ala Trp Thr Ala Leu Leu Leu Gly Leu Leu Ser His Cys Thr Gly
1               5                   10                  15

Ser Val Thr


<210> SEQ ID NO 61
<211> LENGTH: 57
<212> TYPE: DNA
<213> ORGANISM: Homo Sapiens

<400> SEQUENCE: 61

atggcctgga ccgctctcct cctcggcctc ctctctcact gcacaggctc tgtgacc        57


<210> SEQ ID NO 62
<211> LENGTH: 20
<212> TYPE: PRT
<213> ORGANISM: Mus Musculus

<400> SEQUENCE: 62

Met Ser Val Pro Thr Gln Val Leu Gly Leu Leu Leu Leu Trp Leu Thr
1               5                   10                  15

Asp Ala Arg Cys
            20


<210> SEQ ID NO 63
<211> LENGTH: 60
<212> TYPE: DNA
<213> ORGANISM: Mus Musculus

<400> SEQUENCE: 63

atgagtgtgc ccactcaggt cctggggttg ctgctgctgt ggcttacaga tgccagatgt     60


<210> SEQ ID NO 64
<211> LENGTH: 60
<212> TYPE: DNA
<213> ORGANISM: Artificial Sequence
<220> FEATURE:
<223> OTHER INFORMATION: nucleotide sequence encoding mouse kappa light
      chain signal peptide, codon-optimised for CHO

<400> SEQUENCE: 64

atgtctgtgc ctacacaggt tctgggactg ctgctgctgt ggctgaccga cgccagatgt     60


<210> SEQ ID NO 65
<211> LENGTH: 381
<212> TYPE: DNA
<213> ORGANISM: Artificial Sequence
<220> FEATURE:
<223> OTHER INFORMATION: nucleic acid encoding 0325L VL domain with
      signal peptide

<400> SEQUENCE: 65

atgtctgtgc ctacacaggt tctgggactg ctgctgctgt ggctgaccga cgccagatgt     60

tacgtgctga cccagcctcc ttccgtgtct gttgctcctg gcgagacagc cagaatcacc    120
```

```
tgtggcggcg ataacatcgg ccggaagtcc gtgtactggt atcagcagaa gtccggccag    180

gctcctgtgc tggtcatcta ctacgactcc gaccggcctt ctggcatccc tgagagattc    240

tccggctcca actccggcaa taccgccaca ctgaccatct ccagagtgga agctggcgac    300

gaggccgact actactgcca agtgtgggac ggctcctctg accactgggt tttcggcgga    360

ggcaccaagc tgacagtgct g                                              381


<210> SEQ ID NO 66
<211> LENGTH: 127
<212> TYPE: PRT
<213> ORGANISM: Artificial Sequence
<220> FEATURE:
<223> OTHER INFORMATION: 0325L with mouse kappa signal peptide

<400> SEQUENCE: 66

Met Ser Val Pro Thr Gln Val Leu Gly Leu Leu Leu Leu Trp Leu Thr
1               5                   10                  15

Asp Ala Arg Cys Tyr Val Leu Thr Gln Pro Pro Ser Val Ser Val Ala
            20                  25                  30

Pro Gly Glu Thr Ala Arg Ile Thr Cys Gly Gly Asp Asn Ile Gly Arg
        35                  40                  45

Lys Ser Val Tyr Trp Tyr Gln Gln Lys Ser Gly Gln Ala Pro Val Leu
    50                  55                  60

Val Ile Tyr Tyr Asp Ser Asp Arg Pro Ser Gly Ile Pro Glu Arg Phe
65                  70                  75                  80

Ser Gly Ser Asn Ser Gly Asn Thr Ala Thr Leu Thr Ile Ser Arg Val
                85                  90                  95

Glu Ala Gly Asp Glu Ala Asp Tyr Tyr Cys Gln Val Trp Asp Gly Ser
            100                 105                 110

Ser Asp His Trp Val Phe Gly Gly Gly Thr Lys Leu Thr Val Leu
        115                 120                 125


<210> SEQ ID NO 67
<211> LENGTH: 233
<212> TYPE: PRT
<213> ORGANISM: Artificial Sequence
<220> FEATURE:
<223> OTHER INFORMATION: Lambda light chain comprising 0325L VL domain
      with mouse kappa signal peptide

<400> SEQUENCE: 67

Met Ser Val Pro Thr Gln Val Leu Gly Leu Leu Leu Leu Trp Leu Thr
1               5                   10                  15

Asp Ala Arg Cys Tyr Val Leu Thr Gln Pro Pro Ser Val Ser Val Ala
            20                  25                  30

Pro Gly Glu Thr Ala Arg Ile Thr Cys Gly Gly Asp Asn Ile Gly Arg
        35                  40                  45

Lys Ser Val Tyr Trp Tyr Gln Gln Lys Ser Gly Gln Ala Pro Val Leu
    50                  55                  60

Val Ile Tyr Tyr Asp Ser Asp Arg Pro Ser Gly Ile Pro Glu Arg Phe
65                  70                  75                  80

Ser Gly Ser Asn Ser Gly Asn Thr Ala Thr Leu Thr Ile Ser Arg Val
                85                  90                  95

Glu Ala Gly Asp Glu Ala Asp Tyr Tyr Cys Gln Val Trp Asp Gly Ser
            100                 105                 110

Ser Asp His Trp Val Phe Gly Gly Gly Thr Lys Leu Thr Val Leu Gly
        115                 120                 125
```

```
Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Lys Ser Tyr Ser Cys Gln Val Thr His Glu Gly Ser Thr Val Glu
    210                 215                 220

Lys Thr Val Ala Pro Thr Glu Cys Ser
225                 230


<210> SEQ ID NO 68
<211> LENGTH: 128
<212> TYPE: PRT
<213> ORGANISM: Artificial Sequence
<220> FEATURE:
<223> OTHER INFORMATION: 0128L VL domain with mouse kappa signal peptide

<400> SEQUENCE: 68

Met Ser Val Pro Thr Gln Val Leu Gly Leu Leu Leu Leu Trp Leu Thr
1               5                   10                  15

Asp Ala Arg Cys Ser Tyr Val Leu Thr Gln Pro Pro Ser Val Ser Val
            20                  25                  30

Ala Pro Gly Glu Thr Ala Arg Ile Thr Cys Gly Gly Asp Asn Ile Gly
        35                  40                  45

Arg Lys Ser Val Tyr Trp Tyr Gln Gln Lys Ser Gly Gln Ala Pro Val
    50                  55                  60

Leu Val Ile Tyr Tyr Asp Ser Asp Arg Pro Ser Gly Ile Pro Glu Arg
65                  70                  75                  80

Phe Ser Gly Ser Asn Ser Gly Asn Thr Ala Thr Leu Thr Ile Ser Arg
                85                  90                  95

Val Glu Ala Gly Asp Glu Ala Asp Tyr Tyr Cys Gln Val Trp Asp Gly
            100                 105                 110

Ser Ser Asp His Trp Val Phe Gly Gly Gly Thr Lys Leu Thr Val Leu
        115                 120                 125


<210> SEQ ID NO 69
<211> LENGTH: 18
<212> TYPE: PRT
<213> ORGANISM: Artificial Sequence
<220> FEATURE:
<223> OTHER INFORMATION: V12 signal peptide derived from Sandfly Yellow
      related protein

<400> SEQUENCE: 69

Met Arg Phe Phe Phe Val Phe Leu Ala Ile Val Leu Phe Gln Gly Ile
1               5                   10                  15

His Gly


<210> SEQ ID NO 70
<211> LENGTH: 15
<212> TYPE: PRT
<213> ORGANISM: Artificial Sequence
<220> FEATURE:
<223> OTHER INFORMATION: V14 signal peptide derived from Silkworm
      Fibroin LC
```

<400> SEQUENCE: 70

Met Lys Pro Ile Phe Leu Val Leu Leu Trp Thr Ser Ala Tyr Ala
1 5 10 15

<210> SEQ ID NO 71
<211> LENGTH: 16
<212> TYPE: PRT
<213> ORGANISM: Artificial Sequence
<220> FEATURE:
<223> OTHER INFORMATION: V16 signal peptide derived from Snake PLA2

<400> SEQUENCE: 71

Met Arg Thr Leu Trp Ile Met Ala Val Leu Leu Leu Gly Val Glu Gly
1 5 10 15

<210> SEQ ID NO 72
<211> LENGTH: 18
<212> TYPE: PRT
<213> ORGANISM: Artificial Sequence
<220> FEATURE:
<223> OTHER INFORMATION: V17 signal peptide derived from Cypridina Noctiluca luciferase

<400> SEQUENCE: 72

Met Lys Thr Leu Ile Leu Ala Val Ala Leu Val Tyr Cys Ala Thr Val
1 5 10 15

His Cys

<210> SEQ ID NO 73
<211> LENGTH: 17
<212> TYPE: PRT
<213> ORGANISM: Artificial Sequence
<220> FEATURE:
<223> OTHER INFORMATION: V19 signal peptide derived from Pinemoth Fibroin LC

<400> SEQUENCE: 73

Met Met Arg Pro Ile Val Leu Val Leu Leu Phe Ala Thr Ser Ala Leu
1 5 10 15

Ala

<210> SEQ ID NO 74
<211> LENGTH: 19
<212> TYPE: PRT
<213> ORGANISM: Mus Musculus

<400> SEQUENCE: 74

Met Gly Trp Ser Cys Ile Ile Leu Phe Leu Val Ala Thr Ala Thr Gly
1 5 10 15

Val His Ser

<210> SEQ ID NO 75
<211> LENGTH: 15
<212> TYPE: PRT
<213> ORGANISM: Homo Sapiens

<400> SEQUENCE: 75

Ala Trp Thr Pro Leu Leu Leu Pro Leu Leu Thr Leu Cys Thr Ser
1 5 10 15

<210> SEQ ID NO 76
<211> LENGTH: 19
<212> TYPE: PRT

```
<213> ORGANISM: Homo Sapiens

<400> SEQUENCE: 76

Met Ala Gly Phe Pro Leu Leu Leu Thr Leu Leu Thr His Cys Ala Gly
1               5                   10                  15

Ser Trp Ala


<210> SEQ ID NO 77
<211> LENGTH: 22
<212> TYPE: PRT
<213> ORGANISM: Homo Sapiens

<400> SEQUENCE: 77

Met Asp Met Arg Val Pro Ala Gln Leu Leu Gly Leu Leu Leu Leu Trp
1               5                   10                  15

Leu Pro Gly Ala Lys Cys
            20


<210> SEQ ID NO 78
<211> LENGTH: 366
<212> TYPE: DNA
<213> ORGANISM: Homo Sapiens

<400> SEQUENCE: 78

gaggtgcagc tggtggagtc tgggggaggc tttgtccagc ctggggggtc cctgagactc     60

tcctgtgcag tctctggatt cagatttaat agctattgga tgagctgggt ccgccaggct    120

ccagggaagg ggctggagtg ggtggccaac ataaaccaag atggaagtag aaaattctat    180

gtggcctctg tgaagggccg attcaccatg tccagagaca acgccaagaa atcagtgtat    240

gtacaaatga acagcctgag agccgaggac acggctgtgt attactgtgc gagagagggg    300

tatagtagta tcaagtatta tggtatggac gtctggggcc aagggaccac ggtcaccgtc    360

tcctca                                                               366


<210> SEQ ID NO 79
<211> LENGTH: 122
<212> TYPE: PRT
<213> ORGANISM: Homo Sapiens

<400> SEQUENCE: 79

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Arg Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Arg Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ile Lys Tyr Tyr Gly Met Asp Val Trp
            100                 105                 110

Gly Gln Gly Thr Thr Val Thr Val Ser Ser
        115                 120


<210> SEQ ID NO 80
```

<211> LENGTH: 1341
<212> TYPE: DNA
<213> ORGANISM: Artificial Sequence
<220> FEATURE:
<223> OTHER INFORMATION: Nucleic acid encoding N1280H-IgG4-P K439E heavy chain; N1280 coding sequence underlined

<400> SEQUENCE: 80

```
gaagtgcagc tggttgaatc tggcggcgga tttgttcagc ctggcggctc tctgagactg     60
tcctgtgctg tgtccggctt ccggttcaac tcctactgga tgtcctgggt ccgacaggct    120
cctggcaaag gactggaatg ggtcgccaac atcaaccagg acggctcccg gaagttctac    180
gtggcctctg tgaagggcag attcaccatg tctcgggaca acgccaagaa atccgtgtac    240
gtgcagatga actccctgag agccgaggac accgccgtgt actactgtgc tagagagggc    300
tactcctcca tcaagtacta cggcatggac gtgtggggcc agggcacaac cgtgacagtc    360
tcttccgctt ccaccaaggg acccagcgtt ttccctctgg ctccttgctc cagatccacc    420
tccgagtcta cagctgctct gggctgcctg gtcaaggact actttcctga gcctgtgacc    480
gtgtcctgga actctggcgc tctgacatct ggcgtgcaca cctttccagc tgtgctgcag    540
tcctccggcc tgtactctct gtcctctgtc gtgaccgtgc cttccagctc tctgggaacc    600
cagacctaca cctgtaatgt ggaccacaag ccttccaaca ccaaggtgga caagcgcgtg    660
gaatctaagt acggccctcc ttgtcctcca tgtcctgctc cagagtttct cggcggaccc    720
tccgtgtttc tgttccctcc aaagcctaag gacaccctga tgatctctcg gacccctgaa    780
gtgacctgcg tggtggtgga tgtgtcccaa gaggatcccg aggtgcagtt caattggtac    840
gtggacggcg tggaagtgca caatgccaag accaagccta gagaggaaca gtacaactcc    900
acctacagag tggtgtccgt gctgaccgtg ctgcaccagg attggctgaa cggcaaagag    960
tacaagtgca aggtgtccaa caagggcctg cctagctcca tcgaaaagac catctccaag   1020
gccaagggcc agcctcgaga accccaggtt tacaccctgc ctccaagcca agaggaaatg   1080
accaagaacc aggtgtccct gacctgtctc gtgaagggct tctacccctc cgatatcgcc   1140
gtggaatggg agtctaatgg ccagccagag aacaactaca agaccacacc tccagtgctg   1200
gactccgacg gctcattctt tctgtactcc aagctgacag tggacaagtc ccggtggcaa   1260
gagggcaacg tgttctcctg ctctgtgatg cacgaggccc tgcacaacca ctacacccaa   1320
gagtccctgt ctctgtcccc t                                              1341
```

<210> SEQ ID NO 81
<211> LENGTH: 447
<212> TYPE: PRT
<213> ORGANISM: Artificial Sequence
<220> FEATURE:
<223> OTHER INFORMATION: N1280H-IgG4-P K439E amino acid sequence

<400> SEQUENCE: 81

```
Glu Val Gln Leu Val Glu Ser Gly Gly Gly Phe Val Gln Pro Gly Gly
1               5                   10                  15

Ser Leu Arg Leu Ser Cys Ala Val Ser Gly Phe Arg Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Arg Lys Phe Tyr Val Ala Ser Val
    50                  55                  60

Lys Gly Arg Phe Thr Met Ser Arg Asp Asn Ala Lys Lys Ser Val Tyr
65                  70                  75                  80
```

```
Val Gln Met Asn Ser Leu Arg Ala Glu Asp Thr Ala Val Tyr Tyr Cys
                85                  90                  95

Ala Arg Glu Gly Tyr Ser Ser Ile Lys Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Glu Ser Leu Ser Leu Ser Pro
        435                 440                 445
```

<210> SEQ ID NO 82
<211> LENGTH: 366
<212> TYPE: DNA
<213> ORGANISM: Homo Sapiens

<400> SEQUENCE: 82

```
gaggtgcagc tggttgaatc tggcggcgga tttgttcagc ctggcggctc tctgagactg     60
```

agctgtgccg tgtccggctt ccggttcaac agctactgga tgtcctgggt ccgacaggcc 120
cctggcaaag gacttgagtg ggtcgccaac atcaaccagg acggcagccg gaagttttac 180
gtggcctctg tgaagggcag attcaccatg agccgggaca acgccgacaa aagcgtgtac 240
gtgcagatga acagcctgag agccgaggac accgccgtgt actattgtgc cagagagggc 300
tacagcagca tcaagtacta cggcatggac gtgtggggcc agggcacaac agtgacagtc 360
tcttct 366

<210> SEQ ID NO 83
<211> LENGTH: 122
<212> TYPE: PRT
<213> ORGANISM: Homo Sapiens

<400> SEQUENCE: 83

Glu Val Gln Leu Val Glu Ser Gly Gly Gly Phe Val Gln Pro Gly Gly
1 5 10 15

Ser Leu Arg Leu Ser Cys Ala Val Ser Gly Phe Arg Phe Asn Ser Tyr
20 25 30

Trp Met Ser Trp Val Arg Gln Ala Pro Gly Lys Gly Leu Glu Trp Val
35 40 45

Ala Asn Ile Asn Gln Asp Gly Ser Arg Lys Phe Tyr Val Ala Ser Val
50 55 60

Lys Gly Arg Phe Thr Met Ser Arg Asp Asn Ala Asp Lys Ser Val Tyr
65 70 75 80

Val Gln Met Asn Ser Leu Arg Ala Glu Asp Thr Ala Val Tyr Tyr Cys
85 90 95

Ala Arg Glu Gly Tyr Ser Ser Ile Lys Tyr Tyr Gly Met Asp Val Trp
100 105 110

Gly Gln Gly Thr Thr Val Thr Val Ser Ser
115 120

<210> SEQ ID NO 84
<211> LENGTH: 1341
<212> TYPE: DNA
<213> ORGANISM: Artificial Sequence
<220> FEATURE:
<223> OTHER INFORMATION: Nucleic acid encoding N1441H-IgG4-P K439E heavy chain

<400> SEQUENCE: 84
gaagtgcagc tggttgaatc tggcggcgga tttgttcagc ctggcggctc tctgagactg 60
tcctgtgctg tgtccggctt ccggttcaac tcctactgga tgtcctgggt ccgacaggct 120
cctggcaaag gactggaatg ggtcgccaac atcaaccagg acggctcccg gaagttctac 180
gtggcctctg tgaagggcag attcaccatg tctcgggaca acgccgacaa gtccgtgtac 240
gtgcagatga actccctgag agccgaggac accgccgtgt actactgtgc tagagagggc 300
tactcctcca tcaagtacta cggcatggac gtgtggggcc agggcacaac cgtgacagtc 360
tcttccgctt ccaccaaggg acccagcgtt ttccctctgg ctccttgctc cagatccacc 420
tccgagtcta cagctgctct gggctgcctg gtcaaggact actttcctga gcctgtgacc 480
gtgtcctgga actctggcgc tctgacatct ggcgtgcaca cctttccagc tgtgctgcag 540
tcctccggcc tgtactctct gtcctctgtc gtgaccgtgc cttccagctc tctgggaacc 600
cagacctaca cctgtaatgt ggaccacaag ccttccaaca ccaaggtgga caagcgcgtg 660
gaatctaagt acggccctcc ttgtcctcca tgtcctgctc cagagtttct cggcggaccc 720

```
tccgtgtttc tgttccctcc aaagcctaag gacaccctga tgatctctcg gacccctgaa    780

gtgacctgcg tggtggtgga tgtgtcccaa gaggatcccg aggtgcagtt caattggtac    840

gtggacggcg tggaagtgca caacgccaag accaagccta gagaggaaca gtacaactcc    900

acctacagag tggtgtccgt gctgaccgtg ctgcaccagg attggctgaa cggcaaagag    960

tacaagtgca aggtgtccaa caagggcctg cctagctcca tcgaaaagac catctccaag   1020

gccaagggcc agcctcgaga accccaggtt tacaccctgc ctccaagcca agaggaaatg   1080

accaagaacc aggtgtccct gacctgtctc gtgaagggct tctacccctc cgatatcgcc   1140

gtggaatggg agtctaatgg ccagccagag aacaactaca agaccacacc tccagtgctg   1200

gactccgacg gctcattctt tctgtactcc aagctgacag tggacaagtc ccggtggcaa   1260

gagggcaacg tgttctcctg ctctgtgatg cacgaggccc tgcacaacca ctacacccaa   1320

gagtccctgt ctctgtcccc t                                              1341
```

<210> SEQ ID NO 85
<211> LENGTH: 447
<212> TYPE: PRT
<213> ORGANISM: Artificial Sequence
<220> FEATURE:
<223> OTHER INFORMATION: N1441H-IgG4-P K439E amino acid sequence

<400> SEQUENCE: 85

```
Glu Val Gln Leu Val Glu Ser Gly Gly Gly Phe Val Gln Pro Gly Gly
1               5                   10                  15

Ser Leu Arg Leu Ser Cys Ala Val Ser Gly Phe Arg Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Arg Lys Phe Tyr Val Ala Ser Val
    50                  55                  60

Lys Gly Arg Phe Thr Met Ser Arg Asp Asn Ala Asp Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ile Lys Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
```

```
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 86
<211> LENGTH: 363
<212> TYPE: DNA
<213> ORGANISM: Homo Sapiens

<400> SEQUENCE: 86

caggttcagc tgattcagtc cggcgccaaa gtgaagaaac ctggcgcctc tgtgaaggtg      60

tcctgcaagg cctctcggta caagttcacc tcctactaca tgcactgggt ccgacaggcc     120

cctggacaag gattggagtg gatgggcatc atcaacccca agtccggctc cacctcttac     180

gcccagaaat tccagggcag agtgaccatg accagagaca cctctacctc caccgtgtac     240

atggaactgt ccagcctgag atccgaggac accgccgtgt actactgtgc cagagatggc     300

tacggcagct tctccagact gatccagttg tggggccagg gcacactggt cacagtgtcc     360

tct                                                                   363


<210> SEQ ID NO 87
<211> LENGTH: 121
<212> TYPE: PRT
<213> ORGANISM: Homo Sapiens

<400> SEQUENCE: 87

Gln Val Gln Leu Ile Gln Ser Gly Ala Lys Val Lys Lys Pro Gly Ala
1               5                   10                  15

Ser Val Lys Val Ser Cys Lys Ala Ser Arg Tyr Lys Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60
```

```
Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Leu Ile Gln Leu Trp Gly
            100                 105                 110

Gln Gly Thr Leu Val Thr Val Ser Ser
        115                 120
```

<210> SEQ ID NO 88
<211> LENGTH: 1338
<212> TYPE: DNA
<213> ORGANISM: Artificial Sequence
<220> FEATURE:
<223> OTHER INFORMATION: Nucleic acid encoding T0999H-IgG4-P E356K heavy chain; T0999H coding sequence underlined

<400> SEQUENCE: 88

```
caggttcagc tgattcagtc cggcgccaaa gtgaagaaac ctggcgcctc tgtgaaggtg     60

tcctgcaagg cctctcggta caagttcacc tcctactaca tgcactgggt ccgacaggcc    120

cctggacaag gattggagtg gatgggcatc atcaacccca agtccggctc cacctcttac    180

gcccagaaat tccagggcag agtgaccatg accagagaca cctctacctc caccgtgtac    240

atggaactgt ccagcctgag atccgaggac accgccgtgt actactgtgc cagagatggc    300

tacggcagct tctccagact gatccagttg tggggccagg gcacactggt cacagtgtcc    360

tctgcttcca ccaagggacc cagcgtgttc cctctggctc cttgctccag atccacctcc    420

gagtctacag ctgctctggg ctgcctggtc aaggactact tcctgagcc tgtgaccgtg     480

tcttggaact ctggcgctct gacatctggc gtgcacacct ttccagctgt gctgcagtcc    540

tccggcctgt actctctgtc ctctgtcgtg accgtgcctt ccagctctct gggaacccag    600

acctacacct gtaatgtgga ccacaagcct tccaacacca aggtggacaa gcgcgtggaa    660

tctaagtacg gccctccttg tcctccatgt cctgctccag agtttctcgg cggaccctcc    720

gtgtttctgt tccctccaaa gcctaaggac accctgatga tctctcggac ccctgaagtg    780

acctgcgtgg tggtggatgt gtcccaagag gatcccgagg tgcagttcaa ttggtacgtg    840

gacggcgtgg aagtgcacaa cgccaagacc aagcctagag aggaacagta caactccacc    900

tacagagtgg tgtccgtgct gaccgtgctg caccaggatt ggctgaacgg caaagagtac    960

aagtgcaagg tgtccaacaa gggcctgcct agctccatcg aaaagaccat ctccaaggcc   1020

aagggccagc ctcgagaacc ccaggtttac accctgcctc caagccagaa agagatgacc   1080

aagaaccagg tgtccctgac ctgcctcgtg aagggcttct acccttccga tatcgccgtg   1140

gaatgggaga gcaatggcca gccagagaac aactacaaga ccacacctcc tgtgctggac   1200

tccgatggct cattctttct gtactccaag ctgacagtgg acaagtcccg gtggcaagag   1260

ggcaacgtgt tctcctgctc tgtgatgcac gaggccctgc acaaccacta cacccagaag   1320

tccctgtctc tgtcccct                                                 1338
```

<210> SEQ ID NO 89
<211> LENGTH: 446
<212> TYPE: PRT
<213> ORGANISM: Artificial Sequence
<220> FEATURE:
<223> OTHER INFORMATION: T0999H-IgG4-P E356K amino acid sequence

<400> SEQUENCE: 89

```
Gln Val Gln Leu Ile Gln Ser Gly Ala Lys Val Lys Lys Pro Gly Ala
1               5                   10                  15

Ser Val Lys Val Ser Cys Lys Ala Ser Arg Tyr Lys Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Leu Ile Gln Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Lys Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

```
Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Pro
        435                 440                 445


<210> SEQ ID NO 90
<211> LENGTH: 363
<212> TYPE: DNA
<213> ORGANISM: Homo Sapiens

<400> SEQUENCE: 90

caggtgcagt tgatacagtc tggggctgag gtgaagaagc ctggggcctc agtgaaggtt     60

tcctgcaagg catctagata cagcttcacc agctactata tgcactgggt gcgacaggcc    120

cctggacaag ggcttgagtg gatgggaata atcaacccta aaagtggtag tacaagttac    180

gcacagaagt tccagggcag agtcaccatg accagggaca cgtccacgag cacagtctac    240

atggagctga gcagcctgag atctgaggac acggccgtgt attactgtgc gagagatggg    300

tatggcagct cgtcccggtg cctccagctc tggggccagg gcaccctggt caccgtctcc    360

tca                                                                  363


<210> SEQ ID NO 91
<211> LENGTH: 121
<212> TYPE: PRT
<213> ORGANISM: Homo Sapiens

<400> SEQUENCE: 91

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Ser Arg Cys Leu Gln Leu Trp Gly
            100                 105                 110

Gln Gly Thr Leu Val Thr Val Ser Ser
        115                 120


<210> SEQ ID NO 92
<211> LENGTH: 363
<212> TYPE: DNA
<213> ORGANISM: Homo Sapiens

<400> SEQUENCE: 92

caggtgcagt tgatacagtc tggggctgag gtgaagaagc ctggggcctc agtgaaggtt     60

tcctgcaagg catctagata caagttcacc agctactata tgcactgggt gcgacaggcc    120

cctggacaag ggcttgagtg gatgggaata atcaacccta aaagtggtag tacaagttac    180

gcacagaagt tccagggcag agtcaccatg accagggaca cgtccacgag cacagtctac    240

atggagctga gcagcctgag atctgaggac acggccgtgt attactgtgc gagagatggg    300

tatggcagct tctcccggct gatccagctc tggggccagg gcaccctggt caccgtctcc    360
```

tca 363

<210> SEQ ID NO 93
<211> LENGTH: 121
<212> TYPE: PRT
<213> ORGANISM: Homo Sapiens

<400> SEQUENCE: 93

Gln Val Gln Leu Ile Gln Ser Gly Ala Glu Val Lys Lys Pro Gly Ala
1 5 10 15

Ser Val Lys Val Ser Cys Lys Ala Ser Arg Tyr Lys Phe Thr Ser Tyr
20 25 30

Tyr Met His Trp Val Arg Gln Ala Pro Gly Gln Gly Leu Glu Trp Met
35 40 45

Gly Ile Ile Asn Pro Lys Ser Gly Ser Thr Ser Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Asp Gly Tyr Gly Ser Phe Ser Arg Leu Ile Gln Leu Trp Gly
100 105 110

Gln Gly Thr Leu Val Thr Val Ser Ser
115 120

<210> SEQ ID NO 94
<211> LENGTH: 1338
<212> TYPE: DNA
<213> ORGANISM: Artificial Sequence
<220> FEATURE:
<223> OTHER INFORMATION: Nucleic acid encoding T0736H-IgG4-P E356K heavy chain

<400> SEQUENCE: 94
caggttcagc tgattcagtc tggcgccgaa gtgaagaaac ctggcgcctc tgtgaaggtg 60
tcctgcaagg cctctcggta caagttcacc tcctactaca tgcactgggt ccgacaggcc 120
cctggacaag gattggagtg gatgggcatc atcaacccca agtccggctc cacctcttac 180
gcccagaaat tccagggcag agtgaccatg accagagaca cctctacctc caccgtgtac 240
atggaactgt ccagcctgag atccgaggac accgccgtgt actactgtgc cagagatggc 300
tacggcagct tctccaggct gatccagttg tggggacagg gcacactggt caccgtgtcc 360
tctgcttcta ccaagggacc cagcgtgttc cctctggctc cttgctccag atccacctcc 420
gagtctacag ctgctctggg ctgcctggtc aaggactact ttcctgagcc tgtgaccgtg 480
tcttggaact ctggcgctct gacatctggc gtgcacacct ttccagctgt gctgcagtcc 540
tccggcctgt actctctgtc ctctgtcgtg accgtgcctt ccagctctct gggaacccag 600
acctacacct gtaatgtgga ccacaagcct tccaacacca aggtggacaa gcgcgtggaa 660
tctaagtacg gccctccttg tcctccatgt cctgctccag agtttctcgg cggaccctcc 720
gtgtttctgt tccctccaaa gcctaaggac accctgatga tctctcggac ccctgaagtg 780
acctgcgtgg tggtggatgt gtcccaagag gatcccgagg tgcagttcaa ttggtacgtg 840
gacggcgtgg aagtgcacaa cgccaagacc aagcctagag aggaacagta caactccacc 900
tacagagtgg tgtccgtgct gaccgtgctg caccaggatt ggctgaacgg caaagagtac 960
aagtgcaagg tgtccaacaa gggcctgcct agctccatcg aaaagaccat ctccaaggcc 1020

```
aagggccagc ctcgagaacc ccaggtttac accctgcctc caagccagaa agagatgacc   1080

aagaaccagg tgtccctgac ctgcctcgtg aagggcttct acccttccga tatcgccgtg   1140

gaatgggaga gcaatggcca gccagagaac aactacaaga ccacacctcc tgtgctggac   1200

tccgatggct cattctttct gtactccaag ctgacagtgg acaagtcccg gtggcaagag   1260

ggcaacgtgt tctcctgctc tgtgatgcac gaggccctgc acaaccacta cacccagaag   1320

tccctgtctc tgtcccct                                                  1338
```

<210> SEQ ID NO 95
<211> LENGTH: 446
<212> TYPE: PRT
<213> ORGANISM: Artificial Sequence
<220> FEATURE:
<223> OTHER INFORMATION: T0736H-IgG4-P E356K amino acid sequence

<400> SEQUENCE: 95

```
Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Lys Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Leu Ile Gln Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300
```

```
Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Lys Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Pro
        435                 440                 445


<210> SEQ ID NO 96
<211> LENGTH: 325
<212> TYPE: DNA
<213> ORGANISM: Homo Sapiens

<400> SEQUENCE: 96

tcctatgtgc tgactcagcc accctcagtg tcagtggccc caggagagac ggccaggatt      60

acctgtgggg gagacaacat tggaaggaaa agtgtgtact ggtaccagca gaagtcaggc     120

caggcccctg tgctggtcat ctattatgat agcgaccggc cctcagggat ccctgagcga     180

ttctctgggt ccaactctgg gaacacggcg accctgacca tcagcagggt cgaagccggg     240

gatgaggccg actattactg tcaggtgtgg gatggaagta gtgatcattg ggtgttcggc     300

ggagggacca agttgaccgt cctag                                           325


<210> SEQ ID NO 97
<211> LENGTH: 108
<212> TYPE: PRT
<213> ORGANISM: Homo Sapiens

<400> SEQUENCE: 97

Ser Tyr Val Leu Thr Gln Pro Pro Ser Val Ser Val Ala Pro Gly Glu
1               5                   10                  15

Thr Ala Arg Ile Thr Cys Gly Gly Asp Asn Ile Gly Arg Lys Ser Val
            20                  25                  30

Tyr Trp Tyr Gln Gln Lys Ser Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Gly Ser Ser Asp His
                85                  90                  95

Trp Val Phe Gly Gly Gly Thr Lys Leu Thr Val Leu
            100                 105


<210> SEQ ID NO 98
```

<211> LENGTH: 642
<212> TYPE: DNA
<213> ORGANISM: Homo Sapiens

<400> SEQUENCE: 98

```
tcctatgtgc tgactcagcc accctcagtg tcagtggccc caggagagac ggccaggatt     60

acctgtgggg gagacaacat tggaaggaaa agtgtgtact ggtaccagca gaagtcaggc    120

caggcccctg tgctggtcat ctattatgat agcgaccggc cctcagggat ccctgagcga    180

ttctctgggt ccaactctgg gaacacggcg accctgacca tcagcagggt cgaagccggg    240

gatgaggccg actattactg tcaggtgtgg gatggaagta gtgatcattg ggtgttcggc    300

ggagggacca agttgaccgt cctaggtcag cccaaggctg ccccctcggt cactctgttc    360

ccaccctcct ctgaggagct tcaagccaac aaggccacac tggtgtgtct cataagtgac    420

ttctacccgg gagccgtgac agtggcctgg aaggcagata gcagccccgt caaggcggga    480

gtggagacca ccacaccctc caaacaaagc aacaacaagt acgcggccag cagctacctg    540

agcctgacgc ctgagcagtg gaagtcccac aaaagctaca gctgccaggt cacgcatgaa    600

gggagcaccg tggagaagac agtggcccct acagaatgtt ca                       642
```

<210> SEQ ID NO 99
<211> LENGTH: 214
<212> TYPE: PRT
<213> ORGANISM: Homo Sapiens

<400> SEQUENCE: 99

```
Ser Tyr Val Leu Thr Gln Pro Pro Ser Val Ser Val Ala Pro Gly Glu
1               5                   10                  15

Thr Ala Arg Ile Thr Cys Gly Gly Asp Asn Ile Gly Arg Lys Ser Val
            20                  25                  30

Tyr Trp Tyr Gln Gln Lys Ser Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Gly Ser Ser Asp His
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Lys Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 100
<211> LENGTH: 321
<212> TYPE: DNA
<213> ORGANISM: Homo Sapiens

<400> SEQUENCE: 100

```
tacgtgctga cccagcctcc ttccgtgtct gttgctcctg gcgagacagc cagaatcacc      60

tgtggcggcg ataacatcgg ccggaagtcc gtgtactggt atcagcagaa gtccggccag     120

gctcctgtgc tggtcatcta ctacgactcc gaccggcctt ctggcatccc tgagagattc     180

tccggctcca actccggcaa taccgccaca ctgaccatct ccagagtgga agctggcgac     240

gaggccgact actactgcca agtgtgggac ggctcctctg accactgggt tttcggcgga     300

ggcaccaagc tgacagtgct g                                               321
```

<210> SEQ ID NO 101
<211> LENGTH: 107
<212> TYPE: PRT
<213> ORGANISM: Homo Sapiens

<400> SEQUENCE: 101

```
Tyr Val Leu Thr Gln Pro Pro Ser Val Ser Val Ala Pro Gly Glu Thr
1               5                   10                  15

Ala Arg Ile Thr Cys Gly Gly Asp Asn Ile Gly Arg Lys Ser Val Tyr
            20                  25                  30

Trp Tyr Gln Gln Lys Ser Gly Gln Ala Pro Val Leu Val Ile Tyr Tyr
        35                  40                  45

Asp Ser Asp Arg Pro Ser Gly Ile Pro Glu Arg Phe Ser Gly Ser Asn
    50                  55                  60

Ser Gly Asn Thr Ala Thr Leu Thr Ile Ser Arg Val Glu Ala Gly Asp
65                  70                  75                  80

Glu Ala Asp Tyr Tyr Cys Gln Val Trp Asp Gly Ser Ser Asp His Trp
                85                  90                  95

Val Phe Gly Gly Gly Thr Lys Leu Thr Val Leu
            100                 105
```

<210> SEQ ID NO 102
<211> LENGTH: 639
<212> TYPE: DNA
<213> ORGANISM: Homo Sapiens

<400> SEQUENCE: 102

```
tacgtgctga cccagcctcc ttccgtgtct gttgctcctg gcgagacagc cagaatcacc      60

tgtggcggcg ataacatcgg ccggaagtcc gtgtactggt atcagcagaa gtccggccag     120

gctcctgtgc tggtcatcta ctacgactcc gaccggcctt ctggcatccc tgagagattc     180

tccggctcca actccggcaa taccgccaca ctgaccatct ccagagtgga agctggcgac     240

gaggccgact actactgcca agtgtgggac ggctcctctg accactgggt tttcggcgga     300

ggcaccaagc tgacagtgct gggacaacct aaggccgctc cttctgtgac cctgtttcct     360

ccatcctccg aggaactgca ggccaacaag gctaccctcg tgtgcctgat ctccgacttt     420

taccctggcg ctgtgaccgt ggcctggaag gctgatagtt ctcctgtgaa ggccggcgtg     480

gaaaccacca caccttccaa gcagtccaac aacaaatacg ccgcctcctc ctacctgtct     540

ctgacccctg aacagtggaa gtcccacaag tcctactctt gccaagtgac ccacgagggc     600

tccaccgtgg aaaagacagt ggctcctacc gagtgctcc                            639
```

<210> SEQ ID NO 103
<211> LENGTH: 213
<212> TYPE: PRT
<213> ORGANISM: Homo Sapiens

<400> SEQUENCE: 103

```
Tyr Val Leu Thr Gln Pro Pro Ser Val Ser Val Ala Pro Gly Glu Thr
1               5                   10                  15

Ala Arg Ile Thr Cys Gly Gly Asp Asn Ile Gly Arg Lys Ser Val Tyr
            20                  25                  30

Trp Tyr Gln Gln Lys Ser Gly Gln Ala Pro Val Leu Val Ile Tyr Tyr
        35                  40                  45

Asp Ser Asp Arg Pro Ser Gly Ile Pro Glu Arg Phe Ser Gly Ser Asn
    50                  55                  60

Ser Gly Asn Thr Ala Thr Leu Thr Ile Ser Arg Val Glu Ala Gly Asp
65                  70                  75                  80

Glu Ala Asp Tyr Tyr Cys Gln Val Trp Asp Gly Ser Ser Asp His Trp
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Lys Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

<210> SEQ ID NO 104
<211> LENGTH: 327
<212> TYPE: PRT
<213> ORGANISM: Artificial Sequence
<220> FEATURE:
<223> OTHER INFORMATION: IgG4 PE human heavy chain constant region

<400> SEQUENCE: 104

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110
```

```
Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 105
<211> LENGTH: 327
<212> TYPE: PRT
<213> ORGANISM: Artificial Sequence
<220> FEATURE:
<223> OTHER INFORMATION: IgG4 human heavy chain constant region with
      knobs-into-holes mutations and hinge mutation. Type a (IgG4ra)

<400> SEQUENCE: 105

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
```

```
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Cys Thr Leu Pro Pro Ser Gln Glu Glu Met Thr Lys
225                 230                 235                 240

Asn Gln Val Ser Leu Trp Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 106
<211> LENGTH: 327
<212> TYPE: PRT
<213> ORGANISM: Artificial Sequence
<220> FEATURE:
<223> OTHER INFORMATION: IgG4 human heavy chain constant region with
      knobs-into-holes mutations and hinge mutation. Type b (IgG4yb)

<400> SEQUENCE: 106

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Cys Glu Met Thr Lys
225                 230                 235                 240

Asn Gln Val Ser Leu Ser Cys Ala Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Val Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 107
<211> LENGTH: 325
<212> TYPE: PRT
<213> ORGANISM: Artificial Sequence
<220> FEATURE:
<223> OTHER INFORMATION: IgG4 human heavy chain constant region with P
      (hinge) mutation and K439E

<400> SEQUENCE: 107

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Glu Ser
305                 310                 315                 320

Leu Ser Leu Ser Pro
                325


<210> SEQ ID NO 108
<211> LENGTH: 325
<212> TYPE: PRT
<213> ORGANISM: Artificial Sequence
<220> FEATURE:
<223> OTHER INFORMATION: IgG4 human heavy chain constant region with P
      (hinge) mutation and E356K

<400> SEQUENCE: 108

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
```

```
    210                 215                 220

Glu Pro Gln Val Tyr Thr Leu Pro Pro Ser Gln Lys Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro
                325


<210> SEQ ID NO 109
<211> LENGTH: 975
<212> TYPE: DNA
<213> ORGANISM: Artificial Sequence
<220> FEATURE:
<223> OTHER INFORMATION: IgG4-P K439E encoding nucleic acid

<400> SEQUENCE: 109

gcttccacca agggacccag cgttttccct ctggctcctt gctccagatc cacctccgag      60

tctacagctg ctctgggctg cctggtcaag gactactttc ctgagcctgt gaccgtgtcc     120

tggaactctg gcgctctgac atctggcgtg cacacctttc cagctgtgct gcagtcctcc     180

ggcctgtact ctctgtcctc tgtcgtgacc gtgccttcca gctctctggg aacccagacc     240

tacacctgta atgtggacca caagccttcc aacaccaagg tggacaagcg cgtggaatct     300

aagtacggcc ctccttgtcc tccatgtcct gctccagagt ttctcggcgg accctccgtg     360

tttctgttcc ctccaaagcc taaggacacc ctgatgatct ctcggacccc tgaagtgacc     420

tgcgtggtgg tggatgtgtc ccaagaggat cccgaggtgc agttcaattg gtacgtggac     480

ggcgtggaag tgcacaatgc caagaccaag cctagagagg aacagtacaa ctccacctac     540

agagtggtgt ccgtgctgac cgtgctgcac caggattggc tgaacggcaa agagtacaag     600

tgcaaggtgt ccaacaaggg cctgcctagc tccatcgaaa agaccatctc caaggccaag     660

ggccagcctc gagaacccca ggtttacacc ctgcctccaa gccaagagga aatgaccaag     720

aaccaggtgt ccctgacctg tctcgtgaag ggcttctacc cctccgatat cgccgtggaa     780

tgggagtcta atggccagcc agagaacaac tacaagacca cacctccagt gctggactcc     840

gacggctcat tctttctgta ctccaagctg acagtggaca agtcccggtg gcaagagggc     900

aacgtgttct cctgctctgt gatgcacgag gccctgcaca accactacac ccaagagtcc     960

ctgtctctgt cccct                                                      975


<210> SEQ ID NO 110
<211> LENGTH: 975
<212> TYPE: DNA
<213> ORGANISM: Artificial Sequence
<220> FEATURE:
<223> OTHER INFORMATION: IgG4-P E356K encoding nucleic acid

<400> SEQUENCE: 110

gcttccacca agggacccag cgtgttccct ctggctcctt gctccagatc cacctccgag      60
```

```
tctacagctg ctctgggctg cctggtcaag gactactttc ctgagcctgt gaccgtgtct    120

tggaactctg gcgctctgac atctggcgtg cacacctttc cagctgtgct gcagtcctcc    180

ggcctgtact ctctgtcctc tgtcgtgacc gtgccttcca gctctctggg aacccagacc    240

tacacctgta atgtggacca caagccttcc aacaccaagg tggacaagcg cgtggaatct    300

aagtacggcc ctccttgtcc tccatgtcct gctccagagt ttctcggcgg accctccgtg    360

tttctgttcc ctccaaagcc taaggacacc ctgatgatct ctcggacccc tgaagtgacc    420

tgcgtggtgg tggatgtgtc ccaagaggat cccgaggtgc agttcaattg gtacgtggac    480

ggcgtggaag tgcacaacgc caagaccaag cctagagagg aacagtacaa ctccacctac    540

agagtggtgt ccgtgctgac cgtgctgcac caggattggc tgaacggcaa agagtacaag    600

tgcaaggtgt ccaacaaggg cctgcctagc tccatcgaaa agaccatctc caaggccaag    660

ggccagcctc gagaacccca ggtttacacc ctgcctccaa gccagaaaga gatgaccaag    720

aaccaggtgt ccctgacctg cctcgtgaag ggcttctacc cttccgatat cgccgtggaa    780

tgggagagca atggccagcc agagaacaac tacaagacca cacctcctgt gctggactcc    840

gatggctcat tctttctgta ctccaagctg acagtggaca agtcccggtg gcaagagggc    900

aacgtgttct cctgctctgt gatgcacgag gccctgcaca accactacac ccagaagtcc    960

ctgtctctgt cccct                                                     975
```

<210> SEQ ID NO 111
<211> LENGTH: 318
<212> TYPE: DNA
<213> ORGANISM: Homo Sapiens

<400> SEQUENCE: 111

```
ggacaaccta aggccgctcc ttctgtgacc ctgtttcctc catcctccga ggaactgcag     60

gccaacaagg ctaccctcgt gtgcctgatc tccgactttt accctggcgc tgtgaccgtg    120

gcctggaagg ctgatagttc tcctgtgaag gccggcgtgg aaaccaccac accttccaag    180

cagtccaaca acaaatacgc cgcctcctcc tacctgtctc tgacccctga acagtggaag    240

tcccacaagt cctactcttg ccaagtgacc cacgagggct ccaccgtgga aaagacagtg    300

gctcctaccg agtgctcc                                                  318
```

<210> SEQ ID NO 112
<211> LENGTH: 106
<212> TYPE: PRT
<213> ORGANISM: Homo Sapiens

<400> SEQUENCE: 112

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
```

```
            100                 105


<210> SEQ ID NO 113
<211> LENGTH: 108
<212> TYPE: PRT
<213> ORGANISM: Homo Sapiens

<400> SEQUENCE: 113

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105


<210> SEQ ID NO 114
<211> LENGTH: 5
<212> TYPE: PRT
<213> ORGANISM: Homo Sapiens

<400> SEQUENCE: 114

Thr Asp Ala Arg Cys
1               5


<210> SEQ ID NO 115
<211> LENGTH: 128
<212> TYPE: PRT
<213> ORGANISM: Homo Sapiens

<400> SEQUENCE: 115

Met Ser Val Pro Thr Gln Val Leu Gly Leu Leu Leu Leu Trp Leu Thr
1               5                   10                  15

Asp Ala Arg Cys Ser Tyr Val Leu Thr Gln Pro Pro Ser Val Ser Val
            20                  25                  30

Ala Pro Gly Glu Thr Ala Arg Ile Thr Cys Gly Gly Asp Asn Ile Gly
        35                  40                  45

Arg Lys Ser Val Tyr Trp Tyr Gln Gln Lys Ser Gly Gln Ala Pro Val
    50                  55                  60

Leu Val Ile Tyr Tyr Asp Ser Asp Arg Pro Ser Gly Ile Pro Glu Arg
65                  70                  75                  80

Phe Ser Gly Ser Asn Ser Gly Asn Thr Ala Thr Leu Thr Ile Ser Arg
                85                  90                  95

Val Glu Ala Gly Asp Glu Ala Asp Tyr Tyr Cys Gln Val Trp Asp Gly
            100                 105                 110

Ser Ser Asp His Trp Val Phe Gly Gly Gly Thr Lys Leu Thr Val Leu
        115                 120                 125
```

λ ANTIBODIES

RELATED APPLICATIONS

This application is a 35 U.S.C. § 371 filing of International Patent Application No. PCT/EP2020/063515, filed May 14, 2020, which claims priority to Great Britain Patent Application Nos. 1919077.6, filed Dec. 20, 2019, 1906816.2, filed May 15, 2019, and 1908190.0, filed Jun. 7, 2019, and European Patent Application No. PCT/EP2019/086808, filed Dec. 20, 2019, the entire disclosures of which are hereby incorporated herein by reference.

SEQUENCE LISTING

The instant application contains a Sequence Listing which has been submitted in electronically in ASCII format and is hereby incorporated by reference in its entirety. Said ASCII copy, created on Jun. 29, 2022, is named 723307_SA9-644US_ST25.txt and is 115,963 bytes in size.

FIELD OF THE INVENTION

The present invention relates to antibody lambda (λ) light chain variable (VL) domains and to antibodies comprising them (λ antibodies). The invention further relates to expression of λ antibodies from engineered nucleic acid in recombinant host cells.

BACKGROUND

Monoclonal antibodies are a successful and expanding class of biopharmaceuticals. The majority of antibodies in current clinical use are IgG immunoglobulins comprising two disulphide-linked pairs of heavy and light polypeptide chains. In natural human antibodies there are two classes of antibody light chain, kappa (κ) and lambda (λ), so an IgG may be either an IgGκ or an IgGλ, depending on whether the light chain was produced by rearrangement of the immunoglobulin κ or λ light chain locus in the developing B lymphocyte. In humans, IgGκ and IgGλ are found in approximately equal amounts (55% κ; 45% λ). However, the majority of antibodies developed for human clinical use are IgGκ antibodies, with relatively few A antibodies being in production.

The main production method for monoclonal antibodies is recombinant expression of nucleic acid encoding the antibody heavy and light chains in cultured host cells in vitro. In a typical production system, antibody heavy and light chains are co-translated and secreted from the host cell.

Efforts have been made to increase polypeptide expression by varying many different aspects of recombinant systems, since higher antibody yields improve the efficiency of manufacture and reduce production costs.

One perceived bottleneck in the secretory pathway is translocation of the antibody polypeptides into the lumen of the endoplasmic reticulum (ER), via signal peptides. The signal peptide is a short (15-30 amino acid) sequence at the N terminus of the antibody heavy and light chains, which directs its translocation and is cleaved during the translocation process so is not a part of the secreted mature polypeptide chains. Efforts have been made to find signal peptides which generate higher antibody yields.

In addition to their role in secretion efficiency, signal peptides are linked to the industrial problem of cleavage heterogeneity which occurs as a result of non-specific cleavage of the signal peptide. This phenomenon can lead to either elongation or truncation of the N-terminus of the heavy and light chains, which may not be suitable for biopharmaceutical therapeutics and which may change the antibody affinity. Modified signal peptides have also been reported to modulate folding, thermodynamic stability and aggregation propensities of their cargo proteins. Effects of signal peptides and other variables in monoclonal antibody production were recently reviewed by Gupta et al. (Biotechnol Adv 2019).

Rance & Young (Evaluation of Alternative Signal Sequences, in T. Noll (ed.), Cells and Culture, ESACT Proceedings 4, 271 DOI 10.1007/978-90-481-3419-9_47; WO2008/148519 Lonza) evaluated 19 signal sequences with respect to antibody production in a transient expression system and from stable cell lines. The antibody genes were designed to include either the signal sequences routinely used at Lonza or 19 alternative sequences (V1-V19). They identified a number of signal sequences which reportedly provided a proper processing and an efficient secretion of operably linked polypeptide sequences when used in expression cassettes in mammalian host cells, including V12, V14, V16 and V19 shown in Table P herein. V19 and V17 were said to produce a particularly strong increase in mean antibody concentration over control cell lines employing the signal sequences routinely used.

Kotia and Raghani (Anal Biochem 399 190-195 2010) described heterogeneity in a monoclonal antibody due to varying cleavage sites of the signal peptides in both the heavy chain and light chain of a monoclonal antibody expressed in CHO cells.

Haryadi et al (PLoS ONE 10(2): e0116878 2015) optimised the signal peptide sequences for five top-selling monoclonal antibodies. Optimisation of the signal peptide for rituximab resulted in two-fold increase in titre compared with the native signal peptide.

Gibson et al (Biotechnol Bioeng 114: 1970-1977 2017) and WO2017/072310 (MedImmune) reported that recombinant antibody light chains having a murine secretory leader sequence MGWSCIILFLVATATGVHS (SEQ ID NO: 74) a commonly used signal sequence for recombinant antibody production) and an SYE motif at the N-terminus are truncated during post-translational processing, observing that about 3-8% of the final antibody product MEDI8490 contained a truncated light chain. The truncated light chain was missing three amino acids at its N-terminus (SYE) and was considered a risk to product development. Two protein engineering solutions were attempted to prevent truncation of the light chain N terminus: altering the SYE amino acid sequence or changing the secretory leader peptide sequence. They exemplified two λ leader sequences, MAWTPLLLPLLTLCTSEA (Vλ3 family SEQ ID NO: 75) and MAGFPLLLTLLTHCAGSWA (Vλ1 family SEQ ID NO: 76), and a κ leader sequence MDMRVPAQLLGLLLLWLPGAKC (Vκ1 family SEQ ID NO: 77) and the SYE truncation did not occur with these leader sequences.

SUMMARY OF THE INVENTION

The present inventors discovered that changing the signal peptide of a λ VL domain causes a change in the site at which the signal peptide is cleaved from the VL domain, so that different signal peptides result in λ VL domains having different N-terminal sequences. Antibodies containing such λ VL domains (e.g., antibodies comprising two heavy chains and two λ light chains) therefore have different VL domain N-terminal amino acid sequences, depending on the amino acid sequence of the signal peptide expressed from their encoding nucleic acid.

Unlike earlier reports of heterogeneity in expression, where antibody chains of different sequences are obtained from the same encoding nucleic acid, the present inventors observed consistent expression of a single VL domain amino acid sequence per nucleic acid coding sequence. The exact N-terminal sequence of the VL domain, however, differed depending on the upstream sequence of the signal peptide present in the pre-cleaved light chain.

Specifically, the inventors compared expression of a λ light chain comprising an N-terminal signal peptide which was either (i) the native signal peptide associated with the encoding vλ gene segment in the germline DNA or (ii) a signal peptide commonly used for light chain expression in recombinant host cells, but which originated from a different v gene segment (mouse vκ gene segment). They observed that the λ light chain expressed with the native signal peptide was cleaved to provide a mature light chain in which the N-terminal residue corresponded to IMGT position 2, whereas the λ light chain expressed with the non-native signal peptide was cleaved to provide a mature light chain in which the N-terminal residue corresponded to IMGT position 1. This is surprising, since it has generally been believed that IMGT position 1 is the first residue of the mature polypeptide chain in an antibody. The IMGT numbering of VL domains, and the VL domain sequences represented in various public sequence databases, pre-suppose that the N-terminal residue of the VL domain is IMGT position 1. The present inventors are believed to be the first to discover that there are λ antibodies in which the N-terminal residue of the VL domain corresponds to IMGT position 2 when the antibody is expressed from its native encoding nucleic acid. The work presented herein indicates that certain naturally occurring λ antibodies, and λ antibodies expressed using nucleotide sequences encoding the light chain with its native signal peptide, lack the N-terminal amino acid which was previously assumed to be present based on IMGT notation, i.e., these A antibodies do not have an amino acid at IMGT position 1. As demonstrated in various embodiments, a native N-terminal signal peptide is cleaved to provide a λ VL domain having an N-terminal residue corresponding to IMGT position 2, whereas a non-native N-terminal signal peptide is cleaved to provide a λ VL domain having an N-terminal residue corresponding to IMGT position 1. The site of cleavage may thus differ by one amino acid depending on the sequence of the signal peptide.

Notably, the inventors found that in some embodiments the variation in cleavage site, and thus the change in N-terminal VL domain sequence, influenced the properties of the λ antibody. For example, λ antibodies comprising the VL domains with different N-terminal sequences showed different functional activity. In various embodiments, the invention builds on this effect to provide λ antibodies with desired properties. For example, the influence of a non-native signal peptide sequence on the N-terminal sequence of the VL domain may be over-ridden by a "forced" deletion of IMGT position 1 when expressing a VL domain with a non-native signal peptide, so that the resulting mature VL domain has the same sequence as if it had been expressed with its native signal peptide (i.e., the N-terminal residue of the mature VL domain corresponds to IMGT position 2). As demonstrated in the Examples, this restored activity of the antibody which had been lost on changing from its native light chain leader to a non-native leader. In various aspects, the present invention provides λ antibodies, λ VL domains, encoding nucleic acids, methods and for their expression in recombinant host cells, and compositions containing λ antibodies isolated from such recombinant expression systems.

Aspects of the invention are set out in the appended claims and in the accompanying disclosure.

In a first aspect, the present invention provides a polypeptide comprising an antibody VL domain with an N-terminal signal peptide, wherein the VL domain comprises a sequence derived from a v A gene segment and a sequence derived from a j gene segment, wherein the N-terminal signal peptide differs from the native N-terminal signal peptide for said vλ gene segment, and wherein the residue corresponding to IMGT position 1 of the VL domain is absent.

The polypeptide thus lacks an amino acid at IMGT position 1 of the VL domain, so that effectively there is a deletion at this position, and the N-terminal residue of the VL domain corresponds to IMGT position 2.

In embodiments of the invention, the VL domain is one which, when expressed with its native signal peptide (i.e., the N-terminal signal peptide for the vλ gene segment from which said VL domain is derived), lacks an amino acid at IMGT position 1 of the VL domain. When expressed and cleaved from its native signal peptide, the N-terminal residue of the VL domain thus corresponds to IMGT position 2.

A VL domain is derived from recombination of a v gene segment and a j gene segment. In vivo, recombination takes place at the DNA level and involves genomic rearrangement in cells that develop into B cells. VL domains of antibodies expressed by B cells thus comprise amino acid sequences translated from nucleic acid derived from recombination of the v and j gene segment. Examination of the amino acid sequence of a VL domain allows the v and j gene segments to be identified, by comparison against the translated sequences of germline v and j gene segments.

Preferably, a gene segment herein is a vertebrate gene segment, e.g., a mammalian gene segment. More preferably, the gene segment is a human gene segment. The invention has particular relevance for expression of human VL domains and human antibodies comprising them. A human VL domain is derived from recombination of a human v gene segment and a human j gene segment. Thus, in preferred embodiments, the v λ gene segment is a human v λ gene segment and/or the j gene segment is a human j gene segment. The j gene segment is preferably a λ gene segment, although combination of a v λ with a j κ gene segment is possible.

Appended Table L shows examples of human λ v gene segments. Preferably, the v λ gene segment is a vλ3 gene segment, i.e., a member of the IGLV3 family. This includes the following human v λ gene segments: vλ3-1, vλ3-9, vλ3-10, vλ3-12, vλ3-13, vλ3-16, vλ3-19, vλ3-21, vλ3-22, vλ3-25, vλ3-27, vλ3-31 and vλ3-32. Preferably, the v λ gene segment is a functional gene segment. Thus, the v λ gene segment is optionally selected from the group consisting of: vλ3-1, vλ3-9, vλ3-10, vλ3-12, vλ3-16, vλ3-19, vλ3-21, vλ3-22, vλ3-25 and vλ3-27.

Amino acid sequences of VL domains generated from v λ gene segment are available from IMGT and examples are shown in Table L. IMGT predicts the first residue of the mature VL domain and designates this as IMGT position 1. A v λ gene segment according to the present invention may encode an amino acid sequence in which the first residue (IMGT position 1) is Ser (S). A v λ gene segment according to the present invention may encode an amino acid sequence in which the first two residues (IMGT positions 1 and 2) are Ser and Tyr (SY). It may encode an amino acid sequence in which the first three residues (IMGT positions 1, 2 and 3) are Ser, Tyr and Val (SYV).

A preferred vλ gene segment is vλ3-21. Alleles of vλ3-21 are known. These include vλ3-21*01, vλ3-21*d01, vλ3-31*02 and vλ3-21*03.

A polypeptide according to the present invention may comprise a VL domain with an N-terminal signal peptide, wherein

- the VL domain comprises a sequence derived from a human vλ3 gene segment (e.g., vλ3-21) and a sequence derived from a j gene segment, wherein
- the N-terminal signal peptide is not a native signal peptide for a human vλ3 gene segment, wherein
- the vλ3 gene segment encodes an amino acid sequence for which the N-terminal residues at IMGT positions 1 and 2 are Ser and Tyr (SY) respectively, and wherein
- the VL domain comprises a deletion of Ser at IMGT position 1.

The VL domain comprises the signal peptide immediately fused to the VL domain, wherein the VL domain is derived from recombination of a human vλ3 gene segment and a v j gene segment, wherein the VL domain lacks a Ser residue at IMGT position 1, i.e., N-terminal Ser of the VL domain is deleted.

On expression in a host cell, the N-terminal residue of the VL domain following cleavage of the signal peptide is therefore the residue (e.g., Tyr) at IMGT position 2. Gene segment v3-21 encodes an amino acid sequence in which the first three residues according to IMGT are Ser Tyr Val (SYV) and therefore, when the Ser at IMGT position 1 is deleted, the N-terminal residues of the VL domain following cleavage of the signal peptide are Tyr Val (YV).

In embodiments of the invention, the non-native signal peptide (the N-terminal signal peptide which differs from the native N-terminal signal peptide for said vλ gene segment) is one which would be cleaved from the polypeptide immediately before the residue corresponding to IMGT position 1 of the VL domain, if said residue were present. Thus, when the residue corresponding to IMGT position 1 of the VL domain (e.g., Ser) is present in the VL domain of the polypeptide, the signal peptide is cleaved immediately before said residue corresponding to IMGT position 1 of the VL domain. Deletion of said residue thus avoids the presence of this residue in the mature polypeptide. In various embodiments this may have the effect of restoring or enhancing function of the antibody as compared with an antibody comprising the VL domain in which said residue is present.

Signal peptides may be of varying length but usually between approximately 18-22 amino acids. Optionally, the signal peptide is 20 amino acids in length. The signal peptide is not the native signal peptide for the vλ gene segment in the polypeptide. It may be a signal peptide from another gene of the same or a different species, e.g., a mouse signal peptide may be combined with a VL domain derived from recombination of human gene segments. Although the signal peptide may be naturally occurring, and may thus be the native signal peptide from a different genomic coding sequence, it is optionally not the signal peptide from any vλ gene segment. Examples of heterologous signal peptides are disclosed herein and include signal peptides from light chain K gene segments, including mouse v K gene segments such as the commonly used signal peptide MSVPTQVLGLLLL-WLTDARC (SEQ ID NO: 62).

The C-terminal region of the signal peptide is believed to influence the site of cleavage. Preferably, the signal peptide comprises a C-terminal Cys residue and thus on expression in a host cell is cleaved from the VL domain immediately after the Cys. The N-terminal residue of the mature VL domain is thus the residue immediately following the C-terminal Cys of the signal peptide. The signal peptide may comprise a C-terminal sequence Ala Arg Cys (ARC). It may comprise a C-terminal sequence Thr Asp Ala Arg Cys (TDARC SEQ ID NO: 114).

In one embodiment, a polypeptide according to the present invention comprises a VL domain with an N-terminal signal peptide, wherein

- the VL domain comprises a sequence derived from a human vλ3-31 gene segment and a sequence derived from a human j A gene segment, wherein
- the N-terminal signal peptide is a mouse v K gene segment signal peptide, and wherein
- the VL domain comprises a deletion of Ser at IMGT position 1.

The VL domain may be the 0325L VL domain exemplified herein, or it may be a variant thereof such as a VL domain having at least 90% amino acid sequence identity to the 0325 VL domain. Amino acid sequence identity may be at least 95%, at least 96%, at least 97%, at least 98% or at least 99%.

Further aspects of the present invention include nucleic acid molecules encoding the polypeptides (e.g., cDNA or genomic DNA), such as DNA vectors.

Host cells may be transfected with said nucleic acid and cultured for expression of the polypeptides. Host cells may be provided in vitro and cultured under laboratory conditions. Host cells may also be stored, e.g., as frozen stocks. Host cells may comprise recombinant DNA encoding the polypeptide, e.g., wherein the encoding DNA is stably integrated into the cellular DNA (e.g., in the host cell genome). Cells that are transiently transfected with the encoding nucleic acid may also be used. A host cell may be a eukaryotic cell, e.g., a vertebrate cell, e.g., a mammalian cell. A number of established cell lines for polypeptide expression are known in the art and are obtainable from cell banks. Such cells may also be further modified for additional desired attributes. Examples include Chinese Hamster Ovary (CHO) cells, e.g., CHO-K1 or CHO GS, and Human Embryonic Kidney (HEK) cells, e.g., HEK293.

On expression within host cells, the signal peptide directs the polypeptide to the ER membrane where it is cleaved by signal peptidase. The signal peptide is cleaved from the polypeptide to provide a mature VL domain comprising an N-terminal residue corresponding to IMGT position 2. Cells may secrete the resultant polypeptide comprising the mature VL domain (lacking the signal peptide), whereupon it may be recovered from the culture medium and optionally further purified and formulated as desired. Alternatively cells may display the polypeptide on the cell surface as a membrane protein (e.g., IgM).

Accordingly, further aspects of the invention relate to methods of producing a polypeptide comprising a VL domain, wherein the VL domain has an N-terminus generated by cleavage of an N-terminal signal polypeptide as described herein, wherein the N-terminus of the VL domain corresponds to IMGT position 2.

A method of expressing a polypeptide comprising a VL domain may comprise

- culturing a population of cells under conditions for expression of the polypeptide, wherein the cells comprise nucleic acid encoding a polypeptide comprising an N-terminal signal peptide and a VL domain, wherein the N-terminal signal peptide is cleaved off the VL domain to provide a polypeptide comprising a mature VL domain, and wherein the N-terminal residue of the polypeptide comprising the mature VL domain is IMGT position 2 of the VL domain.

The polypeptide may be an antibody light chain, optionally comprising a λ constant domain. The method may comprise producing an antibody comprising said VL domain or light chain and a VH domain or heavy chain. Antibody light and heavy chains may be co-expressed within the same cell or separately expressed and then assembled.

One method comprises expressing an antibody comprising a VH domain and a VL domain, wherein the VL domain comprises a sequence derived from a v A gene segment and a sequence derived from a j gene segment, including providing cells with nucleic acid encoding a VL domain and N-terminal signal peptide as described herein, wherein the cells further comprise nucleic acid encoding the VH domain, culturing said population of cells under conditions for expression of the polypeptide comprising the VL domain and for expression of the VH domain, wherein the N-terminal signal peptide is cleaved off the VL domain to provide a polypeptide comprising a mature VL domain, wherein the N-terminal residue of the polypeptide comprising the mature VL domain is IMGT position 2 of the VL domain, and wherein the VL domain assembles with the VH domain to provide said antibody.

Thus, in various embodiments herein, a cell comprises nucleic acid encoding the polypeptide comprising the N-terminal signal peptide and the VL domain (e.g., an antibody light chain), and further comprises nucleic acid encoding an antibody VH domain (e.g., an antibody heavy chain). Optionally, a cell comprises nucleic acid encoding two different antibody VH domains, e.g., it may comprise nucleic acid encoding a first antibody heavy chain and nucleic acid encoding a second antibody heavy chain, wherein both the first and second antibody heavy chain assemble with the antibody light chain. The resulting antibody may thus comprise a first binding site formed by the VH domain of the first heavy chain and the VL domain, and a second binding site formed by the VH domain of the second heavy chain and the VL domain. The first and second binding sites may bind first and second epitopes respectively, e.g., on first and second antigens. Such a cell would generate a bispecific antibody having a common light chain. Alternatively a cell may comprise nucleic acid encoding multiple different VH domains and multiple different VL domains, e.g., two different VH domains and two different VL domains, to generate a bispecific antibody having four different antibody chains.

In preferred embodiments of the invention generally, the VL domain is derived from a vλ3-21 gene segment and a jλ gene segment. The VL domain amino acid sequence may be the 0325L VL domain amino acid sequence shown herein. The polypeptide is preferably an antibody light chain comprising the 0325 VL domain, e.g., it may be the 0325L light chain shown herein. Preferred embodiments include antibodies that comprise a λ light chain comprising the VL domain, paired with a heavy chain. A bispecific antibody may comprise two different antibody heavy chains each paired with a light chain, wherein one or both light chains comprise a λ VL domain as described herein. Preferred embodiments are the bispecific antibodies, methods for their production and cells which comprise nucleic acid encoding them, wherein the bispecific antibody comprises a first heavy chain comprising the N1280H VH domain or the N1441H VH domain, paired with a light chain comprising the 0325L VL domain; and a second heavy chain comprising the T0999H VH domain paired with a light chain comprising the 0325L VL domain.

The first and/or second heavy chain may comprise the VH domain and a human IgG4 constant region shown in Table S. The light chain may be a common light chain, e.g., the 0325L light chain shown in Table S. Examples of full heavy and light chains are shown in Table S.

It is shown herein that deletion of the Ser at IMGT position 1 of the 0325L light chain increases the functional activity of bispecific antibodies comprising 0325L as a common light chain, compared with bispecific antibodies that include the Ser at IMGT position 1 but are otherwise identical. Without being bound by theory, the inventors believe that this may be the result of the N-terminal Ser influencing the association between the VH and VL domain. In the absence of the N-terminal Ser, the VH and VL domain of one or both arms of the bispecific antibody may bind differently to its antigen, thereby influencing the function of the antibody. Optimisation of biophysical properties is critical for the developability of therapeutic antibodies, and the IXAX bispecific antibodies described herein may exhibit greater stability in the absence of an N-terminal Ser on the light chain. Another possibility, especially relevant for bispecific antibodies, is that the presence or absence of the residue at IMGT position 1 of the light chain may affect heterodimerisation, i.e., assembly of two different heavy chains to produce the bispecific rather than assembly of two identical heavy chains to produce unwanted monospecific homodimers.

While in some embodiments an antibody may benefit from the absence of the N-terminal Ser at IMGT position 1 of the VL domain, it is possible that the desired function of other λ antibodies may be improved by engineering the sequence so that the N-terminal residue at IMGT 1 is present. Depending on the intended use of the antibody, it may for example be desirable to have different antigen-binding characteristics such as a higher affinity or a lower affinity, different binding kinetics or to influence assembly of the antibody heavy and light chains. Particularly in the case of antibodies that are selected for function with an N-terminal residue present at IMGT position 1 (e.g., in the case of λ antibodies expressed with a non-native signal peptide), one may wish to ensure that said residue is retained when the antibody is recombinantly expressed in a host cell, even if this does not reflect the native structure of a naturally occurring λ antibody. It may therefore be desirable to provide a polypeptide comprising a VL domain with an N-terminal signal peptide, wherein the VL domain comprises a sequence derived from a v λ gene segment and a sequence derived from a j gene segment, wherein the N-terminal signal peptide differs from the native N-terminal signal peptide for said λ v gene segment, and wherein the residue corresponding to IMGT position 1 of the VL domain is present. An example is a polypeptide comprising the 0128L VL domain with a non-native signal peptide, e.g., the mouse κ light chain signal peptide MSVPTQVLGLLLL-WLTDARC (SEQ ID NO: 62).

Further aspects of the invention thus relate to the provision of VL domains in which an N-terminal residue is present at IMGT position 1, wherein said residue is absent from the mature VL domain expressed with its native signal peptide. For example, a VL domain may be provided which comprises a sequence derived from a v λ gene segment and a sequence derived from a j gene segment, wherein the residue corresponding to IMGT position 1 of the VL domain is present. The VL domain may be one which, when expressed with the native signal peptide of its v λ gene segment, lacks a residue at IMGT position 1 and thus has an N-terminal residue corresponding to IMGT position 2. By recombinantly expressing the VL domain with a non-native signal peptide, cleavage may occur immediately before the N-terminal residue corresponding to IMGT position 1, thus changing the VL domain sequence to include the N-terminal residue at IMGT position 1. In various embodiments, the invention provides polypeptides and antibodies comprising such VL domains, nucleic acids encoding them, host cells comprising such nucleic acids and methods of production by expression from host cells.

The invention further extends to methods of altering the stability, assembly and/or antigen-binding kinetics of an antibody comprising a VH domain and a VL domain, wherein the VL domain comprises a sequence derived from a v λ gene segment and a sequence derived from a j gene segment.

Such a method may comprise providing nucleic acid encoding said antibody, comprising a nucleotide sequence encoding said VL domain with an N-terminal signal peptide, wherein the codon for the residue corresponding to IMGT position 1 of said VL domain is deleted and wherein the N-terminal signal peptide is not the native N-terminal signal peptide for said A v gene segment, and nucleic acid encoding the VH domain, expressing said nucleic acid to provide an antibody comprising the VH domain and the VL domain, wherein the N-terminal residue of the VL domain is the residue corresponding to IMGT position 2, wherein the stability, assembly and/or antigen-binding kinetics of the antibody are different from the stability and/or antigen-binding kinetics of an antibody comprising a VH domain and a VL domain wherein the N-terminal residue of the VL domain is the residue corresponding to IMGT position 1. Thus, stability is increased, or assembly or antigen-binding kinetics are altered, relative to an antibody expressed from nucleic acid in which the codon for IMGT residue 1 is not deleted. An influence on antibody assembly refers to pairing of the polypeptide chains or domains from which the antibody is composed. For example, when two different heavy chains and a common light chain are co-expressed, an effect may be observed on heterodimer formation, wherein the proportion of heterodimer relative to homodimers is altered.

Alternatively, a method may comprise providing nucleic acid encoding said antibody, comprising a nucleotide sequence encoding said VL domain with an N-terminal signal peptide, wherein the codon for the residue corresponding to IMGT position 1 of said VL domain is present, and wherein the N-terminal signal peptide is not the native N-terminal signal peptide for said λ v gene segment, and nucleic acid encoding the VH domain, expressing said nucleic acid to provide an antibody comprising the VH domain and the VL domain, wherein the N-terminal residue of the VL domain is the residue corresponding to IMGT position 1, wherein the stability and/or antigen-binding kinetics of the antibody are different from the stability, assembly and/or antigen-binding kinetics of an antibody comprising a VH domain and a VL domain wherein the N-terminal residue of the VL domain is the residue corresponding to IMGT position 2.

Alternatively, a method may comprise providing nucleic acid encoding said antibody, comprising a nucleotide sequence encoding said VL domain with an N-terminal signal peptide, wherein the codon for the residue corresponding to IMGT position 1 of said VL domain is present, and wherein the N-terminal signal peptide is the native N-terminal signal peptide for said λ v gene segment, and nucleic acid encoding the VH domain, expressing said nucleic acid to provide an antibody comprising the VH domain and the VL domain, wherein the N-terminal residue of the VL domain is the residue corresponding to IMGT position 2, wherein the stability, assembly and/or antigen-binding kinetics of the antibody are different from the stability and/or antigen-binding kinetics of an antibody comprising a VH domain and a VL domain wherein the N-terminal residue of the VL domain is the residue corresponding to IMGT position 1.

Thus, the sequence of the signal peptide and/or the N terminus of the VL domain can be selected or engineered to achieve cleavage at the desired location, providing either a VL domain starting at IMGT position 1 or a VL domain starting at IMGT position 2.

Equivalents: Those skilled in the art will recognise, or be able to ascertain using no more than routine experimentation, many equivalents to the specific embodiments of the invention described herein. Such equivalents are intended to be within the scope of protection of the appended claims.

BRIEF DESCRIPTION OF THE DRAWINGS

Embodiments of the invention will now be described in detail, with reference to the drawings, in which FIG. 1 shows:

Figure 3:
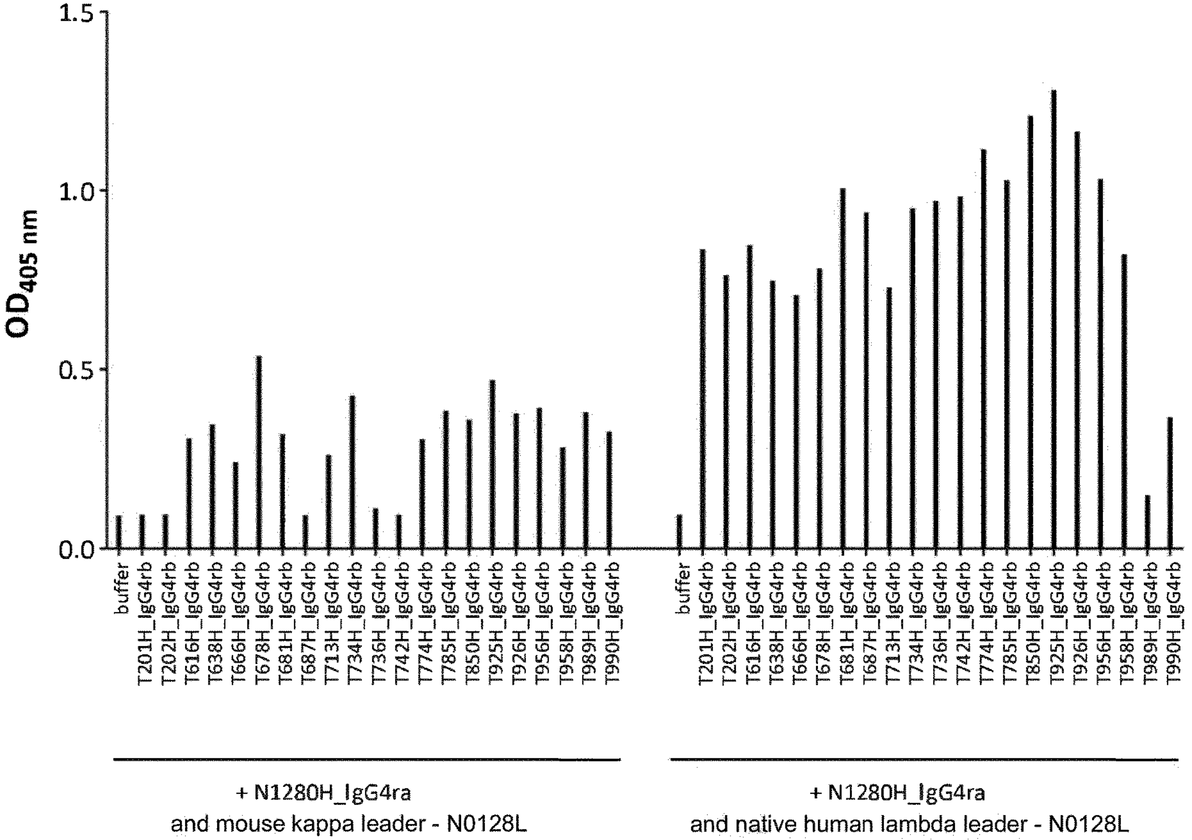

(A) Processing of the amino acid sequence SEQ ID NO: 115 of a polypeptide comprising a VL domain SEQ ID NO: 97 with native N-terminal signal peptide SEQ ID NO: 60. The native N-terminal signal peptide is underlined. The remainder of the polypeptide is the VL domain amino acid sequence as denoted by IMGT. The N-terminal signal peptide is cleaved immediately after the position corresponding to IMGT residue 1 of the VL domain. Cleavage site is marked by chevron and is between IMGT residues 1 and 2. Cleavage generates a mature VL domain SEQ ID NO: 101 in which the N-terminal residue corresponds to IMGT position 2. The generated VL domain has the amino acid sequence of the 0325 VL domain.

(B) Processing of the amino acid sequence of a polypeptide SEQ ID NO: 68 comprising a VL domain SEQ ID NO: 97 with non-native N-terminal signal peptide SEQ ID NO: 62. The non-native signal peptide is underlined. The remainder of the polypeptide is the VL domain amino acid sequence as denoted by IMGT. The N-terminal signal peptide is cleaved immediately before the position corresponding to IMGT residue 1 of the VL domain. Cleavage site is marked by chevron and is between IMGT residues −1 and 1. Cleavage generates a mature VL domain SEQ ID NO: 97 in which the N-terminal residue corresponds to IMGT position 1. The generated VL domain has the amino acid sequence of the 0128L VL domain.

(C) Processing of the amino acid sequence of a polypeptide SEQ ID NO: 66 comprising a VL domain SEQ ID NO: 101 with non-native N-terminal signal peptide SEQ ID NO:

62, wherein the residue corresponding to IMGT position 1 is deleted. The non-native signal peptide is underlined. The native N-terminal signal peptide is underlined. The remainder of the polypeptide is the VL domain amino acid sequence as denoted by IMGT except that there is no amino acid present at IMGT position 1. The N-terminal signal peptide is cleaved immediately before the position corresponding to IMGT residue 2 of the VL domain. Cleavage site is marked by chevron. Cleavage generates a mature VL domain SEQ ID NO: 101 in which the N-terminal residue corresponds to IMGT position 2. The amino acid sequence of this mature VL domain is identical to the amino acid sequence of the mature VL domain generated in (A), i.e., the 0325L VL domain.

FIG. 2 shows the amino acid sequence of VL domain 0325L. IMGT numbering is shown alongside. The 0325L VL domain is derived from recombination of human vλ gene segment IGLV3-21*d01 and human jλ gene segment IGLJ2*01.

FIG. 3 shows FXase activities for bispecific antibodies in the FXase assay, measured at 500 seconds. IXAX bispecific antibodies were expressed from nucleic acid encoding anti-FIX N1280H heavy chain, anti-FX heavy chain comprising the specified VH domain, and 0128L common light chain with non-native mouse κ leader (left) or human vλ3-21 leader (right). Human vλ3-21 leader is native to 0128L which is derived from recombination of human vλ gene segment IGLV3-21*d01 and human jλ gene segment IGLJ2*01.

FIG. 4 shows FXase activities for bispecific antibodies in the FXase assay, measured at (A) 570 seconds and (B) 600 seconds. In (A), data shown are for bispecific antibodies with heavy chains comprising N1280H VH domain and T0736H VH domain plus light chains comprising the following VL domains (left to right): N0128L from expression with native λ leader; N0310L; N0311L; N0312L; N0313L; N0314L; N0315L; N0316L; N0317L; N0318L; N0319; N0320L; N0321L; N0322L; N0323L; N0324L; N0325L; N0326L; N0327L; N0328L, N0329L; emicizumab positive control. All of N310L-N329L are from expression with codon-optimised mouse kappa leader. In (B), data shown are for bispecific antibodies with heavy chains comprising N1280H VH domain and T0736H VH domain plus light chains comprising the following VL domains (left to right): N0310L; N0311L; N0312L; N0313L; N0314L; N0315L; N0316L; N0317L; N0318L; N0319; N0320L; N0321L; N0322L; N0323L; N0324L; N0325L; N0326L; N0327L; N0328L, N0329L; N0128L from expression with native λ leader; emicizumab positive control. All of N310L-N329L are from expression with codon-optimised mouse kappa leader.

Figure 5:
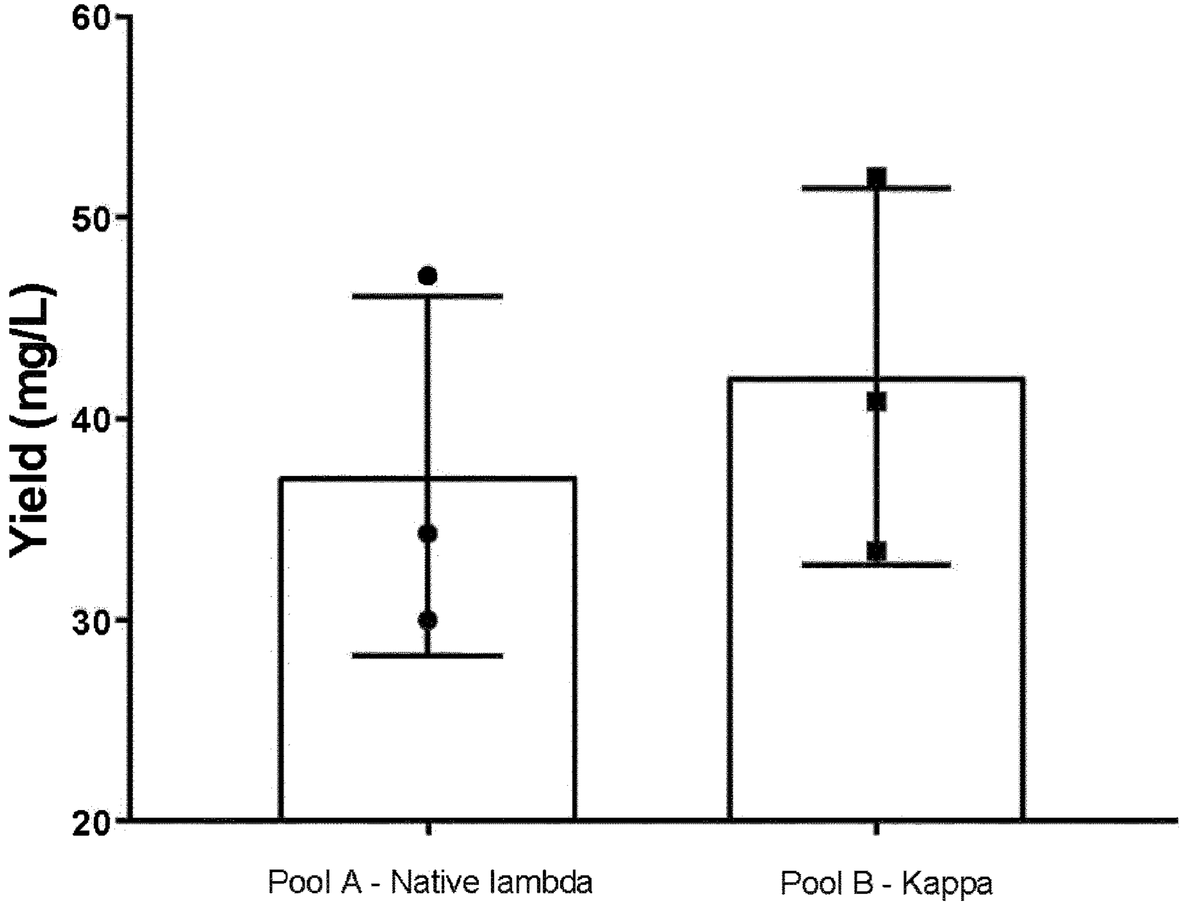

FIG. 5 shows a comparison of yield from bispecific antibodies expressed with a common light chain sequence comprising 0128L VL domain and a native lambda signal peptide (Pool A, left) or a non-native mouse kappa signal peptide (Pool B, right). Codon-optimised leader nucleotide sequences were used. Heavy chain sequences are heavy chain comprising N1172H VH domain and heavy chain comprising T0201H VH domain. Antibodies were expressed in CHO cells selected using 75 μM MSX and data are obtained from 35 ml samples after protein A purification post-dialysis into PBS.

Tables are presented at the end of the description.

DETAILED DESCRIPTION

Signal Peptide

Many eukaryotic polypeptides are expressed with an N-terminal sequence which directs the nascent polypeptide to the membrane of the endoplasmic reticulum (ER). This N-terminal sequence is typically referred to as a "signal peptide" or "leader". At the ER membrane, the N-terminal sequence is cleaved by signal peptidase and the polypeptide lacking the N-terminal sequence is translocated through the membrane and will either be secreted from the cell or displayed as a membrane protein on the cell surface. The expressed polypeptide, lacking the signal peptide, may be referred to as a mature polypeptide.

Where a polypeptide has a signal peptide, cleavage of the signal peptide ordinarily creates the new N-terminus of the mature polypeptide. Thus, the amino acid residue immediately following the cleavage site becomes the N-terminal residue of the mature polypeptide. Further modification of the amino acid sequence may occur with some polypeptides, so that the mature polypeptide comprises further alterations, but this does not generally occur with antibody light chains. Thus, the polypeptide sequence lacking the signal peptide represents the mature polypeptide which is expressed by the cell. A polypeptide may thus comprise a signal peptide which is directly fused to a VL domain, wherein the signal peptide represents the N-terminal sequence of the polypeptide. The VL domain may represent the remainder of the polypeptide, or further residues and/or further domains may be included C-terminal to the VL domain. For example the polypeptide may be an antibody light chain comprising a CL domain.

At the genomic level, the signal peptide is encoded within the gene for the polypeptide. While signal peptides of different polypeptides share some common structural characteristics, they are not all identical in sequence. In the case of the variable region gene segments from which antibody variable domains are derived, each variable region gene segment of the genome has its own signal peptide. The signal peptide of a variable region gene segment in genomic DNA may be referred to as the native or germline signal peptide for that gene segment.

For recombinant gene expression, where a coding sequence is introduced into a host cell in vitro, it is common to replace the native signal peptide. The coding sequence for the mature polypeptide is thus fused to a signal peptide which is different from the native signal peptide, although it may optionally be from the same polypeptide family, e.g., in the case of an antibody VL domain it may be a signal peptide for a different v gene segment. Although the non-native signal peptide has a different amino acid sequence from the native signal peptide, the person skilled in the art expects the sequence of the mature polypeptide to be identical regardless of which signal peptide is used, since the signal peptide is cleaved from the mature polypeptide. As taught herein, in fact differences in signal peptide sequence can result in differences in mature VL domains when expressing λ antibodies. Embodiments of the present invention use a non-native or heterologous signal peptide comprising a nucleotide sequence which differs from that of the native or germline signal peptide of the vλ gene segment. The signal peptide is optionally not a v λ signal peptide.

Examples of signal peptides are shown in appended Table P. MAWTALLLGLLSHCTGSVT (SEQ ID NO: 60) is the native signal peptide for the v gene segment vλ3-21. All other signal peptide amino acid sequences shown in Table P represent examples of non-native signal peptides for a VL domain derived from vλ3-21. Codon-optimised variants of encoding nucleotide sequences may be used. Thus a coding sequence for a VL domain may be fused to an upstream nucleotide sequence encoding the non-native leader. A preferred signal peptide is MSVPTQVLGLLLLWLTDARC (SEQ ID NO: 62). For CHO cell expression, a preferred nucleotide sequence encoding this signal peptide is ATGTCTGTGCCTACACAGGTTCTGGGACTGCTGC TGC TGTGGCTGACCGACGCCAGATGT (SEQ ID NO: 64), which is codon-optimised for expression in CHO cells.

Antibodies

Antibodies are immunoglobulins or molecules comprising immunoglobulin domains. Antibodies may be IgG, IgM, IgA, IgD or IgE molecules or molecules including antigen-specific antibody fragments thereof. The term "antibody" covers any polypeptide or protein comprising an antibody antigen-binding site. An antibody antigen-binding site (paratope) is the part of an antibody that binds to and is complementary to the epitope of its target antigen. The term "epitope" refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulphonyl groups, and, in certain embodiments, may have specific three-dimensional structural characteristics, and/or specific charge characteristics.

An antibody antigen-binding site is provided by a set of complementarity determining regions (CDRs) in an antibody VH and/or VL domain, and is capable of binding the antigen. In an example, the antibody binding site is provided by a single variable domain, e.g., a heavy chain variable domain (VH domain) or a light chain variable domain (VL domain). In another example, the binding site is provided by a VH/VL pair (an Fv) or two or more such pairs.

The antibody variable domains are the portions of the light and heavy chains of antibodies that include amino acid sequences of complementarity determining regions (CDRs; ie., CDR1, CDR2, and CDR3), and framework regions (FRs). Thus, within each of the VH and VL domains are CDRs and FRs. A VH domain comprises a set of HCDRs, and a VL domain comprises a set of LCDRs. VH refers to the variable domain of the heavy chain. VL refers to the variable domain of the light chain. Each VH and VL is typically composed of three CDRs and four FRs, arranged from amino-terminus to carboxy-terminus in the following order: FR1, CDR1, FR2, CDR2, FR3, CDR3, FR4. Amino acid positions assigned to CDRs and FRs may be defined according to IMGT nomenclature. An antibody may comprise an antibody VH domain comprising a VH CDR1, CDR2 and CDR3 and a framework. It may alternatively or also comprise an antibody VL domain comprising a VL CDR1, CDR2 and CDR3 and a framework. Example sequences of antibody VH and VL domains and CDRs form part of the present disclosure. The CDRs are defined according to the IMGT system.

An antibody may comprise one or more CDRs, e.g. a set of CDRs, within an antibody framework. The framework regions may be of human germline gene segment sequences. Thus, the antibody may be a human antibody having a VH domain comprising a set of HCDRs in a human germline framework and a VL domain comprising a set of LCDRs, e.g. in a human germline framework.

An antibody "gene segment", e.g., a VH gene segment, D gene segment, or JH gene segment refers to oligonucleotide having a nucleic acid sequence from which that portion of an antibody is derived, e.g., a VH gene segment is an oligonucleotide comprising a nucleic acid sequence that corresponds to a polypeptide VH domain from FR1 to part of CDR3. Human v, d and j gene segments recombine to generate the VH domain, and human v and j segments recombine to generate the VL domain. The D domain or region refers to the diversity domain or region of an antibody chain. J domain or region refers to the joining domain or region of an antibody chain. Recombination of germline v d and j gene segments at an immunoglobulin heavy chain locus in the genomic DNA of a developing B cell generates DNA encoding the heavy chain. Recombination of germline vκ and jλ gene segments at the immunoglobulin κ light chain locus in the genomic DNA of a developing B cell generates DNA encoding a κ light chain. If recombination at the κ locus fails to generate a productive light chain, then the λ locus rearranges. Recombination of germline vλ and jλ gene segments at the immunoglobulin λ light chain locus in the genomic DNA of the developing B cell generates DNA encoding a λ light chain. The heavy chain assembles with either the κ or λ chain to generate an antibody.

Somatic hypermutation may result in an antibody VH or VL domain having framework regions that do not exactly match or align with the corresponding germline gene segments, but sequence alignment can be used to identify the closest gene segments and thus identify from which particular combination of gene segments a particular VH or VL domain is derived. When aligning antibody sequences with gene segments, the antibody amino acid sequence may be aligned with the amino acid sequence encoded by the gene segment, or the antibody nucleotide sequence may be aligned directly with the nucleotide sequence of the gene segment.

Sequences from human λ v gene segments are provided in Table L and Table N herein for reference.

An antibody may be a whole immunoglobulin, including constant regions, or may be an antibody fragment. An antibody fragment is a portion of an intact antibody, for example comprising the antigen binding and/or variable region of the intact antibody. The antibody fragment may include one or more constant region domains.

An antibody of the invention may be a human antibody or a chimaeric antibody comprising human variable regions and non-human (e.g., mouse) constant regions. The antibody of the invention for example has human variable regions, and optionally also has human constant regions.

Thus, antibodies optionally include constant regions or parts thereof, e.g., human antibody constant regions or parts thereof, such as a human IgG4 constant region. For example, a VL domain may be attached at its C-terminal end to antibody light chain kappa or lambda constant domains. Similarly, an antibody VH domain may be attached at its C-terminal end to all or part (e.g. a CH1 domain or Fc region) of an immunoglobulin heavy chain constant region derived from any antibody isotype, e.g. IgG, IgA, IgE and IgM and any of the isotype sub-classes, such as IgG1 or IgG4. Examples of antibody constant regions are shown in Table S.

Digestion of whole (bivalent) immunoglobulins with the enzyme papain results in two identical (monovalent) antigen-binding fragments known as "Fab" fragments, and an "Fc" fragment. The Fc has no antigen-binding activity but has the ability to crystallize. "Fab" when used herein refers to a fragment of an antibody that includes one constant and one variable domain of each of the heavy and light chains. The term "Fc region" herein is used to define a C-terminal region of an immunoglobulin heavy chain, including native-sequence Fc regions and variant Fc regions. The "Fc fragment" refers to the carboxy-terminal portions of both H chains held together by disulphides.

Digestion of antibodies with the enzyme pepsin results in a bivalent F(ab')2 fragment in which the two arms of the antibody molecule remain linked. The F(ab')2 fragment is a bivalent fragment including two Fab fragments linked by a disulphide bridge at the hinge region. Single-chain antibodies (e.g., scFv) are another fragment. Two different monovalent monospecific antibody fragments such as scFv may be linked together to form a bivalent bispecific antibody.

"Fv" when used herein refers to the minimum fragment of an antibody that retains both antigen-recognition and antigen-binding sites. This region consists of a dimer of one heavy and one light chain variable domain in tight, non-covalent or covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognise and bind antigen, although usually at a lower affinity than the entire binding site.

An antibody may be a multispecific antibody, e.g., it may be a bispecific antibody comprising antigen-binding domains for two different antigens, wherein both antigen binding domains are formed by a VH/VL pair. Example multispecific antibody formats include FIT-Ig (see WO2015/103072), mAb-dAb, dock and lock, Fab-arm exchange, SEEDbody, Triomab, LUZ-Y, Fcab, Kλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, Triple body, Miniantibody, minibody, scFv-CH3 KIH, scFv-CH-CL-scFv, F(ab')2-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG(L,H)-Fv, IgG(H)-V, V(H)—IgG, IgG(L)-V, V(L)-IgG, KIH IgG-scFab, 2scFv-IgG, IgG-2scFv and scFv4-Ig.

In one embodiment, the bispecific antibody is a bispecific IgG comprising a first antigen-binding polypeptide arm and a second antigen-binding polypeptide arm, each polypeptide arm comprising a heavy chain and a light chain. The IgG is a tetrameric immunoglobulin comprising

- a first pair of antibody heavy and light chains (heavy-light chain pair) comprising a first antigen-binding Fv region,
- a second heavy-light chain pair comprising a second antigen-binding Fv region,
- wherein each heavy chain comprises a VH domain and a constant region, and each light chain comprises a VL domain and a constant region, and wherein the first and second heavy-light chain pairs associate through heterodimerisation of their heavy chain constant regions to form the immunoglobulin tetramer.

Optionally, the heavy chain constant region of the first heavy-light chain pair comprises a different amino acid sequence from the heavy chain constant region of the second heavy-light chain pair, wherein the different amino acid sequences are engineered to promote heterodimerisation of the heavy chain constant regions (e.g., they may comprise knobs-into-holes mutations or charge pair mutations). In one embodiment, the heavy chain constant region of one (e.g., the first) heavy-light chain pair is a human IgG4 constant region comprising substitution K439E and wherein the heavy chain constant region of the other (e.g., the second) heavy-light chain pair is an IgG4 region comprising substitution E356K, wherein constant region numbering is according to the EU numbering system. Examples of antibody constant regions and antibody heavy chains comprising them are provided in Table S.

Optionally, the two polypeptide arms comprise a common light chain, so the light chain of the first and second heavy-light chain pairs has an identical amino acid sequence Alternatively the two polypeptide arms may comprise different light chains.

Optionally a bispecific antibody is monovalent for binding each antigen.

Examples of bispecific antibodies include antibodies that bind coagulation factor IX and factor X. Nomenclature of bispecific antibodies which have a common light chain is IXAX-nnnn.tttt.llll, wherein nnnn is a 4 digit numerical identifier of the anti-FIX VH domain, tttt is a 4 digit identifier of the anti-FX VH domain, and llll is a 4 digit numerical identifier of the common VL domain. Sequences are shown in appended Table S and elsewhere herein.

Preferably, a common light chain comprises the 0128L VL domain or the 0325L VL domain. It may be the 0128L light chain sequence or the 0325L light chain sequence shown in Table S.

A bispecific antibody may comprise a FIX-binding arm comprising a heavy chain comprising the N0128H VH domain (e.g., the N0128H heavy chain). Alternatively, a bispecific antibody may comprise a FIX-binding arm comprising a heavy chain comprising the N1441H VH domain, the N1442H VH domain, the N1454H VH domain or the N1172H VH domain.

A bispecific antibody may comprise a FX-binding arm comprising a heavy chain comprising the T0201H VH domain (e.g., the T0201H heavy chain). Alternatively. a bispecific antibody may comprise a FX-binding arm comprising a heavy chain comprising the T0999H VH domain or the T0736H VH domain.

Preferred embodiments of bispecific antibodies are the following IgG:

- IXAX-1280.0999.0325 (anti-FIXa VH domain N1280H; anti-FX VH domain T0999H; 0325L common VL domain)
- IXAX-1441.0999.0325 (anti-FIXa VH domain N1441H; anti-FX VH domain T0999H; 0325L common VL domain).

The first heavy chain may be the N1280H heavy chain or the N1441H heavy chain. The second heavy chain may be the T0999H heavy chain. The light chain may be the 0325L λ light chain.

A bispecific antibody that binds FIXa and FX and catalyses FIXa-mediated activation of FX may comprise two immunoglobulin heavy-light chain pairs, wherein

- a first heavy-light chain pair comprises a FIXa binding Fv region comprising a first VH domain paired with a first VL domain, and
- a second heavy-light chain pair comprises a FX binding Fv region comprising a second VH domain paired with a second VL domain, wherein
- the first VH domain has at least 95% amino acid sequence identity with the N1280H VH domain,
- the second VH domain has at least 95% amino acid sequence identity with the T0201H VH domain, and the first VL domain and the second VL domain each have at least 95% amino acid sequence identity with the 0325L VL domain.

A bispecific antibody that binds FIXa and FX and catalyses FIXa-mediated activation of FX may comprise two immunoglobulin heavy-light chain pairs, wherein a first heavy-light chain pair comprises a FIXa binding Fv region comprising a first VH domain paired with a first VL domain, wherein the first VH domain is the N1280H VH domain, and a second heavy-light chain pair comprises a FX binding Fv region comprising a second VH domain paired with a second VL domain, wherein the second VH domain is the T0999H VH domain, and wherein the first and second heavy-light chain pairs each comprise a common light chain comprising the 0325L VL domain.

A bispecific antibody that binds FIXa and FX and catalyses FIXa-mediated activation of FX may comprise two immunoglobulin heavy-light chain pairs, wherein a first heavy-light chain pair comprises a FIXa binding Fv region comprising a first VH domain paired with a first VL domain, wherein the first VH domain is the N1441H VH domain, and a second heavy-light chain pair comprises a FX binding Fv region comprising a second VH domain paired with a second VL domain, wherein the second VH domain is the T0999H VH domain, and wherein the first and second heavy-light chain pairs each comprise a common light chain comprising the 0325L VL domain.

IMGT Numbering

The IMGT system is described in Lefranc, M.-P. et al., Dev. Comp. Immunol., 27, 55-77 2003. Unless otherwise indicated, numbering of antibody polypeptides used herein is IMGT numbering and structural definitions antibody VH domains, VL domains, CDRs and FRs are according to IMGT. Table L shows VL domain amino acid sequences translated from encoding vλ gene segments with reference to the IMGT system. FIG. 2 shows IMGT numbering for λ VL domain 0325L.

Encoding Nucleic Acids and Methods of Expression

Isolated nucleic acid may be provided, encoding polypeptides comprising antibody VL domains and light chains, and antibodies comprising them, according to the present invention. Nucleic acid may be DNA and/or RNA. Genomic DNA, cDNA, mRNA or other RNA, of synthetic origin, or any combination thereof can encode an antibody.

The present invention provides constructs in the form of plasmids, vectors, transcription or expression cassettes which comprise at least one polynucleotide as above. Exemplary nucleotide sequences are shown herein. Reference to a nucleotide sequence as set out herein encompasses a DNA molecule with the specified sequence, and encompasses an RNA molecule with the specified sequence in which U is substituted for T, unless context requires otherwise.

The present invention also provides a recombinant host cell that comprises one or more nucleic acids encoding the polypeptide or antibody. Methods of producing the encoded molecule may comprise expression from the nucleic acid, e.g., by culturing recombinant host cells containing the nucleic acid. The polypeptide or antibody may thus be obtained, and may be isolated and/or purified using any suitable technique, then used as appropriate. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals.

The expression of antibodies and antibody fragments in prokaryotic cells is well established in the art. A common bacterial host is *E. coli*. Expression in eukaryotic cells in culture is also available to those skilled in the art as an option for production. Mammalian cell lines available in the art for expression of a heterologous polypeptide include Chinese hamster ovary (CHO) cells, HeLa cells, baby hamster kidney cells, NSO mouse melanoma cells, YB2/0 rat myeloma cells, human embryonic kidney (HEK) cells, human embryonic retina cells and many others. CHO, NS0, Sp2/0, HEK293 and PERC6 are commonly used (Dumont et al., Crit Rev Biotechnol 36(6): 1110-1122 2016).

A popular system for recombinant expression of biopharmaceuticals is Lonza's GS System™. Glutamine synthetase (GS) is the enzyme responsible for the biosynthesis of glutamine from glutamate and ammonia. In the absence of glutamine in the growth medium, the GS enzyme is essential for the survival of mammalian cells in culture. Some mammalian cell lines, such as mouse myeloma lines, do not express sufficient GS to survive without added glutamine. With these cell lines, a transfected GS gene can function as a selectable marker by permitting growth in a glutamine-free medium. Other cell lines, such as CHO cell lines, express sufficient GS to survive without exogenous glutamine. In these cases, the GS inhibitor, methionine sulphoximine (MSX), can be used to inhibit endogenous GS activity such that only transfectants with additional GS activity can survive. Lonza supplies vectors comprising nucleic acid encoding GS and a cloning site into which antibody sequences can be inserted, for transfection into host cells which are then selected for integration of the desired genes. Lonza offers a CHOK1SV host cell line, although other host cells such as CHOK1 may be used.

Vectors may contain appropriate regulatory sequences, including promoter sequences, terminator sequences, polyadenylation sequences, enhancer sequences, marker genes and other sequences as appropriate. Promoters and other regulatory elements for recombinant gene expression recently reviewed by Gupta et al., Biotechnology Advances 2019. A promoter and/or other element identified in Table 1 of Gupta et al., 2019 may be used in the present invention.

Nucleic acid encoding a polypeptide or antibody can be introduced into a host cell. Nucleic acid can be introduced to eukaryotic cells by various methods, including calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques include calcium chloride transformation, electroporation and transfection using bacteriophage. The introduction may be followed by expressing the nucleic acid, e.g., by culturing host cells under conditions for expression of the gene, then optionally isolating or purifying the antibody.

Nucleic acid of the invention may be integrated into the genome (e.g. chromosome) of the host cell. Integration may be promoted by inclusion of sequences that promote recombination with the genome, in accordance with standard techniques. Nucleic acid encoding a polypeptide or antibody may be integrated into genomic DNA of a host (e.g., CHO) cell, e.g., into chromosomal DNA, and the resulting recombinant cell may be cultured to express the polypeptide or antibody. A cell line development process may comprise introducing nucleic acid encoding the polypeptide or antibody into multiple host cells, and selecting a cell line which expresses a desired level of polypeptide or antibody at the desired yield (e.g., at least 0.5 g/L or at least 1 g/L). Preferably the cell line will retain stable expression over a number of generations in cell culture, and thus it may maintain these levels of production over at least 60 generations for example.

The present invention also provides a method that comprises using nucleic acid described herein in an expression system in order to express the polypeptide or antibody. Desirably, the polypeptide or antibody is expressed at a yield of at least 0.5 g/L in the cell supernatant after initial fermentation, preferably at a yield of >2 g/L. Solubility should be >10 mg/ml, preferably >50 mg/ml, without significant aggregation or degradation of the molecules.

To provide medicines suitable for global treatment, antibodies can be produced on a large scale, for instance in cell culture volumes of at least 100 litres or at least 200 litres, e.g., between 100-250 litres. Batch culture, particularly fed-batch culture, is now commonly used for production of biotherapeutics for clinical and commercial use, and such methods may suitably be used in the present invention to generate the antibodies, followed by purification and formulation steps as noted herein. Bioreactors may be metal (e.g., stainless steel) vessels or may be single-use bioreactors.

Formulation and Administration

A polypeptide or antibody according to the present invention, and its encoding nucleic acid, will usually be provided in isolated form. VL domains, antibody light chains, antibodies and nucleic acids may be provided purified from their natural environment or their production environment. Isolated polypeptides and isolated nucleic acid will be free or substantially free of material with which they are naturally associated, such as other polypeptides or nucleic acids with which they are found in vivo, or the environment in which they are prepared (e.g., cell culture) when such preparation is by recombinant DNA technology in vitro. Optionally an isolated polypeptide or nucleic acid (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature.

A polypeptide or antibody may be purified (e.g., from cell culture supernatant) by protein A chromatography and/or ion exchange chromatography. Optionally, a bispecific antibody is be produced by a method comprising

- expressing two antibody heavy chains and common light chain from cultured host cells comprising encoding nucleic acids,
- obtaining cell culture comprising the bispecific antibody and monospecific antibodies assembled from the antibody heavy chains and common light chain,
- isolating the bispecific antibody and monospecific antibodies from the cell culture (e.g., using protein A chromatography), and
- purifying the bispecific antibody from the monospecific antibodies (e.g., using cation exchange chromatography).

Antibodies or their encoding nucleic acids may be formulated with diluents or adjuvants and still for practical purposes be isolated—for example they may be mixed with carriers if used to coat microtitre plates for use in immunoassays, and may be mixed with pharmaceutically acceptable carriers or diluents when used in therapy. As described elsewhere herein, other active ingredients may also be included in therapeutic preparations. Antibodies may be glycosylated, either naturally in vivo or by systems of heterologous eukaryotic cells such as CHO cells, or they may be (for example if produced by expression in a prokaryotic cell) unglycosylated. The invention encompasses antibodies having a modified glycosylation pattern.

Typically, an isolated product constitutes at least about 5%, at least about 10%, at least about 25%, or at least about 50% of a given sample. An antibody may be substantially free from proteins or polypeptides or other contaminants that are found in its natural or production environment that would interfere with its therapeutic, diagnostic, prophylactic, research or other use.

As discussed elsewhere herein, expression of antibody heavy and light chains for a bispecific antibody may generate unwanted homodimeric species in addition to the active heterodimeric bispecific antibody (e.g., for a bispecific antibody for FIX and FX, homodimers would be anti-FIX and anti-FX antibodies). Preferably a bispecific is provided in a composition in which the heterodimeric bispecific antibody is represents at least 95% of the total antibody, with homodimeric antibody contaminants being present at 5% or less. The composition may comprise at least 98% or at least 99% heterodimeric bispecific, with homodimeric contaminants representing 0-2% or 0-1% respectively.

The invention provides therapeutic compositions comprising the antibodies described herein. Therapeutic compositions comprising nucleic acid encoding such antibodies are also provided. Encoding nucleic acids are described in more detail elsewhere herein and include DNA and RNA, e.g., mRNA. Cells containing nucleic acid encoding the antibody, optionally wherein the nucleic acid is stably integrated into the genome, thus represent medicaments for therapeutic use in a patient. Nucleic acid encoding the antibody may be introduced into human cells derived from the intended patient and modified ex vivo. Administration of cells containing the encoding nucleic acid to the patient provides a reservoir of cells capable of expressing the antibody, which may provide therapeutic benefit over a longer term compared with administration of isolated nucleic acid or the isolated antibody. Nucleic acid encoding the antibody may be provided for use in gene therapy, comprising introducing the encoding nucleic acid into cells of the patient in vivo, so that the nucleic acid is expressed in the patient's cells and provides a therapeutic effect.

Compositions may contain suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPO- FECTINT™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311. Compositions may comprise the antibody or nucleic acid in combination with medical injection buffer.

Antibodies or their encoding nucleic acids, may be formulated for the desired route of administration to a patient, e.g., in liquid (optionally aqueous solution) for injection.

Various delivery systems are known and can be used to administer the pharmaceutical composition of the invention. Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The antigen-binding molecules are preferably administered by subcutaneous injection.

The pharmaceutical composition can be also delivered in a vesicle, in particular a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used; see, Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule. A pharmaceutical composition of the present invention can be delivered subcutaneously or intravenously with a standard needle and syringe. It is envisaged that treatment will not be restricted to use in the clinic. Therefore, subcutaneous injection using a needle-free device is also advantageous. With respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded. Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPENT™, OPTIPEN PRO™, OPTIPEN STARLET™, and OPTICLIKT™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly).

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, the aforesaid antibody may be contained in about 5 to about 100 mg and in about 10 to about 250 mg for the other dosage forms.

The antibody, nucleic acid, or composition comprising it, may be contained in a medical container such as a phial, syringe, IV container or an injection device. In an example, the antibody, nucleic acid or composition is in vitro, and may be in a sterile container. In an example, a kit is provided comprising the antibody, packaging and instructions for use in a therapeutic method as described herein.

One aspect of the invention is a composition comprising a polypeptide, antibody or nucleic acid of the invention and one or more pharmaceutically acceptable excipients, examples of which are listed above. "Pharmaceutically acceptable" refers to approved or approvable by a regulatory agency of the USA Federal or a state government or listed in the U.S. Pharmacopeia or other generally recognized pharmacopeia for use in animals, including humans. A pharmaceutically acceptable carrier, excipient, or adjuvant can be administered to a patient, together with any antibody or polypeptide molecule described herein, and does not destroy the pharmacological activity thereof and is nontoxic when administered in doses sufficient to deliver a therapeutic amount of the agent.

In some embodiments, the polypeptide or antibody will be the sole active ingredient in a composition according to the present invention. Thus, a composition may consist of the antibody or it may consist of the antibody with one or more pharmaceutically acceptable excipients. However, compositions according to the present invention optionally include one or more additional active ingredients.

CLAUSES

The following numbered clauses present embodiments of the invention and are part of the description.

1. A polypeptide comprising an antibody light chain variable (VL) domain with an N-terminal signal peptide, wherein
   - the VL domain comprises a sequence derived from a v λ gene segment and a sequence derived from a j gene segment, wherein
   - the N-terminal signal peptide differs from the native N-terminal signal peptide for said λ v gene segment, and wherein
   - the residue corresponding to IMGT position 1 of the VL domain is absent.
2. A polypeptide according to clause 1, wherein the v λ gene segment is a human v λ gene segment.
3. A polypeptide according to clause 1 or clause 2, wherein the j gene segment is a human j λ gene segment.
4. A polypeptide according to any of clauses 1 to 3, wherein the first encoded residue (IMGT position 1) of the v λ gene segment is Ser.
5. A polypeptide according to any of clauses 1 to 3, wherein the v λ gene segment is a vertebrate IGLV3 family gene segment.
6. A polypeptide according to clause 5, wherein the v λ gene segment is IGLV3-21, IGLV3-1, IGLV3-9, IGLV3-10, IGLV3-12, IGLV3-13, IGLV3-16, IGLV3-19, IGLV3-22, IGLV3-25 or IGLV3-27.
7. A polypeptide according to clause 5 or clause 6, wherein the first two encoded residues (IMGT positions 1 to 2) of the v λ gene segment are Ser Tyr.
8. A polypeptide according to clause 7, wherein the first three encoded residues (IMGT positions 1 to 3) of the v λ gene segment are Ser Tyr Val.
9. A polypeptide according to clause 6 or clause 7, wherein the v λ gene segment is human IGLV3-21.
10. A polypeptide according to any preceding clause, wherein the signal peptide has a length of 20 amino acids.
11. A polypeptide according to any preceding clause, wherein the signal peptide is not a human λ v gene segment signal peptide.
12. A polypeptide according to clause 11, wherein the signal peptide is not a λ v gene segment signal peptide.
13. A polypeptide according to any preceding clause, wherein the signal peptide comprises a C-terminal Cys residue.
14. A polypeptide according to clause 13, wherein the signal peptide comprises a C-terminal sequence Ala Arg Cys.
15. A polypeptide according to clause 14, wherein the signal peptide comprises a C-terminal sequence Thr Asp Ala Arg Cys.
16. A polypeptide according to any preceding clause, wherein the signal peptide is a κ V gene segment signal peptide.
17. A polypeptide according to clause 16, wherein the signal peptide is a mouse κ V gene segment signal peptide.
18. A polypeptide according to clause 17, wherein the signal peptide is

SEQ ID NO: 62

MSVPTQVLGLLLLWLTDARC.

19. A polypeptide according to any preceding clause, wherein the polypeptide is an antibody light chain comprising the VL domain and a light chain constant (CL) domain.
20. A polypeptide according to clause 19, wherein the CL domain is a λCL domain.
21. A polypeptide according to any preceding clause, wherein the VL domain is the N0325L VL domain.
22. A polypeptide according to clause 21, consisting of amino acid sequence

SEQ ID NO: 66

MSVPTQVLGLLLLWLTDARCYVLTQPPSVSVAPGETARITCGGDNIGRK
SVYWYQQKSGQAPVLVIYYDSDRPSGIPERFSGSNSGNTATLTISRVEA
GDEADYYCQVWDGSSDHWVFGGGTKLTVL or comprising said sequence as an N-terminal domain.

23. A polypeptide according to clause 22, which is an antibody λ light chain consisting of or comprising amino acid sequence

SEQ ID NO: 67

MSVPTQVLGLLLLWLTDARCYVLTQPPSVSVAPGETARITCGGDNIGRK
SVYWYQQKSGQAPVLVIYYDSDRPSGIPERFSGSNSGNTATLTISRVEA
GDEADYYCQVWDGSSDHWVFGGGTKLTVLGQPKAAPSVTLFPPSSEELQ
ANKATLVCLISDFYPGAVTVAWKADSSPVKAGVETTTPSKQSNNKYAAS
SYLSLTPEQWKSHKSYSCQVTHEGSTVEKTVAPTECS.

24. Nucleic acid encoding a polypeptide according to any preceding clause.
25. Nucleic acid according to clause 24, wherein the nucleic acid is cDNA.
26. Nucleic acid according to clause 24, wherein the nucleic acid is genomic DNA comprising introns.
27. Nucleic acid according to any of clauses 24 to 26, comprising nucleotide sequence ATGTCTGTGCCTACACAGGTTCTGGGACTGCTGCTGCTGTGGCTGACCGACGCCAGATGT SEQ ID NO: 64 encoding the signal peptide.
28. Nucleic acid according to any of clauses 24 to 27, comprising nucleotide sequence TACGTGCTGAC CCA GCCTCCTTCCGTGTCTGTTGCTCCTGGCGAGACA G CCAGAATCACC TGTGGCGGCGATAACATCGGCCGGAAGTCCGTGTACTGGTATCAGCAGAAGTCCGGCCA GGCTCCTGTGCTGGTCATCTACTACGACTCCGACCGGCCTTCTGGCATCCCTGAGAGATTCTCCGG CTCCAACTCCGGCAATACCGCCACACTGACCATCTCCAGAGTGGAAGCTGGCGA CGAGGCCGACTACTACTGCCAAGTGTGGGACGGCTCCTCTGACCACTGGGTTTTCGGCGG AGGCACCAAGCTGACAGTGCTG SEQ ID NO: 100 encoding the VL domain.

29. Nucleic acid according to clause 28, comprising nucleotide sequence

SEQ ID NO: 65

```
ATGTCTGTGCCTACACAGGTTCTGGGACTGCTGCTGCTGTGGCTGACCG
ACGCCAGATGTTACGTGCTGACCCAGCCTCCTTCCGTGTCTGTTGCTCC
TGGCGAGACAGCCAGAATCACCTGTGGCGGCGATAACATCGGCCGGAAG
TCCGTGTACTGGTATCAGCAGAAGTCCGGCCAGGCTCCTGTGCTGGTCA
TCTACTACGACTCCGACCGGCCTTCTGGCATCCCTGAGAGATTCTCCGG
CTCCAACTCCGGCAATACCGCCACACTGACCATCTCCAGAGTGGAAGCT
GGCGACGAGGCCGACTACTACTGCCAAGTGTGGGACGGCTCCTCTGACC
ACTGGGTTTTCGGCGGAGGCACCAAGCTGACAGTGCTG.
```

30. A host cell in vitro comprising nucleic acid according to any of clauses 24 to 29.

31. A cell according to clause 30 which is a mammalian cell.

32. A cell according to clause 31 which is a CHO cell.

33. A cell according to clause 31 which is a human cell.

34. A cell according to clause 33 which is a HEK cell.

35. A cell according to any of clauses 30 to 34, wherein said nucleic acid is integrated into chromosomal DNA of the cell.

36. An in vitro population of cells according to any of clauses 30 to 35.

37. A population of cells according to clause 36, wherein the cells express the encoded polypeptide, and wherein
on expression in the cells, the signal peptide is cleaved from the polypeptide to provide a mature VL domain comprising an N-terminal residue corresponding to IMGT position 2.

38. A method of expressing a polypeptide comprising a VL domain, the method comprising
culturing a population of cells according to clause 36 or clause 37 under conditions for expression of the polypeptide, wherein
the N-terminal signal peptide is cleaved off the VL domain to provide a polypeptide comprising a mature VL domain, wherein
the N-terminal residue of the polypeptide comprising the mature VL domain is IMGT position 2 of the VL domain.

39. A method of expressing an antibody comprising a VH domain and a VL domain, wherein the VL domain comprises a sequence derived from a v λ gene segment and a sequence derived from a j gene segment, the method comprising
providing a population of cells according to clause 36 or clause 37, wherein the cells further comprise nucleic acid encoding the VH domain,
culturing said population of cells under conditions for expression of the polypeptide comprising the VL domain and for expression of the VH domain, wherein
the N-terminal signal peptide is cleaved off the VL domain to provide a polypeptide comprising a mature VL domain, wherein
the N-terminal residue of the polypeptide comprising the mature VL domain is IMGT position 2 of the VL domain, and wherein
the VL domain assembles with the VH domain to provide said antibody.

40. A method according to clause 38 or clause 39, wherein the polypeptide or antibody is secreted from the cells.

41. A method according to any of clauses 38 to 40, comprising isolating the polypeptide or antibody from the population of cells.

42. A method according to clause 41, comprising purifying the polypeptide or antibody by one or more steps of protein chromatography.

43. A method according to any of clauses 38 to 42, wherein the antibody is an IgG.

44. A method according to any of clauses 38 to 43, wherein the antibody is a multispecific antibody.

45. A method of expressing a bispecific antibody comprising two heavy chains each comprising a different VH domain, and a common light chain comprising a VL domain, wherein the VL domain comprises a sequence derived from a v λ gene segment and a sequence derived from a j gene segment, the method comprising
providing a population of cells according to clause 36 or clause 37, wherein the cells further comprise nucleic acid encoding the two heavy chains,
culturing said population of cells under conditions for expression of the antibody heavy and light chains, wherein
the N-terminal signal peptide is cleaved off the VL domain to provide an antibody light chain comprising a mature VL domain, wherein
the N-terminal residue of the polypeptide comprising the mature VL domain is IMGT position 2 of the VL domain, and wherein
the light chain domain assembles with each of the two heavy chains to provide said bispecific antibody.

46. A method according to clause 45, wherein the two heavy chains comprise VH domains N1280H and T0999H respectively and wherein the light chain comprises VL domain 0325L.

47. A method according to clause 46, wherein the antibody is an IgG4 comprising the N1280H heavy chain, the T0999H heavy chain and the 0325L light chain.

48. A method according to clause 45, wherein the two heavy chains comprise VH domains N1441H and T0999H respectively and wherein the light chain comprises VL domain 0325L.

49. A method according to clause 46, wherein the antibody is an IgG4 comprising the N1441H heavy chain, the T0999H heavy chain and the 0325L light chain.

50. An antibody VL domain obtained by cleavage of the N-terminal signal peptide from the polypeptide of any of clauses 1 to 23.

51. An isolated antibody comprising a VL domain according to clause 50.

52. An isolated antibody obtained by the method of any of clauses 39 to 49.

53. An isolated antibody comprising a VH domain and a VL domain, wherein the VL domain comprises a sequence derived from a v λ gene segment and a sequence derived from a j gene segment, and wherein the N-terminal residue of the VL domain is the residue corresponding to IMGT position 2.

54. An antibody according to clause 53, wherein the v λ gene segment is a human Vλ3-21 gene segment.

55. An antibody according to clause 54, wherein the VL domain amino acid sequence is the 0325L VL domain amino acid sequence.

56. An antibody according to clause 55, wherein the antibody comprises a λ light chain wherein the amino acid sequence of said light chain is the 0325L light chain amino acid sequence.

57. An antibody according to any of clauses 53 to 56, which is a bispecific antibody comprising two heavy chains each comprising a different VH domain, and a common light chain comprising said VL domain.

58. An antibody according to clause 57, wherein the bispecific antibody comprises a heavy chain comprising the N1280H VH domain;

a heavy chain comprising the T0999H VH domain; and a common light chain comprising the 0325L VL domain.

59. An antibody according to clause 58, comprising the N1280H heavy chain, the T0999H heavy chain and the 0325L common light chain.

60. An antibody according to clause 57, wherein bispecific antibody comprises a heavy chain comprising the N1441H VH domain;

a heavy chain comprising the T0999H VH domain; and a common light chain comprising the 0325L VL domain.

61. An antibody according to clause 60, comprising the N1441H heavy chain, the T0999H heavy chain and the 0325L common light chain.

62. A method of formulating a pharmaceutical composition, comprising combining an antibody with a pharmaceutically acceptable excipient, wherein the antibody is an antibody according to any of clauses 51 to 61.

63. A method of producing, or of improving stability and/or antigen-binding of, an antibody comprising a VH domain and a VL domain, wherein the VL domain comprises a sequence derived from a v λ gene segment and a sequence derived from a j gene segment, the method comprising providing nucleic acid encoding said antibody, comprising a nucleotide sequence encoding said VL domain with an N-terminal signal peptide, wherein the codon for the residue corresponding to IMGT position 1 of said VL domain is deleted, N-terminal signal peptide is not the native N-terminal signal peptide for said λ v gene segment, and expressing said nucleic acid to provide an antibody comprising the VH domain and VL domain, wherein the N-terminal residue of the VL domain is the residue corresponding to IMGT position 2, and optionally isolating and purifying said antibody.

EXAMPLES

Example 1 Creation and Characterisation of λ Antibodies Including 0128L VL Domain Bispecific antibodies recognising coagulation factors IX and X (FIX and FX) were generated in IgG format. One arm of the IgG comprises a VH-VL domain pair specific for FIX and the other arm of the IgG comprises a VH-VL domain pair specific for FX. The bispecific antibodies comprise two different heavy chains, each with a different VH domain, and a common light chain comprising the 0128L VL domain which pairs with each of the two different VH domains. The 0128L VL domain was generated by immunisation of mice transgenic for human immunoglobulin heavy and λ light chain gene segments. Comparison of the nucleotide sequence encoding the 0128L VL domain with germline gene segments indicates that it was derived from recombination of human λ gene segments IGLV3-21*d01 and IGLJ2*01. Generation of the 0128L light chain was described in detail in WO2018/234575.

Bispecific antibodies comprising a common λ light chain including the 0128L VL domain were screened for FVIIIa-mimetic activity, i.e., ability to enhance (catalyse) the FIXa-mediated activation of FX to FXa in vitro by enzymatic "FXase" assay. In this assay, the test bispecific molecule is contacted with FIXa and FX in the presence of phospholipid, under conditions suitable for formation of FXa. A substrate for FXa is added which, when cleaved by FXa, generates a detectable product. Detection of this product in the presence of test bispecific antibody is compared with a negative control in which no test antibody is present (a control antibody may be included). The detected signal is quantified by recording absorbance of the reaction solution at 405 nm. Absorbance is measured across a range of antibody concentrations in the assay and an EC50 value is calculated as a measure of the bispecific antibody potency in this assay. Significant difference of EC50 between test antibody and control indicates that the test antibody is able to enhance FIXa-mediated activation of FX.

Antibodies tested in this assay were initially generated from expression of nucleic acid encoding the heavy and light chains with their native signal peptides. Thus, the 0128L light chain was expressed from nucleic acid encoding the 0128L VL domain with its native vλ3-21 leader. Antibodies were expressed in HEK cells.

Bispecific antibodies which showed strong activity in FXase assay were selected.

The nomenclature used herein for the anti-FIXxFX bispecific antibodies which have a common light chain is IXAX-nnnn.tttt.llll, wherein nnnn is a 4 digit numerical identifier of the anti-FIX VH domain, tttt is a 4 digit identifier of the anti-FX VH domain, and llll is a 4 digit numerical identifier of the common VL domain. Sequences of VH and VL domains and heavy and light chains of IXAX antibodies are shown in appended Table S and elsewhere herein.

Example 2 Expression of λ Antibody with Different Leader Sequences and 0128L VL Domain For industrial manufacturing it is common to transfer the coding sequence for the mature antibody polypeptides to a transfection vector comprising a leader sequence. The VL domain sequence is thus expressed with a non-native leader.

When we switched the native leader sequences of our bispecific antibodies to alternative leader sequences for manufacturing purposes, we observed a decrease in functional activity in the FXase assay. This was not the result of a change in antibody expression, which remained constant (see Example 7). Unexpectedly, we saw a drop in FVIII mimetic activity when a kappa light chain leader was used to express the 0128L common light chain.

In more detail, a panel of 21 bispecific antibodies comprising a range of different anti-FX heavy chains, each in combination with the N0128H anti-FIX heavy chain and 0128L common light chain were screened in the FXase assay. Two different 0128L common light chain constructs were used to express the N0128L common light chain, one with the native leader, and the other with a mouse kappa light chain leader. Sequences are shown in appended Table P.

The bispecific antibodies were expressed in HEK cells, using vectors encoding the anti-FIX and anti-FX heavy chains and the common light chain N0128_IgL with the selected light chain leader.

Bispecific antibodies were expressed using a high-throughput 2 ml deep-well block transfection method. Following expression and harvest, bispecific antibodies were purified from HEK media using Protein A chromatography, protein quantified by OD280 and all samples normalised for protein concentration.

A significant drop of FXa generation activities was observed in bispecific antibodies in which the mouse kappa light chain leader was used to express the common light chain, compared with those which the native leader was used to express the common light chain. FIG. 3.

Example 3 Identification of Leader-Dependent N-Terminal Clipping in 0128L

The structural integrity of therapeutic monoclonal antibodies can be compromised by multiple types of post-translational modifications which result in product heterogeneity. Mass spectrometry (MS) was used to characterise and evaluate the molecular mass of the bispecific antibodies after cation exchange purification.

Unexpectedly, mass spectrometry analysis of common light chain comprising 0128L which had been expressed with native human IgA leader sequence identified a specific clipping the N-terminal Ser occurring on the fully assembled bispecific antibody when compared to IMGT reference sequence. Notably, however, the non-native leader sequence retained the N terminal serine when analysed by mass spectrometry.

Bispecific antibody IXAX-1172.0201.0128 was expressed from nucleic acids encoding an anti-FIX heavy chain comprising the N1172H VH domain, an anti-FX heavy chain comprising the T0201H VH domain and a common light chain comprising the 0128L VL domain.

The antibody was expressed using either native leader or mouse kappa light chain leader for the common light chain, and the anti-FIX/anti-FX heterodimer was purified by cation exchange and analysed by mass spectrometry.

When the native leader was used to express the light chain, molecular weights (MW) of anti-FIX/anti-FX heterodimer determined by MS was smaller than the theoretical MW predicted by amino acid sequences of the IXAX-1172.0201.0128 anti-FIX/anti-FX heterodimer. MS results of the common light chain suggested that the N-terminal serine of the common light chain was truncated when native leader is used.

When mouse kappa light chain leader was used to express the light chain, MW of anti-FIX/anti-FX heterodimer determined by MS matched the theoretical MW predicted by amino acid sequences of the anti-FIX/anti-FX IXAX-1172.0201.0128 heterodimer. MS results of the common light chain suggested that the N-terminal serine of the common light chain was intact when the mouse kappa light chain leader is used.

These observations were consistent regardless of whether the bispecific antibody was expressed in either HEK or CHO cells.

Notably, we observed with the full length 0128L (including the N-terminal serine) that cleavage was either complete or not at all as determined by mass spectrometry, depending on which leader sequence was used. This contrasts with an earlier report of leader misprocessing (Gibson et al., 2017), in which a variable cleavage site was reported to account for low levels (4-6%) of truncated light chain in the recovered antibody product.

Example 4 Mutation Analysis at IMGT Position 1 of 0128L

We hypothesised that removal of the N-terminal serine in the presence of the new leader sequence would restore functional activity. We further investigated the effect of substituting different amino acid residues for the serine at IMGT position 1.

The heavy chains of the anti-FIX binding arm and the anti-FX binding arm of the bispecific antibody were "fixed" as the N1280H VH domain and the T0736H VH domain respectively, while further refinements were made to the common light chain VL domain to identify mutants that would retain the FXa generation activities of the bispecific antibodies when the mouse kappa light chain leader was used.

Table E below identifies mutants of the 0128L VL domain in which one or more residues of the CDRs are mutated to other amino acids. The table shows the name given to each variant VL domain having the identified mutation at IMGT position 1. In each case, residues other than IMGT position 1 were left unchanged. For example, the 0310L VL domain is a Ser1Ala mutant of the 0128L VL domain, i.e., in which the serine (S) at IMGT position 1 in Framework 1 is replaced by alanine (A). The 0325L VL domain is the 0128L VL domain with a deletion at IMGT position 1, i.e., it represents the 0128L VL domain with the N-terminal serine clipped off.

| VL domain variant of N0128L | IMGT residue 1 |
|---|---|
| N0310L | A |
| N0311L | C |
| N0312L | D |
| N0313L | E |
| N0314L | F |
| N0315L | G |
| N0316L | H |
| N0317L | I |
| N0318L | K |
| N0319L | L |
| N0320L | M |
| N0321L | N |
| N0322L | P |
| N0323L | Q |
| N0324L | R |
| N0325L | del |
| N0326L | T |
| N0327L | V |
| N0328L | W |
| N0329L | Y |
| N0128L | S |

Bispecific antibodies, purified by protein A chromatography, were tested for functional activity to look for maintenance of FXa generation activities of the parent bispecific comprising 0128L VL domain when the native leader is used. Newly generated bispecific antibodies were characterised in the FXase assay described in Example 1.

Mutagenesis of light chain framework 1 produced improvements in FVIII mimetic activity. N0325L, which compromises a deletion of the N-terminal serine, was the only mutant that maintained the FXa generation activities of the bispecific antibodies when the mouse kappa light chain leader was used. Bispecific comprising 0325L VL domain demonstrated activity comparable to that of the parent bispecific comprising 0128L VL domain when the native leader was used. FIG. 4.

Thus, in the presence of the alternative leader sequence, deletion of the N-terminal serine demonstrated greater biological activity compared to the same bispecific antibody with the N-terminal serine. This confirms the effect of serine N-terminal deletion on the functionality of the molecule in the presence of the alternative leader sequence.

Example 5 Expression of Antibody with 0325L VL Domain

Following identification of N0325L, a larger scale transient HEK Expi293 transfection was subsequently carried out at 30 ml, and IXAX bispecific antibodies produced in this HEK expression system confirmed the observations from the small-scale transfection (Example 2).

We also confirmed that IXAX bispecific antibodies with common light chains lacking the N-terminal serine expressed with a non-native leader demonstrated restored functional activity when expressed stably as CHO mini-pools.

Both HEK and CHO cell lines were used to express IXAX antibodies including the 0325L light chain with either native vλ3-21 leader or the non-native mouse κ leader. A codon-optimised leader nucleotide sequence was used (optimised for CHO, and the same sequence used in HEK).

Expression in HEK Cells

Briefly, $7.5\times10^7$ cells (final cell density of $2.5\times10^6$ cells/mL) were used for each 30 ml transfection and were incubated in a 37° C. incubator with a humidified atmosphere of 8% $CO_2$ in air on an orbital shaker rotating at 125-140 rpm for 1 hour. For each transfection sample, lipid-DNA complexes were prepared by mixing 30 μg of plasmid DNA in Opti-MEM® I medium to a total volume of 1.5 mL, followed by gentle mixing. Subsequently, 80 μL of ExpiFectamine™ 293 Reagent was diluted in Opti-MEM® I medium to a total volume of 1.5 mL, followed by gentle mixing. This mixture was incubated for 5 minutes at room temperature. After the 5 minute incubation, the DNA was added to the diluted ExpiFectamine™ 293 Reagent to obtain a total volume of 3 mL. This mixture was mixed gently and incubated for 20-30 minutes at room temperature to allow DNA-ExpiFectamine™ 293 Reagent complexes to form. Once the incubation has completed the DNA-ExpiFectamine™ 293 Reagent complex is added to each shake flask containing Expi293 cells. Cells are incubated in a 37° C. incubator with a humidified atmosphere of 8% $CO_2$ in air on an orbital shaker rotating at 125-140 rpm. Approximately 16-18 hours post-transfection, 150 μL of ExpiFectamine™ 293 Transfection Enhancer 1 and 1.5 mL of ExpiFectamine™ 293 Transfection Enhancer 2 is added to each flask. Supernatants were harvested 5 to 6 days post-transfection. Following expression and harvest, bispecific antibodies were purified from HEK media using Protein A chromatography, protein quantified by OD280 and samples normalised for protein concentration.

We confirmed IXAX bispecific antibodies with common light chains lacking the N-terminal serine expressed with a non-native leader demonstrated similar levels of functional activity to full-length common light chain expressed with a native leader in HEK cells regardless whether the expression scale was small (2 ml) or larger scale (30 ml).

Expression in CHO Cells

We utilised the Lonza GS Xceed™ Gene Expression System which uses a single selectable marker—glutamine synthetase (GS), encoded in the vector. CHO-K1 GS-knockout cells were used for transfection. Surviving cells will have integrated the vector in a transcriptionally active locus of the CHO genome—transcribing GS, to synthesise glutamine (essential for survival). The media used for selection is deficient in glutamine but supplemented by methionine sulfoximine (MSX) for stringent selection. MSX potently and irreversibly inhibits the GS enzyme.

Vectors encoding the heavy chains and 0325L common light chain of IXAX antibodies were linearised before transfection into CHO cells and subsequently purified using Phase Lock Gel tubes (Quantabio). The CHOK1SV GS-KO host cells were cultivated in CD-CHO media (Gibco), supplemented with 200 mM L-glutamine (Gibco)—to give a final concentration of 6 mM glutamine. The cells were incubated at 36.5° C., 140 rpm, 7% $CO_2$, 70% humidity. Cell density and viability were measured using the Vi-CELL XR cell viability analyser (Beckman Coulter). Five days before transfection, the cells were sub-cultured at 0.2×106 cells/mL in 200 mL TV CD-CHO 6 mM L-glutamine (Gin). Two days before the transfection, the cells were split into two 400 mL TV at 0.3×106 cells/mL in CD-CHO 6 mM Gln. The day of the transfection, the flasks were measured at 2.5/2.8×106 cells/mL. CHOK1SV GS-KO host cells were transfected with the linearised DNA using Amaxa 4D Nucleofector (Lonza) electroporation following the manufacturers protocol.

Once transfected, cells were incubated at for 24 hours at 36.5° C., 140 rpm, 7% CO2, 70% humidity. On day one post-transfection the pools were centrifuged at 200×g for 5 minutes. The supernatant was removed. The pellet was re-suspended in 30 mL of CD-CHO/SP4/MSX and transferred to new flasks. MSX at a concentration of 75 μM was used for positive selection of CHO cells containing the vectors, thus theoretically expressing the bispecific antibody. The cells were under selection for a total of 29 days. The minipools were incubated in a static incubator (36.5° C., 7% CO2, 70% humidity) for a total of 19 days before the first passage. All pools were kept under selection until the fed-batch overgrow was set-up to promote expression of the bispecific antibody.

For fed batch overgrow (FOG), cells were seeded at 0.2×106 viable cells/mL in 30 mL of pre-warmed CM79 medium in a new culture vessel (manufacturers protocol was followed). The flasks were placed in an incubator (36.5° C., 140 rpm, 7% CO2, 70% humidity). MSX selection at this stage was not included. From day three onwards, the glucose concentration and viable cell concentration were measured daily. Upon reaching >1.5×106 cells/mL, SP76 was added to the cells daily—the volume of SP76 added was determined by the viable cell concentration. 400 g/L D-glucose feed was added daily from day three onwards to prevent glucose depletion. The volume of 400 g/L D-glucose feed added was dependent on the measured glucose concentration. SF54, SF71 and SF77 were added at fixed volumes at regular intervals following the manufacturers recommendation. After 12 days, the 30 mL cultures were harvested. Following expression and harvest, bispecific antibodies were purified from CHO media using Protein A chromatography, protein quantified by OD280 and samples normalised for protein concentration.

Example 6 Confirmation of Expressed 0325L VL Domain Sequence by Mass Spectrometry Anti-FIX/anti-FX heterodimeric bispecific antibody generated from CHO cells (see Example 5) was analysed by MS.

When the mouse kappa light chain leader was used to express the 0325L common light chain, MW of the anti-FIX/anti-FX heterodimer determined by MS matched the theoretical MW predicted by amino acid sequences of the anti-FIX/anti-FX heterodimer.

Example 7 Comparison of Yield for λ Antibodies with and without N-Terminal VL Residue As detailed in Example 5, vectors comprising DNA encoding bispecific antibody IXAX-1172.0201.0128 were transfected into CHO cells. Two different leader sequences for the 0128L VL domain were used—either a codon-optimised native λ leader or a codon-optimised mouse kappa leader. Cells were selected for stable transfection using 75 μM MSX (methionine sulphoximine) which inhibits the GS protein.

Following stable expression of the bispecific antibodies, minipools were cultured by fed-batch overgrowth to allow bispecific antibody expression at 35 ml scale in shake flask. Following expression and harvest, bispecific antibody was purified from CHO supernatant using Protein A affinity chromatography (Mab Select Sure resin—General Electric). The expression yield was compared between the same bispecific antibody in the presence of the two different leader sequences—native leader and the mouse kappa leader. Similar expression yields (mg/L) were observed when expressing the same bispecific antibody with the different leaders. FIG. 5.

The functional impact of the N-terminal deletion may be due to steric hindrance from the side chain of the terminal serine residue, which could destabilise the disulphide bond between the light chain and heavy chain. It has been reported previously that deletion of an additional serine residue following the penultimate cysteine at the C-terminus of the λ Lc improved the thermal stability, stability to high pH, transient expression, purification yield, and ADCC function of IgG1λ antibody (Shen et al., mAbs 5(3):418-431 2013). Similarly, a change in stability may underlie the effect on antibody function in the present case, although other explanations cannot be ruled out. In view of the impact observed in the FXase assay, which relies on antigen binding by both arms of the IgG, we could also attribute the change in activity to an effect on antigen binding by the binding site which is formed by the antibody Fv (paired VH and VL domains) of the antibody. There is possibly an effect on binding kinetics, e.g., off-rate and/or on-rate, potentially affecting the overall affinity ($K_D$) of the antibody-antigen interaction. Since this is a bispecific antibody, another possibility is that the presence vs absence of the N-terminal residue at IMGT position 1 of the VL domain changes the % heterodimer expressed by the cells. The heterodimer is the active bispecific molecule, while homodimers formed by pairing of identical heavy chains, represent a contaminant species. Inclusion of the N-terminal Ser might reduce % heterodimer, lowering the effective yield of bispecific antibody and thus reducing the activity observed from the antibody composition.

In the case of the anti-FIXxFX bispecific antibodies including the λ common light chain, the unexpected absence of the N-terminal Ser is an advantage, and we have demonstrated herein how this advantage may be secured with a variety of different expression systems, overcoming the inclusion of the N-terminal Ser when the λ light chain is expressed with alternative leader sequences, while maintaining antibody yield.

Tables

TABLE L

| Gene segment | Example allele | Accession number | Status | IMGT amino acid sequence | SEQ ID NO: |
|---|---|---|---|---|---|
| IGLV1-36 | IGLV1-36*01 | Z73653 | F | QSVLTQPPS.VSEAP RQRVTISCSGS SSNI....GNNA VNWYQQLP GKAPKLLIY YD.......D LLPSGVS.D RFSGSK..SG TSASLAISGLQS EDEADYYC AAWDDSLNG | 1 |
| IGLV1-40 | IGLV1-40*01 | M94116 | F | QSVLTQPPS.VSGAP GQRVTISCTGS SSNIG...AGYD VHWYQQLP GTAPKLLIY GN.......S NRPSGVP.D RFSGSK..SG TSASLAITGLQA EDEADYYC QSYDSSLSG | 2 |
| IGLV1-41 | IGLV1-41*01 | M94118 | ORF | QSVLTQPPS.VSAAP GQKVTISCSGS SSDM....GNYA VSWYQQLP GTAPKLLIY EN.......N KRPSGIP.D RFSGSK..SG TSATLGITGLWP EDEADYYC LAWDTSPRA | 3 |
| IGLV1-44 | IGLV1-44*01 | Z73654 | F | QSVLTQPPS.ASGTP GQRVTISCSGS SSNI....GSNT VNWYQQLP GTAPKLLIY SN.......N QRPSGVP.D RFSGSK..SG TSASLAISGLQS EDEADYYC AAWDDSLNG | 4 |
| IGLV1-47 | IGLV1-47*01 | Z73663 | F | QSVLTQPPS.ASGTP GQRVTISCSGS SSNI....GSNY VYWYQQLP GTAPKLLIY RN.......N QRPSGVP.D RFSGSK..SG TSASLAISGLRS EDEADYYC AAWDDSLSG | 5 |
| IGLV1-50 | IGLV1-50*01 | M94112 | ORF | QSVLTQPPS.VSGAP GQRVTISCTGS SSNIG...AGYV VHWYQQLP GTAPKLLIY GN.......S NRPSGVP.D QFSGSK..SG TSASLAITGLQS EDEADYYC KAWDNSLNA | 6 |
| IGLV1-51 | IGLV1-51*01 | Z73661 | F | QSVLTQPPS.VSAAP GQKVTISCSGS SSNI....GNNY VSWYQQLP GTAPKLLIY DN.......N KRPSGIP.D RFSGSK..SG TSATLGITGLQT GDEADYYC GTWDSSLSA | 7 |

TABLE L-continued

| Gene segment | Example allele | Accession number | Status | IMGT amino acid sequence | SEQ ID NO: |
|---|---|---|---|---|---|
| IGLV1-62 | IGLV1-62*01 | D87022 | P | QSVLTQPPS.VSWAT RQRLTVSCTGS SSNTG...TGYN VNCWQ*LP RTDPKLLRH GD.......K NWASWVS.D QFSGSK..SG SLASLGTTGLWA EDKTDYHC QSRDIC*VL | 8 |
| IGLV2-5 | IGLV2-5*01 | Z73641 | | QSALIQPPS.VSGSP GQSVTISCTGT SSDVG...SYDY VSWYQQHP GTVPKPMIY NV.......N TQPSGVP.D RFSGSK..SG NTASMTISGLQA EDEADY*C CSYTSSAT* | 9 |
| IGLV2-8 | IGLV2-8*01 | X97462 | F | QSALTQPPS.ASGSP GQSVTISCTGT SSDVG...GYNY VSWYQQHP GKAPKLMIY EV.......S KRPSGVP.D RFSGSK..SG NTASLTVSGLQA EDEADYYC SSYAGSNNF | 10 |
| IGLV2-11 | IGLV2-11*01 | Z73657 | F | QSALTQPRS.VSGSP GQSVTISCTGT SSDVG...GYNY VSWYQQHP GKAPKLMIY DV.......S KRPSGVP.D RFSGSK..SG NTASLTISGLQA EDEADYYC CSYAGSYTF | 11 |
| IGLV2-14 | IGLV2-14*01 | Z73664 | F | QSALTQPAS.VSGSP GQSITISCTGT SSDVG...GYNY VSWYQQHP GKAPKLMIY EV.......S NRPSGVS.N RFSGSK..SG NTASLTISGLQA EDEADYYC SSYTSSSTL | 12 |
| IGLV2-18 | IGLV2-18*01 | Z73642 | F | QSALTQPPS.VSGSP GQSVTISCTGT SSDVG...SYNR VSWYQQPP GTAPKLMIY EV.......S NRPSGVP.D RFSGSK..SG NTASLTISGLçA EDEADYYC SLYTSSSTF | 13 |
| IGLV2-23 | IGLV2-23*01 | X14616 | F | QSALTQPAS.VSGSP GQSITISCTGT SSDVG...SYNL VSWYQQHP GKAPKLMIY EG.......S KRPSGVS.N RFSGSK..SG NTASLTISGLQA EDEADYYC CSYAGSSTL | 14 |
| IGLV2-33 | IGLV2-33*01 | Z73643 | ORF | QSALTQPPF.VSGAP GQSVTISCTGT SSDVG...DYDH VFWYQKRL STTSRLLIY NV.......N TRPSGIS.D LFSGSK..SG NMASLTISGLKS EVEANYHC SLYSSSYTF | 15 |
| IGLV2-34 | IGLV2-34*01 | D87013 | P | QSVLTQPRS. VSRSP GQ*VTIFCTGT SSDIG...GYDL VSWCQ*HP GKAPKLMIY DV.......A NWPSGAP.G CFSGSK..SG NTASLTISGLQA EDEADYYC SSYAGSYNF | 16 |
| IGLV2-NL1 | IGLV2-NL1*01 | Z22209 | P | QSVLTQPRS.VSRSP GQ*VTIFCTGT SSDIG...GYDL VSWCQ*HP GKAPKLMIY DV.......G NWPSGAP.G CFSGSK..SG NTASLTISGLQA EDEADYYC SSYAGSYNF | 17 |
| IGLV3-1 | IGLV3-1*01 | X57826 | F | SYELTOPPS.VSVSP GQTASITCSGD KLG......DKY ACWYQQKP GQSPVLVIY QD.......S KRPSGIP.E RFSGSN..SG NTATLTISGTQA MDEADYYC QAWDSSTA | 18 |
| IGLV3-9 | IGLV3-9*01 | X97473 | F | SYELTQPLS. VSVAL GQTARITCGGN NIG......SKN VHWYQQKP GOAPVLVIY RD.......S NRPSGIP.E RFSGSN..SG NTATLTISRAçA GDEADYYC QVWDSSTA | 19 |

TABLE L-continued

| Gene segment | Example allele | Accession number | Status | IMGT amino acid sequence | SEQ ID NO: |
|---|---|---|---|---|---|
| IGLV3-10 | IGLV3-10*01 | X97464 | F | SYELTOPPS.VSVSP GQTARITCSGD ALP......KKY AYWYQQKS GOAPVLVIY ED.......S KRPSGIP.E RFSGSS..SG TMATLTISGAQV EDEADYYC YSTDSSGNH | 20 |
| IGLV3-12 | IGLV3-12*01 | Z73658 | F | SYELTQPHS. VSVAT AQMARITCGGN NIG......SKA VHWYQQKP GQDPVLVIY SD.......S NRPSGIP.E RFSGSN..PG NTTTLTISRIEA GDEADYYC QVWDSSSDH | 21 |
| IGLV3-13 | IGLV3-13*01 | X97463 | P | SYELTOPPA.VSVSP GQTARISCSGD VLR......DNY ADWYPQKP GOAPVLVIY KD.......G ERPSGIP.E RFSGST..SG NTTALTISRVLT KGGADYYC FSGD*NN | 22 |
| IGLV3-16 | IGLV3-16*01 | X97471 | F | SYELTOPPS.VSVSL GQMARITCSGE ALP......KKY AYWYQQKP GQFPVLVIY KD.......S ERPSGIP.E RFSGSS..SG TIVTLTISGVQA EDEADYYC LSADSSGTY | 23 |
| IGLV3-19 | IGLV3-19*01 | X56178 | F | SSELTQDPA.VSVAL GOTVRITCQGD SLR......SYY ASWYQQKP GOAPVLVIY GK.......N NRPSGIP.D RFSGSS..SG NTASLTITGAQA EDEADYYC NSRDSSGNH | 24 |
| IGLV3-21 | IGLV3-21*01 | X71966 | F | SYVLTQPPS.VSVAP GKTARITCGGN NIG......SKS VHWYQQKP GOAPVLVIY YD.......S DRPSGIP.E RFSGSN..SG NTATLTISRVEA GDEADYYC QVWDSSSDH | 25 |
| IGLV3-22 | IGLV3-22*01 | Z73666 | F | SYELTQLPS.VSVSP GQTARITCSGD VLG......ENY ADWYQQKP GQAPELVIY ED.......S ERYPGIP.E RFSGST..SG NTTTLTISRVLT EDEADYYC LSGDEDN | 26 |
| IGLV3-25 | IGLV3-25*01 | X97474 | F | SYELMQPPS.VSVSP GQTARITCSGD ALP......KQY AYWYQQKP GQAPVLVIY KD.......S ERPSGIP.E RFSGSS..SG TTVTLTISGVQA EDEADYYC QSADSSGTY | 27 |
| IGLV3-27 | IGLV3-27*01 | D86994 | F | SYELTQPSS.VSVSP GQTARITCSGD VLA......KKY ARWFQQKP GQAPVLVIY KD.......S ERPSGIP.E RFSGSS..SG TTVTLTISGAQV EDEADYYC YSAADNN | 28 |
| IGLV3-31 | IGLV3-31*01 | X97469 | P | SSELSQEPA.VSVAL G*TARITCQGD SIE......DSV VNWYKQKP SOAPGLVI* LN.......S VQSSGIP.K KFSGSS..SG NMATLTITGIQV EDKADYYC QSWDSSRTH | 29 |
| IGLV3-32 | IGLV3-32*01 | Z73645 | ORF | SSGPTQVPA.VSVAL GOMARITCQGD SME......GSY EHWYQQKP GOAPVLVIY DS.......S DRPSRIP.E RFSGSK..SG NTTTLTITGAQA EDEADYYY QLIDNHA | 30 |
| IGLV4-3 | IGLV4-3*01 | X57828 | F | LPVLTQPPS.ASALL GASIKLTCTLS SEHS.....TYT IEWYQQRP GRSPQYIMK VKSD...GSH SKGDGIP.D RFMGSS..SG ADRYLTFSNLQS DDEAEYHC GESHTIDGQVG* | 31 |
| IGLV4-60 | IGLV4-60*01 | Z73667 | F | QPVLTQSSS.ASASL GSSVKLTCTLS SGHS.....SYI IAWHQQQP GKAPRYLMK LEGS...GSY NKGSGVP.D RFSGSS..SG ADRYLTISNLQL EDEADYYC ETWDSNT | 32 |

TABLE L-continued

| Gene segment | Example allele | Accession number | Status | IMGT amino acid sequence | SEQ ID NO: |
|---|---|---|---|---|---|
| IGLV4-69 | IGLV4-69*01 | Z73648 | F | QLVLTQSPS.ASASL GASVKLTCTLS SGHS.....SYA IAWHQQQP EKGPRYLMK LNSD...GSH SKGDGIP.D RFSGSS..SG AERYLTISSLQS EDEADYYC QTWGTGI | 33 |
| IGLV5-37 | IGLV5-37*01 | Z73672 | F | QPVLTQPPS. SSASP GESARLTCTLP SDINV...GSYN IYWYQQKP GSPPRYLLY YYSD...SDK GQGSGVP.S RFSGSKDASA NTGILLISGLQS EDEADYYC MIWPSNAS | 34 |
| IGLV5-39 | IGLV5-39*01 | Z73668 | F | QPVLTQPTS. LSASP GASARFTCTLR SGINV...GTYR IYWYQQKP GSLPRYLLR YKSD...SDK QQGSGVP.S RFSGSKDAST NAGLLLISGLQS EDEADYYC AIWYSSTS | 35 |
| IGLV5-45 | IGLV5-45*01 | Z73670 | F | QAVLTQPAS.LSASP GASASLTCTLR SGINV...GTYR IYWYQQKP GSPPQYLLR YKSD...SDK QQGSGVP.S RFSGSKDASA NAGILLISGLQS EDEADYYC MIWHSSAS | 36 |
| IGLV5-48 | IGLV5-48*01 | Z73649 | ORF | QPVLTQPTS. LSASP GASARLTCTLR SGINL...GSYR IFWYQQKP ESPPRYLLS YYSD...SSK HQGSGVP.S RFSGSKDASS NAGILVISGLQS EDEADYYC MIWHSSAS | 37 |
| IGLV5-52 | IGLV5-52*01 | Z73669 | F | QPVLTQPSS.HSASS GASVRLTCMLS SGFSV...GDFW IRWYQQKP GNPPRYLLY YHSD...SNK GQGSGVP.S RFSGSNDASA NAGILRISGLQP EDEADYYC GTWHSNSKT | 38 |
| IGLV6-57 | IGLV6-57*01 | Z73673 | F | NFMLTQPHS.VSESP GKTVTISCTRS SGSI....ASNY VQWYQQRP GSSPTTVIY ED.......N QRPSGVP.D RFSGSIDSSS NSASLTISGLKT EDEADYYC QSYDSSN | 39 |
| IGLV7-43 | IGLV7-43*01 | X14614 | F | QTVVTQEPS.LTVSP GGTVTLTCASS TGAVT...SGYY PNWFQQKP GOAPRALIY ST.......S NKHSWTP.A RFSGSL..LG GKAALTLSGVQP EDEAEYYC LLYYGGAQ | 40 |
| IGLV7-46 | IGLV7-46*01 | Z73674 | F | QAVVTQEPS.LTVSP GGTVTLTCGSS TGAVT...SGHY PYWFQQKP GQAPRTLIY DT.......S NKHSWTP.A RFSGSL..LG GKAALTLSGAQP EDEAEYYC LLSYSGAR | 41 |
| IGLV8-61 | IGLV8-61*01 | Z73650 | F | QTVVTQEPS.FSVSP GGTVTLTCGLS SGSVS...TSYY PSWYQQTP GOAPRTLIY ST.......N TRSSGVP.D RFSGSI..LG NKAALTITGAçA DDESDYYC VLYMGSGI | 42 |
| IGLV9-49 | IGLV9-49*01 | Z73675 | F | QPVLTQPPS.ASASL GASVTLTCTLS SGYS.....NYK VDWYQQRP GKGPRFVMR VGTG..GIVG SKGDGIP.D RFSVLG..SG LNRYLTIKNIQE EDESDYHC GADHGSGSNFV* | 43 |
| IGLV10-54 | IGLV10-54*01 | Z73676 | F | QAGLTOPPS.VSKGL ROTATLTCTGN SNNV....GNQG AAWLQQHQ GHPPKLLSY RN.......N NRPSGIS.E RLSASR.. SG NTASLTITGLQP EDEADYYC SAWDSSLSA | 44 |

TABLE L-continued

| Gene segment | Example allele | Accession number | Status | IMGT amino acid sequence | SEQ ID NO: |
|---|---|---|---|---|---|
| IGLV11-55 | IGLV11-55*01 | D86996 | ORF | RPVLTQPPS.LSASP GATARLPCTLS SDLSV...GGKN MFWYQQKP GSSPRLFLY HYSD...SDK QLGPGVP.S RVSGSKETSS NTAFLLISGLQP EDEADYYC QVYESSAN | 45 |

Human v lambda alleles and sequences from IMGT database. Only the *01 allele of each segment is shown. Dots (.) indicate gaps according to the IMGT unique numbering as defined by Lefranc, M.-P. et al., Dev. Comp. Immunol., 27, 55-77 (2003). Asterisk (*) in the sequence indicate a stop codon. F: Functional; P: Pseudogene; ORF: Open Reading Frame as defined by IMGT. Translation of each germline v gene segment is grouped into 11 amino acid sequence blocks, which correspond to the following components of the VL domain, respectively (shown for IGLV1-36*01 sequence example):

| | | | |
|---|---|---|---|
| QSVLTQPPS.VSEAP | FR1 | A | IMGT 1-15 |
| RQRVTISCSGS | FR1 | B | IMGT 16-26 |
| SSNI....GNNA | CDR1 | B-C loop | IMGT 27-38 |
| VNWYQQLP | FR2 | C | IMGT 39-46 |
| GKAPKLLIY | FR2 | C′ | IMGT 47-55 |
| YD......D | CDR2 | C′-C" loop | IMGT 56-65 |
| LLPSGVS.D | FR3 | C" | IMGT 66-74 |
| RFSGSK..SG | FR3 | D | IMGT 75-85 |
| TSASLAISGLQS | FR3 | E | IMGT 85-96 |
| EDEADYYC | FR3 | F | IMGT 97-104 |
| AAWDDSLNG | CDR3 | F-G loop | IMGT 105-117 |

On recombination to generate the VL domain, the v segment combines with the downstream j segment and the LCDR3 comprises the v-j junction.

TABLE N

Nucleotide sequences of known human vλ3-21 alleles.

| IGLV3-21 allele | Nucleotide sequence |
|---|---|
| vλ3-21*d01 SEQ ID NO: 56 | TCCTATGTGCTGACTCAGCCACCCTCAGTGTCAGTGGCCCCAGGAAAGACGGCCAGGATTACCTGTGGGGG AAACAACATTGGAAGTAAAAGTGTGCACTGGTACCAGCAGAAGCCAGGCCAGGCCCCTGTGCTGGTCATCT ATTATGATAGCGACCGGCCCTCAGGGATCCCTGAGCGATTCTCTGGCTCCAACTCTGGGAACACGGCCACC CTGACCATCAGCAGGGTCGAAGCCGGGGATGAGGCCGACTATTACTGTCAGGTGTGGGATAGTAGTAGTGA TCATCC |
| vλ3-21*01 X71966 SEQ ID NO: 57 | TCCTATGTGCTGACTCAGCCACCCTCAGTGTCAGTGGCCCCAGGAAAGACGGCCAGGATTACCTGTGGGGG AAACAACATTGGAAGTAAAAGTGTGCACTGGTACCAGCAGAAGCCAGGCCAGGCCCCTGTGCTGGTCATCT ATTATGATAGCGACCGGCCCTCAGGGATCCCTGAGCGATTCTCTGGCTCCAACTCTGGGAACACGGCCACC CTGACCATCAGCAGGGTCGAAGCCGGGGATGAGGCCGACTATTACTGTCAGGTGTGGGACAGTAGTAGTGA TCATCC |
| vλ3-21*02 D87007 SEQ ID NO: 58 | TCCTATGTGCTGACTCAGCCACCCTCGGTGTCAGTGGCCCCAGGACAGACGGCCAGGATTACCTGTGGGGG AAACAACATTGGAAGTAAAAGTGTGCACTGGTACCAGCAGAAGCCAGGCCAGGCCCCTGTGCTGGTCGTCT ATGATGATAGCGACCGGCCCTCAGGGATCCCTGAGCGATTCTCTGGCTCCAACTCTGGGAACACGGCCACC CTGACCATCAGCAGGGTCGAAGCCGGGGATGAGGCCGACTATTACTGTCAGGTGTGGGATAGTAGTAGTGA TCATCC |
| vλ3-21*03 M94115 SEQ ID NO: 59 | TCCTATGTGCTGACTCAGCCACCCTCGGTGTCAGTGGCCCCAGGAAAGACGGCCAGGATTACCTGTGGGGG AAACAACATTGGAAGTAAAAGTGTGCACTGGTACCAGCAGAAGCCAGGCCAGGCCCCTGTGCTGGTCGTCT ATGATGATAGCGACCGGCCCTCAGGGATCCCTGAGCGATTCTCTGGCTCCAACTCTGGGAACACGGCCACC CTGACCATCAGCAGGGTCGAAGCCGGGGATGAGGCCGACTATTACTGTCAGGTGTGGGATAGTAGTAGTGA TCATCC |

TABLE P

| Examples of signal peptides | | | |
|---|---|---|---|
| SEQ ID | Name | Sequence | Reference |
| 60 | human signal peptide IGLV3-21, native for 0128L and 0325L VL domains | MAWTALLLGLLSHCTGSVT | |
| 61 | germline nucleotide sequence encoding human signal peptide IGLV3-21 | ATGGCCTGGACCGCTCTCCTCCTCGGCCTCCTCTCTCA CTGCACAGGCTCTGTGACC | |
| 62 | mouse kappa light chain signal peptide | MSVPTQVLGLLLLWLTDARC | Whittle et al., Protein Engineering 1 (6): 499-505 1987 |
| 63 | germline nucleotide sequence encoding mouse kappa light chain signal peptide | ATGAGTGTGCCCACTCAGGTCCTGGGGTTGCTGCTGCT GTGGCTTACAGATGCCAGATGT | Whittle et al., Protein Engineering 1 (6): 499-505 1987 |
| 64 | nucleotide sequence encoding mouse kappa light chain signal peptide, codon-optimised for CHO | ATGTCTGTGCCTACACAGGTTCTGGGACTGCTGCTGCT GTGGCTGACCGACGCCAGATGT | |
| 65 | nucleic acid encoding 0325L VL domain with signal peptide | ATGTCTGTGCCTACACAGGTTCTGGGACTGCTGCTGCTGTGGCTGACCGACGCCAGATGTTACGTGCTGACCCAGCCTCCTTCCGT GTCTGTTGCTCCTGGCGAGACAGCCAGAATCACCTGTGGCGGCGATAACATCGGCCGGAAGTCCGTGTACTGGTATCAGCAGAAGT CCGGCCAGGCTCCTGTGCTGGTCATCTACTACGACTCCGACCGGCCTTCTGGCATCCCTGAGAGATTCTCCGGCTCCAACTCCGGC AATACCGCCACACTGACCATCTCCAGAGTGGAAGCTGGCGACGAGGCCGACTACTACTGCCAAGTGTGGGACGGCTCCTCTGACCA CTGGGTTTTCGGCGGAGGCACCAAGCTGACAGTGCTG | |
| 66 | 0325L with mouse kappa signal peptide | MSVPTQVLGLLLLWLTDARCYVLTQPPSVSVAPGETARITCGGDNIGRKSVYWYQQKSGQAPVLVIYYDSDRPSGIPERFSGSNSG NTATLTISRVEAGDEADYYCQVWDGSSDHWVFGGGTKLTVL | |
| 67 | A light chain comprising 0325L VL domain with mouse kappa signal peptide | MSVPTQVLGLLLLWLTDARCYVLTOPPSVSVAPGETARITCGGDNIGRKSVYWYQQKSGQAPVLVIYYDSDRPSGIPERFSGSNSG NTATLTISRVEAGDEADYYCQVWDGSSDHWVFGGGTKLTVLGQPKAAPSVTLFPPSSEELQANKATLVCLISDFYPGAVTVAWKAD SSPVKAGVETTTPSKQSNNKYAASSYLSLTPEQWKSHKSYSCQVTHEGSTVEKTVAPTECS | |
| 68 | 0128L VL domain with mouse kappa signal peptide | MSVPTQVLGLLLLWLTDARCSYVLTQPPSVSVAPGETARITCGGDNIGRKSVYWYQQKSGQAPVLVIYYDSDRPSGIPERFSGSNS GNTATLTISRVEAGDEADYYCQVWDGSSDHWVFGGGTKLTVL | |
| 69 | V12 signal peptide derived from Sandfly Yellow related protein | MRFFFVFLAIVLFQGIHG | WO2008/148519 |

TABLE P-continued

| Examples of signal peptides | | | |
|---|---|---|---|
| SEQ ID | Name | Sequence | Reference |
| 70 | V14 signal peptide derived from Silkworm Fibroin LC | MKPIFLVLLWTSAYA | WO2008/148519 |
| 71 | V16 signal peptide derived from Snake PLA2 | MRTLWIMAVLLLGVEG | WO2008/148519 |
| 72 | V17 signal peptide derived from Cypridina Noctiluca luciferase | MKTLILAVALVYCATVHC | WO2008/148519 |
| 73 | V19 signal peptide derived from Pinemoth Fibroin LC | MMRPIVLVLLFATSALA | WO2008/148519 |
| 4 | murine signal peptide | MGWSCIILFLVATATGVHS | Gibson et al 2017 |
| 75 | V lambda 3 family signal peptide | MAWTPLLLPLLTLCTSEA | Gibson et al 2017 |
| 76 | V lambda 1 family signal peptide | MAGFPLLLTLLTHCAGSWA | Gibson et al 2017 |
| 77 | V kappa 1 family signal peptide | MDMRVPAQLLGLLLLWLPGAKC | Gibson et al 2017 |

TABLE S

| | Sequences of antibody heavy and light chain domains, all of which represent embodiments of the present invention. | |
|---|---|---|
| 78 | N1280H VH domain coding nucleotide sequence | GAGGTGCAGCTGGTGGAGTCTGGGGGAGGCTTTGTCCAGCCTGGGGGGTCCCTGAGACTCTCCTGTGCAGTCTCTGGAT<br>TCAGATTTAATAGCTATTGGATGAGCTGGGTCCGCCAGGCTCCAGGGAAGGGGCTGGAGTGGGTGGCCAACATAAACCA<br>AGATGGAAGTAGAAAATTCTATGTGGCCTCTGTGAAGGGCCGATTCACCATGTCCAGAGACAACGCCAAGAAATCAGTG<br>TATGTACAAATGAACAGCCTGAGAGCCGAGGACACGGCTGTGTATTACTGTGCGAGAGAGGGGTATAGTAGTATCAAGT<br>ATTATGGTATGGACGTCTGGGGCCAAGGGACCACGGTCACCGTCTCCTCA |
| 79 | N1280H VH domain amino acid sequence | EVQLVESGGGFVQPGGSLRLSCAVSGFRFNSYWMNSWVRQAPGKGLEWVANINQDGSRKFYVASVKGRFTMSRDNAKKSV<br>YVQMNSLRAEDTAVYYCAREGYSSIKYYGMDVWGQGTTVTVSS |
| 80 | Nucleic acid encoding N1280H-IgG4-P K439E heavy chain;<br>N1280 coding sequence underlined. | GAAGTGCAGCTGGTTGAATCTGGCGGCGGATTTGTTCAGCCTGGCGGCTCTCTGAGACTGTCCTGTGCTGTGTCCGGCT<br>TCCGGTTCAACTCCTACTGGATGTCCTGGGTCCGACAGGCTCCTGGCAAAGGACTGGAATGGGTCGCCAACATCAACCA<br>GGACGGCTCCCGGAAGTTCTACGTGGCCTCTGTGAAGGGCAGATTCACCATGTCTCGGGACAACGCCAAGAAATCCGTG<br>TACGTGCAGATGAACTCCCTGAGAGCCGAGGACACCGCCGTGTACTACTGTGCTAGAGAGGGCTACTCCTCCATCAAGT<br>ACTACGGCATGGACGTGTGGGGCCAGGGCACAACCGTGACAGTCTCTTCCGCTTCCACCAAGGGACCCAGCGTTTTCCC<br>TCTGGCTCCTTGCTCCAGATCCACCTCCGAGTCTACAGCTGCTCTGGGCTGCCTGGTCAAGGACTACTTTCCTGAGCCT<br>GTGACCGTGTCCTGGAACTCTGGCGCTCTGACATCTGGCGTGCACACCTTTCCAGCTGTGCTGCAGTCCTCCGGCCTGT<br>ACTCTCTGTCCTCTGTCGTGACCGTGCCTTCCAGCTCTCTGGGAACCCAGACCTACACCTGTAATGTGGACCACAAGCC<br>TTCCAACACCAAGGTGGACAAGCGCGTGGAATCTAAGTACGGCCCTCCTTGTCCTCCATGTCCTGCTCCAGAGTTTCTC<br>GGCGGACCCTCCGTGTTTCTGTTCCCTCCAAAGCCTAAGGACACCCTGATGATCTCTCGGACCCCTGAAGTGACCTGCG<br>TGGTGGTGGATGTGTCCCAAGAGGATCCCGAGGTGCAGTTCAATTGGTACGTGGACGGCGTGGAAGTGCACAATGCCAA<br>GACCAAGCCTAGAGAGGAACAGTACAACTCCACCTACAGAGTGGTGTCCGTGCTGACCGTGCTGCACCAGGATTGGCTG<br>AACGGCAAAGAGTACAAGTGCAAGGTGTCCAACAAGGGCCTGCCTAGCTCCATCGAAAAGACCATCTCCAAGGCCAAGG<br>GCCAGCCTCGAGAACCCCAGGTTTACACCCTGCCTCCAAGCCAAGAGGAAATGACCAAGAACCAGGTGTCCCTGACCTG<br>TCTCGTGAAGGGCTTCTACCCCTCCGATATCGCCGTGGAATGGGAGTCTAATGGCCAGCCAGAGAACAACTACAAGACC<br>ACACCTCCAGTGCTGGACTCCGACGGCTCATTCTTTCTGTACTCCAAGCTGACAGTGGACAAGTCCCGGTGGCAAGAGG<br>GCAACGTGTTCTCCTGCTCTGTGATGCACGAGGCCCTGCACAACCACTACACCCAAGAGTCCCTGTCTCTGTCCCCT |
| 81 | N1280H-IgG4-P K439E amino acid sequence | EVQLVESGGGFVQPGGSLRLSCAVSGFRFNSYWMSWVRQAPGKGLEWVANINQDGSRKFYVASVKGRFTMSRDNAKKSV<br>YVQMNSLRAEDTAVYYCAREGYSSIKYYGMDVWGQGTTVTVSSASTKGPSVFPLAPCSRSTSESTAALGCLVKDYFPEP<br>VTVSWNSGALTSGVHTFPAVLQSSGLYSLSSVVTVPSSSLGTQTYTCNVDHKPSNTKVDKRVESKYGPPCPPCPAPEFL<br>GGPSVFLFPPKPKDTLMISRTPEVTCVVVDVSQEDPEVQFNWYVDGVEVHNAKTKPREEQYNSTYRVVSVLTVLHQDWL<br>NGKEYKCKVSNKGLPSSIEKTISKAKGQPREPQVYTLPPSQEEMTKNQVSLTCLVKGFYPSDIAVEWESNGQPENNYKT<br>TPPVLDSDGSFFLYSKLTVDKSRWQEGNVFSCSVMHEALHNHYTQESLSLSP |
| 82 | N1441H VH domain encoding nucleotide sequence | GAGGTGCAGCTGGTTGAATCTGGCGGCGGATTTGTTCAGCCTGGCGGCTCTCTGAGACTGAGCTGTGCCGTGTCCGGCT<br>TCCGGTTCAACAGCTACTGGATGTCCTGGGTCCGACAGGCCCCTGGCAAAGGACTTGAGTGGGTCGCCAACATCAACCA<br>GGACGGCAGCCGGAAGTTTTACGTGGCCTCTGTGAAGGGCAGATTCACCATGAGCCGGGACAACGCCGACAAAAGCGTG<br>TACGTGCAGATGAACAGCCTGAGAGCCGAGGACACCGCCGTGTACTATTGTGCCAGAGAGGGCTACAGCAGCATCAAGT<br>ACTACGGCATGGACGTGTGGGGCCAGGGCACAACAGTGACAGTCTCTTCT |
| 83 | N1441H VH domain amino acid sequence | EVQLVESGGGFVQPGGSLRLSCAVSGFRFNSYWMSWVRQAPGKGLEWVANINQDGSRKYFVASVKGRFTMSRDNADKSV<br>YVQMNSLRAEDTAVYYCAREGYSSIKYYGMDVWGQGTTVTVSS |

TABLE S-continued

| Sequences of antibody heavy and light chain domains, all of which represent embodiments of the present invention. | | |
|---|---|---|
| 84 | Nucleic acid encoding N1441H-IgG4-P K439E heavy chain | GAAGTGCAGCTGGTTGAATCTGGCGGCGGATTTGTTCAGCCTGGCGGCTCTCTGAGACTGTCCTGTGCTGTGTCCGGCT<br>TCCGGTTCAACTCCTACTGGATGTCCTGGGTCCGACAGGCTCCTGGCAAAGGACTGGAATGGGTCGCCAACATCAACCA<br>GGACGGCTCCCGGAAGTTCTACGTGGCCTCTGTGAAGGGCAGATTCACCATGTCTCGGGACAACGCCGACAAGTCCGTG<br>TACGTGCAGATGAACTCCCTGAGAGCCGAGGACACCGCCGTGTACTACTGTGCTAGAGAGGGCTACTCCTCCATCAAGT<br>ACTACGGCATGGACGTGTGGGGCCAGGGCACAACCGTGACAGTCTCTTCCGCTTCCACCAAGGGACCCAGCGTTTTCCC<br>TCTGGCTCCTTGCTCCAGATCCACCTCCGAGTCTACAGCTGCTCTGGGCTGCCTGGTCAAGGACTACTTTCCTGAGCCT<br>GTGACCGTGTCCTGGAACTCTGGCGCTCTGACATCTGGCGTGCACACCTTTCCAGCTGTGCTGCAGTCCTCCGGCCTGT<br>ACTCTCTGTCCTCTGTCGTGACCGTGCCTTCCAGCTCTCTGGGAACCCAGACCTACACCTGTAATGTGGACCACAAGCC<br>TTCCAACACCAAGGTGGACAAGCGCGTGGAATCTAAGTACGGCCCTCCTTGTCCTCCATGTCCTGCTCCAGAGTTTCTC<br>GGCGGACCCTCCGTGTTTCTGTTCCCTCCAAAGCCTAAGGACACCCTGATGATCTCTCGGACCCCTGAAGTGACCTGCG<br>TGGTGGTGGATGTGTCCCAAGAGGATCCCGAGGTGCAGTTCAATTGGTACGTGGACGGCGTGGAAGTGCACAACGCCAA<br>GACCAAGCCTAGAGAGGAACAGTACAACTCCACCTACAGAGTGGTGTCCGTGCTGACCGTGCTGCACCAGGATTGGCTG<br>AACGGCAAAGAGTACAAGTGCAAGGTGTCCAACAAGGGCCTGCCTAGCTCCATCGAAAAGACCATCTCCAAGGCCAAGG<br>GCCAGCCTCGAGAACCCCAGGTTTACACCCTGCCTCCAAGCCAAGAGGAAATGACCAAGAACCAGGTGTCCCTGACCTG<br>TCTCGTGAAGGGCTTCTACCCCTCCGATATCGCCGTGGAATGGGAGTCTAATGGCCAGCCAGAGAACAACTACAAGACC<br>ACACCTCCAGTGCTGGACTCCGACGGCTCATTCTTTCTGTACTCCAAGCTGACAGTGGACAAGTCCCGGTGGCAAGAGG<br>GCAACGTGTTCTCCTGCTCTGTGATGCACGAGGCCCTGCACAACCACTACACCCAAGAGTCCCTGTCTCTGTCCCCT |
| 85 | N1441H-IgG4-P K439E amino acid sequence | EVQLVESGGGFVQPGGSLRLSCAVSGFRFNSYWMSWVRQAPGKGLEWVANINQDGSRKFYVASVKGRFTMSRDNADKSV<br>YVQMNSLRAEDTAVYYCAREGYSSIKYYGMDVWGQGTTVTVSSASTKGPSVFPLAPCSRSTSESTAALGCLVKDYFPEP<br>VTVSWNSGALTSGVHTFPAVLQSSGLYSLSSVVTVPSSSLGTQTYTCNVDHKPSNTKVDKRVESKYGPPCPPCPAPEFL<br>GGPSVFLFPPKPKDTLMISRTPEVTCVVVDVSQEDPEVQFNWYVDGVEVHNAKTKPREEQYNSTYRVVSVLTVLHQDWL<br>NGKEYKCKVSNKGLPSSIEKTISKAKGQPREPQVYTLPPSQEEMTKNQVSLTCLVKGFYPSDIAVEWESNGQPENNYKT<br>TPPVLDSDGSFFLYSKLTVDKSRWQEGNVFSCSVMHEALHNHYTQESLSLSP |
| 86 | T0999H VH domain coding nucleotide sequence | CAGGTTCAGCTGATTCAGTCCGGCGCCAAAGTGAAGAAACCTGGCGCCTCTGTGAAGGTGTCCTGCAAGGCCTCTCGGT<br>ACAAGTTCACCTCCTACTACATGCACTGGGTCCGACAGGCCCCTGGACAAGGATTGGAGTGGATGGGCATCATCAACCC<br>CAAGTCCGGCTCCACCTCTTACGCCCAGAAATTCCAGGGCAGAGTGACCATGACCAGAGACACCTCTACCTCCACCGTG<br>TACATGGAACTGTCCAGCCTGAGATCCGAGGACACCGCCGTGTACTACTGTGCCAGAGATGGCTACGGCAGCTTCTCCA<br>GACTGATCCAGTTGTGGGGCCAGGGCACACTGGTCACAGTGTCCTCT |
| 87 | T0999H VH domain amino acid sequence | QVQLIQSGAKVKKPGASVKVSCKASRYKFTSYYMHWVRQAPGQGLEWMGIINPKSGSTSYAQKFQGRVTMTRDTSTSTV<br>YMELSSLRSEDTAVYYCARDGYGSFSRLIQLWGQGTLVTVSS |
| 88 | Nucleic acid encoding T0999H-IgG4-P E356K heavy chain;<br>T0999H coding sequence underlined | CAGGTTCAGCTGATTCAGTCCGGCGCCAAAGTGAAGAAACCTGGCGCCTCTGTGAAGGTGTCCTGCAAGGCCTCTCGGT<br>ACAAGTTCACCTCCTACTACATGCACTGGGTCCGACAGGCCCCTGGACAAGGATTGGAGTGGATGGGCATCATCAACCC<br>CAAGTCCGGCTCCACCTCTTACGCCCAGAAATTCCAGGGCAGAGTGACCATGACCAGAGACACCTCTACCTCCACCGTG<br>TACATGGAACTGTCCAGCCTGAGATCCGAGGACACCGCCGTGTACTACTGTGCCAGAGATGGCTACGGCAGCTTCTCCA<br>GACTGATCCAGTTGTGGGGCCAGGGCACACTGGTCACAGTGTCCTCTGCTTCCACCAAGGGACCCAGCGTGTTCCCTCT<br>GGCTCCTTGCTCCAGATCCACCTCCGAGTCTACAGCTGCTCTGGGCTGCCTGGTCAAGGACTACTTTCCTGAGCCTGTG<br>ACCGTGTCTTGGAACTCTGGCGCTCTGACATCTGGCGTGCACACCTTTCCAGCTGTGCTGCAGTCCTCCGGCCTGTACT<br>CTCTGTCCTCTGTCGTGACCGTGCCTTCCAGCTCTCTGGGAACCCAGACCTACACCTGTAATGTGGACCACAAGCCTTC<br>CAACACCAAGGTGGACAAGCGCGTGGAATCTAAGTACGGCCCTCCTTGTCCTCCATGTCCTGCTCCAGAGTTTCTCGGC |

TABLE S-continued

| Sequences of antibody heavy and light chain domains, all of which represent embodiments of the present invention. | | |
|---|---|---|
| | | GGACCCTCCGTGTTTCTGTTCCCTCCAAAGCCTAAGGACACCCTGATGATCTCTCGGACCCCTGAAGTGACCTGCGTGG<br>TGGTGGATGTGTCCCAAGAGGATCCCGAGGTGCAGTTCAATTGGTACGTGGACGGCGTGGAAGTGCACAACGCCAAGAC<br>CAAGCCTAGAGAGGAACAGTACAACTCCACCTACAGAGTGGTGTCCGTGCTGACCGTGCTGCACCAGGATTGGCTGAAC<br>GGCAAAGAGTACAAGTGCAAGGTGTCCAACAAGGGCCTGCCTAGCTCCATCGAAAAGACCATCTCCAAGGCCAAGGGCC<br>AGCCTCGAGAACCCCAGGTTTACACCCTGCCTCCAAGCCAGAAAGAGATGACCAAGAACCAGGTGTCCCTGACCTGCCT<br>CGTGAAGGGCTTCTACCCTTCCGATATCGCCGTGGAATGGGAGAGCAATGGCCAGCCAGAGAACAACTACAAGACCACA<br>CCTCCTGTGCTGGACTCCGATGGCTCATTCTTTCTGTACTCCAAGCTGACAGTGGACAAGTCCCGGTGGCAAGAGGGCA<br>ACGTGTTCTCCTGCTCTGTGATGCACGAGGCCCTGCACAACCACTACACCCAGAAGTCCCTGTCTCTGTCCCCT |
| 89 | T0999H-IgG4-P E356K amino acid sequence | QVQLIQSGAKVKKPGASVKVSCKASRYKFTSYYMHWVRQAPGQGLEWMGIINPKSGSTSYAQKFQGRVTMTRDTSTSTV<br>YMELSSLRSEDTAVYYCARDGYGSFSRLIQLWGQGTLVTVSSASTKGPSVFPLAPCSRSTSESTAALGCLVKDYFPEPV<br>TVSWNSGALTSGVHTFPAVLQSSGLYSLSSVVTVPSSSLGTQTYTCNVDHKPSNTKVDKRVESKYGPPCPPCPAPEFLG<br>GPSVFLFPPKPKDTLMISRTPEVTCVVVDVSQEDPEVQFNWYVDGVEVHNAKTKPREEQYNSTYRVVSVLTVLHQDWLN<br>GKEYKCKVSNKGLPSSIEKTISKAKGQPREPQVYTLPPSQKEMTKNQVSLTCLVKGFYPSDIAVEWESNGQPENNYKTT<br>PPVLDSDGSFFLYSKLTVDKSRWQEGNVFSCSVMHEALHNHYTQKSLSLSP |
| 90 | T0201H VH domain coding nucleotide sequence | CAGGTGCAGTTGATACAGTCTGGGGCTGAGGTGAAGAAGCCTGGGGCCTCAGTGAAGGTTTCCTGCAAGGCATCTAGAT<br>ACAGCTTCACCAGCTACTATATGCACTGGGTGCGACAGGCCCCTGGACAAGGGCTTGAGTGGATGGGAATAATCAACCC<br>TAAAAGTGGTAGTACAAGTTACGCACAGAAGTTCCAGGGCAGAGTCACCATGACCAGGGACACGTCCACGAGCACAGTC<br>TACATGGAGCTGAGCAGCCTGAGATCTGAGGACACGGCCGTGTATTACTGTGCGAGAGATGGGTATGGCAGCTCGTCCC<br>GGTGCCTCCAGCTCTGGGGCCAGGGCACCCTGGTCACCGTCTCCTCA |
| 91 | T0201H VH domain amino acid sequence | QVQLIQSGAEVKKPGASVKVSCKASRYSFTSYYMHWVRQAPGQGLEWMGIINPKSGSTSYAQKFQGRVTMTRDTSTSTV<br>YMELSSLRSEDTAVYYCARDGYGSSSRCLQLWGQGTLVTVSS |
| 92 | T0736H VH domain coding nucleotide sequence | CAGGTGCAGTTGATACAGTCTGGGGCTGAGGTGAAGAAGCCTGGGGCCTCAGTGAAGGTTTCCTGCAAGGCATCTAGAT<br>ACAAGTTCACCAGCTACTATATGCACTGGGTGCGACAGGCCCCTGGACAAGGGCTTGAGTGGATGGGAATAATCAACCC<br>TAAAAGTGGTAGTACAAGTTACGCACAGAAGTTCCAGGGCAGAGTCACCATGACCAGGGACACGTCCACGAGCACAGTC<br>TACATGGAGCTGAGCAGCCTGAGATCTGAGGACACGGCCGTGTATTACTGTGCGAGAGATGGGTATGGCAGCTTCTCCC<br>GGCTGATCCAGCTCTGGGGCCAGGGCACCCTGGTCACCGTCTCCTCA |
| 93 | T0736H VH domain amino acid sequence | QVQLIQSGAEVKKPGASVKVSCKASRYKFTSYYMHWVRQAPGQGLEWMGIINPKSGSTSYAQKFQGRVTMTRDTSTSTV<br>YMELSSLRSEDTAVYYCARDGYGSFSRLIQLWGQGTLVTVSS |
| 94 | Nucleic acid encoding T0736H-IgG4-P E356K heavy chain | CAGGTTCAGCTGATTCAGTCTGGCGCCGAAGTGAAGAAACCTGGCGCCTCTGTGAAGGTGTCCTGCAAGGCCTCTCGGT<br>ACAAGTTCACCTCCTACTACATGCACTGGGTCCGACAGGCCCCTGGACAAGGATTGGAGTGGATGGGCATCATCAACCC<br>CAAGTCCGGCTCCACCTCTTACGCCCAGAAATTCCAGGGCAGAGTGACCATGACCAGAGACACCTCTACCTCCACCGTG<br>TACATGGAACTGTCCAGCCTGAGATCCGAGGACACCGCCGTGTACTACTGTGCCAGAGATGGCTACGGCAGCTTCTCCA<br>GGCTGATCCAGTTGTGGGGACAGGGCACACTGGTCACCGTGTCCTCTGCTTCTACCAAGGGACCCAGCGTGTTCCCTCT<br>GGCTCCTTGCTCCAGATCCACCTCCGAGTCTACAGCTGCTCTGGGCTGCCTGGTCAAGGACTACTTTCCTGAGCCTGTG<br>ACCGTGTCTTGGAACTCTGGCGCTCTGACATCTGGCGTGCACACCTTTCCAGCTGTGCTGCAGTCCTCCGGCCTGTACT<br>CTCTGTCCTCTGTCGTGACCGTGCCTTCCAGCTCTCTGGGAACCCAGACCTACACCTGTAATGTGGACCACAAGCCTTC<br>CAACACCAAGGTGGACAAGCGCGTGGAATCTAAGTACGGCCCTCCTTGTCCTCCATGTCCTGCTCCAGAGTTTCTCGGC |

TABLE S-continued

| Sequences of antibody heavy and light chain domains, all of which represent embodiments of the present invention. | | |
|---|---|---|
| | | GGACCCTCCGTGTTTCTGTTCCCTCCAAAGCCTAAGGACACCCTGATGATCTCTCGGACCCCTGAAGTGACCTGCGTGG<br>TGGTGGATGTGTCCCAAGAGGATCCCGAGGTGCAGTTCAATTGGTACGTGGACGGCGTGGAAGTGCACAACGCCAAGAC<br>CAAGCCTAGAGAGGAACAGTACAACTCCACCTACAGAGTGGTGTCCGTGCTGACCGTGCTGCACCAGGATTGGCTGAAC<br>GGCAAAGAGTACAAGTGCAAGGTGTCCAACAAGGGCCTGCCTAGCTCCATCGAAAAGACCATCTCCAAGGCCAAGGGCC<br>AGCCTCGAGAACCCCAGGTTTACACCCTGCCTCCAAGCCAGAAAGAGATGACCAAGAACCAGGTGTCCCTGACCTGCCT<br>CGTGAAGGGCTTCTACCCTTCCGATATCGCCGTGGAATGGGAGAGCAATGGCCAGCCAGAGAACAACTACAAGACCACA<br>CCTCCTGTGCTGGACTCCGATGGCTCATTCTTTCTGTACTCCAAGCTGACAGTGGACAAGTCCCGGTGGCAAGAGGGCA<br>ACGTGTTCTCCTGCTCTGTGATGCACGAGGCCCTGCACAACCACTACACCCAGAAGTCCCTGTCTCTGTCCCCT |
| 95 | T0736H-IgG4-P E356K amino acid sequence | QVQLIQSGAEVKKPGASVKVSCKASRYKFTSYYMHWVRQAPGQGLEWMGIINPKSGSTSYAQKFQGRVTMTRDTSTSTV<br>YMELSSLRSEDTAVYYCARDGYGSFSRLIQLWGQGTLVTVSSASTKGPSVFPLAPCSRSTSESTAALGCLVKDYFPEPV<br>TVSWNSGALTSGVHTFPAVLQSSGLYSLSSVVTVPSSSLGTQTYTCNVDHKPSNTKVDKRVESKYGPPCPPCPAPEFLG<br>GPSVFLFPPKPKDTLMISRTPEVTCVVVDVSQEDPEVQFNWYVDGVEVHNAKTKPREEQYNSTYRVVSVLTVLHQDWLN<br>GKEYKCKVSNKGLPSSIEKTISKAKGQPREPQVYTLPPSQKEMTKNQVSLTCLVKGFYPSDIAVEWESNGQPENNYKTT<br>PPVLDSDGSFFLYSKLTVDKSRWQEGNVFSCSVMHEALHNHYTQKSLSLSP |
| 96 | N0128L VL domain coding nucleotide sequence | TCCTATGTGCTGACTCAGCCACCCTCAGTGTCAGTGGCCCCAGGAGAGACGGCCAGGATTACCTGTGGGGGAGACAACA<br>TTGGAAGGAAAAGTGTGTACTGGTACCAGCAGAAGTCAGGCCAGGCCCCTGTGCTGGTCATCTATTATGATAGCGACCG<br>GCCCTCAGGGATCCCTGAGCGATTCTCTGGGTCCAACTCTGGGAACACGGCGACCCTGACCATCAGCAGGGTCGAAGCC<br>GGGGATGAGGCCGACTATTACTGTCAGGTGTGGGATGGAAGTAGTGATCATTGGGTGTTCGGCGGAGGGACCAAGTTGA<br>CCGTCCTAG |
| 97 | N0128L VL domain amino acid sequence | SYVLTOPPSVSVAPGETARITCGGDNIGRKSVYWYQQKSGQAPVLVIYYDSDRPSGIPERFSGSNSGNTATLTISRVEA<br>GDEADYYCQVWDGSSDHWVFGGGTKLTVL |
| 98 | N0128L-IgL λ light chain coding nucleic acid | TCCTATGTGC TGACTCAGCC ACCCTCAGTG TCAGTGGCCC CAGGAGAGAC GGCCAGGATT ACCTGTGGGG<br>GAGACAACAT TGGAAGGAAA AGTGTGTACT GGTACCAGCA GAAGTCAGGC CAGGCCCCTG TGCTGGTCAT<br>CTATTATGAT AGCGACCGGC CCTCAGGGAT CCCTGAGCGA TTCTCTGGGT CCAACTCTGG GAACACGGCG<br>ACCCTGACCA TCAGCAGGGT CGAAGCCGGG GATGAGGCCG ACTATTACTG TCAGGTGTGG GATGGAAGTA<br>GTGATCATTG GGTGTTCGGC GGAGGGACCA AGTTGACCGT CCTAGGTCAG CCCAAGGCTG CCCCCTCGGT<br>CACTCTGTTC CCACCCTCCT CTGAGGAGCT TCAAGCCAAC AAGGCCACAC TGGTGTGTCT CATAAGTGAC<br>TTCTACCCGG GAGCCGTGAC AGTGGCCTGG AAGGCAGATA GCAGCCCCGT CAAGGCGGGA GTGGAGACCA<br>CCACACCCTC CAAACAAAGC AACAACAAGT ACGCGGCCAG CAGCTACCTG AGCCTGACGC CTGAGCAGTG<br>GAAGTCCCAC AAAAGCTACA GCTGCCAGGT CACGCATGAA GGGAGCACCG TGGAGAAGAC AGTGGCCCCT<br>ACAGAATGTT CA |
| 99 | N0128L λ light chain amino acid sequence (mature) | SYVLTQPPSVSVAPGETARITCGGDNIGRKSVYWYQQKSGQAPVLVIYYDSDRPSGIPERFSGSNSGNTATLTISRVEA<br>GDEADYYCQVWDGSSDHWVFGGGTKLTVLGQPKAAPSVTLFPPSSEELQANKATLVCLISDFYPGAVTVAWKADSSPVK<br>AGVETTTPSKQSNNKYAASSYLSLTPEQWKSHKSYSCQVTHEGSTVEKTVAPTECS |
| 100 | N0325L VL domain coding nucleotide sequence | TACGTGCTGACCCAGCCTCCTTCCGTGTCTGTTGCTCCTGGCGAGACAGCCAGAATCACCTGTGGCGGCGATAACATCG<br>GCCGGAAGTCCGTGTACTGGTATCAGCAGAAGTCCGGCCAGGCTCCTGTGCTGGTCATCTACTACGACTCCGACCGGCC<br>TTCTGGCATCCCTGAGAGATTCTCCGGCTCCAACTCCGGCAATACCGCCACACTGACCATCTCCAGAGTGGAAGCTGGC<br>GACGAGGCCGACTACTACTGCCAAGTGTGGGACGGCTCCTCTGACCACTGGGTTTTCGGCGGAGGCACCAAGCTGACAG<br>TGCTG |

TABLE S-continued

| Sequences of antibody heavy and light chain domains, all of which represent embodiments of the present invention. | | |
|---|---|---|
| 101 | N0325L VL domain amino acid sequence | YVLTQPPSVSVAPGETARITCGGDNIGRKSVYWYQQKSGQAPVLVIYYDSDRPSGIPERFSGSNSGNTATLTISRVEAG DEADYYCQVWDGSSDHWVFGGGTKLTVL |
| 102 | N0325L-IgL λ light chain coding nucleic acid; N0325L coding sequence underlined | TACGTGCTGACCCAGCCTCCTTCCGTGTCTGTTGCTCCTGGCGAGACAGCCAGAATCACCTGTGGCGGCGATAACATCG GCCGGAAGTCCGTGTACTGGTATCAGCAGAAGTCCGGCCAGGCTCCTGTGCTGGTCATCTACTACGACTCCGACCGGCC TTCTGGCATCCCTGAGAGATTCTCCGGCTCCAACTCCGGCAATACCGCCACACTGACCATCTCCAGAGTGGAAGCTGGC GACGAGGCCGACTACTACTGCCAAGTGTGGGACGGCTCCTCTGACCACTGGGTTTTCGGCGGAGGCACCAAGCTGACAG TGCTGGGACAACCTAAGGCCGCTCCTTCTGTGACCCTGTTTCCTCCATCCTCCGAGGAACTGCAGGCCAACAAGGCTAC CCTCGTGTGCCTGATCTCCGACTTTTACCCTGGCGCTGTGACCGTGGCCTGGAAGGCTGATAGTTCTCCTGTGAAGGCC GGCGTGGAAACCACCACACCTTCCAAGCAGTCCAACAACAAATACGCCGCCTCCTCCTACCTGTCTCTGACCCCTGAAC AGTGGAAGTCCCACAAGTCCTACTCTTGCCAAGTGACCCACGAGGGCTCCACCGTGGAAAAGACAGTGGCTCCTACCGA GTGCTCC |
| 103 | N0325L λ light chain amino acid sequence (mature) | YVLTQPPSVSVAPGETARITCGGDNIGRKSVYWYQQKSGQAPVLVIYYDSDRPSGIPERFSGSNSGNTATLTISRVEAG DEADYYCQVWDGSSDHWVFGGGTKLTVLGQPKAAPSVTLFPPSSEELQANKATLVCLISDFYPGAVTVAWKADSSPVKA GVETTTPSKQSNNKYAASSYLSLTPEQWKSHKSYSCQVTHEGSTVEKTVAPTECS |
| 104 | IgG4 PE human heavy chain constant region | ASTKGPSVFPLAPCSRSTSESTAALGCLVKDYFPEPVTVSWNSGALTSGVHTFPAVLQSSGLYSLSSVVTVPSSSLGTK TYTCNVDHKPSNTKVDKRVESKYGPPCPPCPAPEFEGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFFLYSRLTVDKSRWQEGNVFSCSVMHEALHNHY TQKSLSLSLGK |
| 105 | IgG4 human heavy chain constant region hinge mutation. Type a (IgG4ra) with knobs-into-holes mutations and | ASTKGPSVFPLAPCSRSTSESTAALGCLVKDYFPEPVTVSWNSGALTSGVHTFPAVLQSSGLYSLSSVVTVPSSSLGTK TYTCNVDHKPSNTKVDKRVESKYGPPCPPCPAPEFEGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPSSIEKTISKAKGQPREPQVCTLPPSQEE MTKNQVSLWCLVKGFYPSDIAVEWESNGQPENNYKTTPPVLDSDGSFFLYSRLTVDKSRWQEGNVFSCSVMHEALHNHY TQKSLSLSLGK |
| 106 | IgG4 human heavy chain constant region with knobs-into-holes mutations and hinge mutation. Type b (IgG4yb) | ASTKGPSVFPLAPCSRSTSESTAALGCLVKDYFPEPVTVSWNSGALTSGVHTFPAVLQSSGLYSLSSVVTVPSSSLGTK TYTCNVDHKPSNTKVDKRVESKYGPPCPPCPAPEFEGGPSVFLFPPKPKDTLMISRTPEVTCVVVDVSQEDPEVQFNWY VDGVEVHNAKTKPREEQFNSTYRVVSVLTVLHQDWLNGKEYKCKVSNKGLPSSIEKTISKAKGQPREPQVYTLPPSQCE MTKNQVSLSCAVKGFYPSDIAVEWESNGQPENNYKTTPPVLDSDGSFFLVSRLTVDKSRWQEGNVFSCSVMHEALHNHY TQKSLSLSLGK |
| 107 | IgG4 human heavy chain constant region with P (hinge) mutation and K439E | ASTKGPSVFPLAPCSRSTSESTAALGCLVKDYFPEPVTVSWNSGALTSGVHTFPAVLQSSGLYSLSSVVTVPSSSLGTQ TYTCNVDHKPSNTKVDKRVESKYGPPCPPCPAPEFLGGPSVFLFPPKPKDTLMISRTPEVTCVVVDVSQEDPEVQFNWY VDGVEVHNAKTKPREEQYNSTYRVVSVLTVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFFLYSKLTVDKSRWQEGNVFSCSVMHEALHNHY TQESLSLSP |
| 108 | IgG4 human heavy chain constant region with P (hinge) mutation and E356K | ASTKGPSVFPLAPCSRSTSESTAALGCLVKDYFPEPVTVSWNSGALTSGVHTFPAVLQSSGLYSLSSVVTVPSSSLGTQ TYTCNVDHKPSNTKVDKRVESKYGPPCPPCPAPEFLGGPSVFLFPPKPKDTLMISRTPEVTCVVVDVSQEDPEVQFNWY VDGVEVHNAKTKPREEQYNSTYRVVSVLTVLHQDWLNGKEYKCKVSNKGLPSSIEKTISKAKGQPREPQVYTLPPSQKE MTKNQVSLTCLVKGFYPSDIAVEWESNGQPENNYKTTPPVLDSDGSFFLYSKLTVDKSRWQEGNVFSCSVMHEALHNHY TQKSLSLSP |

TABLE S-continued

Sequences of antibody heavy and light chain domains, all of which represent embodiments of the present invention.

| | | |
|---|---|---|
| 109 | IgG4-P K439E encoding nucleic acid | GCTTCCACCAAGGGACCCAGCGTTTTCCCTCTGGCTCCTTGCTCCAGATCCACCTCCGAGTCTACAGCTGCTCTGGGCT GCCTGGTCAAGGACTACTTTCCTGAGCCTGTGACCGTGTCCTGGAACTCTGGCGCTCTGACATCTGGCGTGCACACCTT TCCAGCTGTGCTGCAGTCCTCCGGCCTGTACTCTCTGTCCTCTGTCGTGACCGTGCCTTCCAGCTCTCTGGGAACCCAG ACCTACACCTGTAATGTGGACCACAAGCCTTCCAACACCAAGGTGGACAAGCGCGTGGAATCTAAGTACGGCCCTCCTT GTCCTCCATGTCCTGCTCCAGAGTTTCTCGGCGGACCCTCCGTGTTTCTGTTCCCTCCAAAGCCTAAGGACACCCTGAT GATCTCTCGGACCCCTGAAGTGACCTGCGTGGTGGTGGATGTGTCCCAAGAGGATCCCGAGGTGCAGTTCAATTGGTAC GTGGACGGCGTGGAAGTGCACAATGCCAAGACCAAGCCTAGAGAGGAACAGTACAACTCCACCTACAGAGTGGTGTCCG TGCTGACCGTGCTGCACCAGGATTGGCTGAACGGCAAAGAGTACAAGTGCAAGGTGTCCAACAAGGGCCTGCCTAGCTC CATCGAAAAGACCATCTCCAAGGCCAAGGGCCAGCCTCGAGAACCCCAGGTTTACACCCTGCCTCCAAGCCAAGAGGAA ATGACCAAGAACCAGGTGTCCCTGACCTGTCTCGTGAAGGGCTTCTACCCCTCCGATATCGCCGTGGAATGGGAGTCTA ATGGCCAGCCAGAGAACAACTACAAGACCACACCTCCAGTGCTGGACTCCGACGGCTCATTCTTTCTGTACTCCAAGCT GACAGTGGACAAGTCCCGGTGGCAAGAGGGCAACGTGTTCTCCTGCTCTGTGATGCACGAGGCCCTGCACAACCACTAC ACCCAAGAGTCCCTGTCTCTGTCCCCT |
| 110 | IgG4-P E356K encoding nucleic acid | GCTTCCACCAAGGGACCCAGCGTGTTCCCTCTGGCTCCTTGCTCCAGATCCACCTCCGAGTCTACAGCTGCTCTGGGCT GCCTGGTCAAGGACTACTTTCCTGAGCCTGTGACCGTGTCTTGGAACTCTGGCGCTCTGACATCTGGCGTGCACACCTT TCCAGCTGTGCTGCAGTCCTCCGGCCTGTACTCTCTGTCCTCTGTCGTGACCGTGCCTTCCAGCTCTCTGGGAACCCAG ACCTACACCTGTAATGTGGACCACAAGCCTTCCAACACCAAGGTGGACAAGCGCGTGGAATCTAAGTACGGCCCTCCTT GTCCTCCATGTCCTGCTCCAGAGTTTCTCGGCGGACCCTCCGTGTTTCTGTTCCCTCCAAAGCCTAAGGACACCCTGAT GATCTCTCGGACCCCTGAAGTGACCTGCGTGGTGGTGGATGTGTCCCAAGAGGATCCCGAGGTGCAGTTCAATTGGTAC GTGGACGGCGTGGAAGTGCACAACGCCAAGACCAAGCCTAGAGAGGAACAGTACAACTCCACCTACAGAGTGGTGTCCG TGCTGACCGTGCTGCACCAGGATTGGCTGAACGGCAAAGAGTACAAGTGCAAGGTGTCCAACAAGGGCCTGCCTAGCTC CATCGAAAAGACCATCTCCAAGGCCAAGGGCCAGCCTCGAGAACCCCAGGTTTACACCCTGCCTCCAAGCCAGAAAGAG ATGACCAAGAACCAGGTGTCCCTGACCTGCCTCGTGAAGGGCTTCTACCCTTCCGATATCGCCGTGGAATGGGAGAGCA ATGGCCAGCCAGAGAACAACTACAAGACCACACCTCCTGTGCTGGACTCCGATGGCTCATTCTTTCTGTACTCCAAGCT GACAGTGGACAAGTCCCGGTGGCAAGAGGGCAACGTGTTCTCCTGCTCTGTGATGCACGAGGCCCTGCACAACCACTAC ACCCAGAAGTCCCTGTCTCTGTCCCCT |
| 111 | Nucleic acid encoding IgL human lambda light chain constant region | GGACAACCTAAGGCCGCTCCTTCTGTGACCCTGTTTCCTCCATCCTCCGAGGAACTGCAGGCCAACAAGGCTACCCTCG TGTGCCTGATCTCCGACTTTTACCCTGGCGCTGTGACCGTGGCCTGGAAGGCTGATAGTTCTCCTGTGAAGGCCGGCGT GGAAACCACCACACCTTCCAAGCAGTCCAACAACAAATACGCCGCCTCCTCCTACCTGTCTCTGACCCCTGAACAGTGG AAGTCCCACAAGTCCTACTCTTGCCAAGTGACCCACGAGGGCTCCACCGTGGAAAAGACAGTGGCTCCTACCGAGTGCT CC |
| 112 | Human lambda light chain constant region | GOPKAAPSVTLFPPSSEELQANKATLVCLISDFYPGAVTVAWKADSSPVKAGVETTTPSKQSNNKYAASSYLSLTPEQW KSHKSYSCQVTHEGSTVEKTVAPTECS |
| 113 | Human kappa light chain constant region | KRTVAAPSVFIFPPSDEQLKSGTASVVCLLNNFYPREAKVQWKVDNALQSGNSQESVTEQDSKDSTYSLSSTLTLSKAD YEKHKVYACEVTHQGLSSPVTKSFNRGEC |

What is claimed is:

1. A method of expressing a bispecific antibody comprising two heavy chains and a common light chain, the method comprising:

providing a host cell comprising a nucleic acid encoding a polypeptide comprising an antibody light chain variable (VL) domain with an N-terminal signal peptide, wherein the VL domain comprises a sequence derived from a v λ gene segment and a sequence derived from a j gene segment, wherein the N-terminal signal peptide differs from the native N-terminal signal peptide for said v λ gene segment, and wherein the residue corresponding to IMGT position 1 of the VL domain is absent, wherein the host cell further comprises one or more nucleic acids encoding the two heavy chains, culturing said host cell under conditions for expression of the antibody heavy and light chains, wherein the N-terminal signal peptide is cleaved off the VL domain to provide an antibody light chain comprising a mature VL domain, wherein the N-terminal residue of the polypeptide comprising the mature VL domain is IMGT position 2 of the VL domain, and wherein the light chain domain assembles with each of the two heavy chains to provide said bispecific antibody.

2. The method of claim 1, wherein the v λ gene segment is a human Vλ3-21 gene segment.

3. The method of claim 1, wherein the bispecific antibody comprises a heavy chain comprising the N1441H VH domain SEQ ID NO: 83;

a heavy chain comprising the T0999H VH domain SEQ ID NO: 87; and a common light chain comprising the 0325L VL domain SEQ ID NO: 101.

4. The method of claim 1, wherein the v λ gene segment is a human v λ gene segment.

5. The method of claim 1, wherein the j gene segment is a human j λ gene segment.

6. The method of claim 1, wherein the first encoded residue (IMGT position 1) of the v λ gene segment is Ser.

7. The method of claim 1, wherein the v λ gene segment is a vertebrate IGL V3 family gene segment.

8. The method of claim 1, wherein the first two encoded residues (IMGT positions 1 to 2) of the v λ gene segment are Ser Tyr.

9. The method of claim 1, wherein the first three encoded residues (IMGT positions 1 to 3) of the v λ gene segment are Ser Tyr Val.

10. The method of claim 1, wherein the polypeptide comprises the VL domain and a light chain constant (CL) domain.

11. The method of claim 10, wherein the CL domain is a λCL domain.

12. The method of claim 1, wherein the VL domain is a N0325L VL domain.

13. The method of claim 1, wherein the nucleic acid encoding the VL domain comprises SEQ ID NO:100.

14. The method of claim 1, wherein the host cell is a mammalian cell.

15. The method of claim 1, wherein the nucleic acid is integrated into chromosomal DNA of the host cell.

16. The method of claim 1, wherein the host cell is a CHO cell.

17. The method of claim 1, wherein the nucleic acid is cDNA.

18. The method of claim 1, further comprising isolating the antibody from the host cell.

19. The method of claim 18, wherein the isolating comprises one or more steps of protein chromatography.

* * * * *